US012108661B2

(12) United States Patent
Lee et al.

(10) Patent No.: US 12,108,661 B2
(45) Date of Patent: *Oct. 1, 2024

(54) COMPOUND FOR ORGANIC ELECTRIC ELEMENT, ORGANIC ELECTRIC ELEMENT COMPRISING THE SAME, AND ELECTRONIC DEVICE THEREOF

(71) Applicant: DUK SAN NEOLUX CO., LTD., Cheonan-si (KR)

(72) Inventors: Se Hoon Lee, Cheonan-si (KR); Yun Suk Lee, Cheonan-si (KR); Jung Hwan Park, Cheonan-si (KR); Jung Wook Lee, Cheonan-si (KR); Sun Hee Lee, Cheonan-si (KR); Tae Seop Choi, Cheonan-si (KR); Hyun Ji Oh, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 433 days.

This patent is subject to a terminal disclaimer.

(21) Appl. No.: 15/733,301

(22) PCT Filed: Dec. 17, 2018

(86) PCT No.: PCT/KR2018/016002

§ 371 (c)(1),
(2) Date: Jun. 22, 2020

(87) PCT Pub. No.: WO2019/124903

PCT Pub. Date: Jun. 27, 2019

(65) Prior Publication Data

US 2020/0321530 A1 Oct. 8, 2020

(30) Foreign Application Priority Data

Dec. 21, 2017 (KR) ........................ 10-2017-0176823
Nov. 15, 2018 (KR) ........................ 10-2018-0140620

(51) Int. Cl.
*H10K 85/60* (2023.01)
*C07D 333/76* (2006.01)
(Continued)

(52) U.S. Cl.
CPC ......... *H10K 85/636* (2023.02); *C07D 333/76* (2013.01); *C07D 409/12* (2013.01);
(Continued)

(58) Field of Classification Search
CPC .. C07D 307/91; C07D 333/76; C07D 407/12; C07D 409/12; C07D 409/14
See application file for complete search history.

(56) References Cited

U.S. PATENT DOCUMENTS 10,319,915 B2 * 6/2019 Park ...................... C09K 11/06
10,651,391 B2 * 5/2020 Park ...................... H05B 33/14
(Continued)

FOREIGN PATENT DOCUMENTS

KR 10-1614739 B1 4/2016
KR 10-1668448 B1 10/2016
(Continued)

*Primary Examiner* — Valerie Rodriguez-Garcia
(74) *Attorney, Agent, or Firm* — The PL Law Group, PLLC

(57) ABSTRACT

The present invention provides an organic electroluminescent element and electronic device thereof, wherein the organic electroluminescent element comprises the compound represented by Formula 1 as material for an emission-auxiliary layer, and by comprising the compound represented by Formula 1 in the emission-auxiliary layer, the driving voltage of the organic electroluminescent element can be lowered, and the luminous efficiency and life time of the organic electroluminescent element can be improved.

10 Claims, 1 Drawing Sheet

(51) Int. Cl.

| | |
|---|---|
| ***C07D 409/12*** | (2006.01) |
| ***C07D 409/14*** | (2006.01) |
| ***C09K 11/06*** | (2006.01) |
| ***H10K 50/15*** | (2023.01) |

(52) U.S. Cl.
CPC ............ *C07D 409/14* (2013.01); *C09K 11/06* (2013.01); *C09K 2211/1018* (2013.01); *H10K 50/156* (2023.02); *H10K 85/6574* (2023.02); *H10K 85/6576* (2023.02)

(56) References Cited

U.S. PATENT DOCUMENTS

| | | | | |
|---|---|---|---|---|
| 2017/0237013 A1* | 8/2017 | Park | C09K 11/06 257/40 |
| 2018/0358563 A1* | 12/2018 | Park | C09K 11/06 |

FOREIGN PATENT DOCUMENTS

| | | | |
|---|---|---|---|
| KR | 10-2017-0112913 A | 10/2017 |
| KR | 10-2017-0134215 A | 12/2017 |
| WO | 2018/012780 A1 | 1/2018 |
| WO | 2018/021737 A1 | 2/2018 |

* cited by examiner

COMPOUND FOR ORGANIC ELECTRIC ELEMENT, ORGANIC ELECTRIC ELEMENT COMPRISING THE SAME, AND ELECTRONIC DEVICE THEREOF

CROSS-REFERENCE TO RELATED APPLICATION

This patent application claims priority from and the benefit under 35 U.S.C. § 119 to § 121, and § 365 of Korean Patent Application No. 10-2017-0176823, filed on Dec. 21, 2017 and Korean Patent Application No. 10-2018-0140620, filed on Nov. 15, 2018 which are hereby incorporated by reference for all purposes as if fully set forth herein. Further, this application claims the benefit of priority in countries other than U.S., which is hereby incorporated by reference herein.

BACKGROUND

Technical Field

The present invention relates to compound for an organic electric element, an organic electric element comprising the same and an electronic device thereof.

Background Art

In general, an organic light emitting phenomenon refers to a phenomenon in which electric energy is converted into light energy of an organic material. An organic electric element utilizing the organic light emitting phenomenon usually has a structure including an anode, a cathode, and an organic material layer interposed therebetween. In many cases, the organic material layer has a multi-layered structure having respectively different materials in order to improve efficiency and stability of an organic electric element, and for example, may include a hole injection layer, a hole transport layer, a light emitting layer, an electron transport layer, an electron injection layer, or the like.

Materials used as an organic material layer in an organic electric element may be classified into a light emitting material and a charge transport material, for example, a hole injection material, a hole transport material, an electron transport material, an electron injection material, and the like according to its function.

Currently, the power consumption is required more than more as size of display becomes larger and larger in the portable display market. Therefore, the power consumption is a very important factor in the portable display with a limited power source of the battery, and efficiency and life span issue also is solved.

Efficiency, life span, driving voltage, and the like are correlated with each other. if efficiency is increased, then driving voltage is relatively lowered, and the crystallization of an organic material due to Joule heating generated during operation is reduced as driving voltage is lowered, as a result of which life span shows a tendency to increase. However, efficiency cannot be maximized only by simply improving the organic material layer. This is because long life span and high efficiency can be simultaneously achieved when an optimal combination of energy levels and $T_1$ values, inherent material properties (mobility, interfacial properties, etc.), and the like among the respective layers included in the organic material layer is given.

In addition, in the recent organic electroluminescent devices, an emission-auxiliary layer (multi-layered hole transport layer) must be present between the hole transport layer and the light emitting layer in order to solve the problems of luminescence in the hole transport layer and the driving voltage, and it is necessary to develop different emission-auxiliary layers according to respective light emitting layers.

In general, an electron is transferred from an electron transport layer to a light emitting layer and a hole is transferred from a hole transport layer to the light emitting layer, as a result, an exciton is formed by the recombination of the electron and hole within the light emitting layer.

However, material used in a hole transport layer has a low T1 value because the material should have a low HOMO value. As a result, the exciton generated in the light emitting layer is transferred to the hole transport layer and it causes charge unbalance in the light emitting layer, thereby emitting light at the interface of the hole transport layer.

When light is emitted from the interface of the hole transporting layer, the color purity and efficiency of the organic electronic element are lowered and the lifetime is shortened. Therefore, it is strongly desired to develop materials for the emission-auxiliary layer having a HOMO level between the HOMO energy level of the hole transporting layer and the HOMO energy level of the light emitting layer, a high T1 energy value and a hole mobility within a suitable driving voltage range (within a driving voltage range of blue element of a full device).

However, this cannot be achieved simply by the structural properties of the core of the emission-auxiliary layer material. An element having a high efficiency and a long life span can be realized when the characteristics of core and sub-substituents of the emission-auxiliary layer material, the proper combination of the emission-auxiliary layer and the hole transport layer, and the proper combination of the emission-auxiliary layer and the light emitting layer.

In order to fully exhibit the excellent characteristics of the organic electric element, materials forming the organic material layer in the element, such as a hole injection material, a hole transport material, a light emitting material, an electron transport material, an electron injection material, an emission-auxiliary layer material, etc. should be prerequisite to support by a stable and efficient material, and in particular, it is strongly required to develop material for an emission-auxiliary layer.

OBJECT, TECHNICAL SOLUTION AND EFFECTS OF THE INVENTION

An object of the present invention is to provide a compound lowering a driving voltage, improving luminous efficiency, color purity and lifetime of the element, an organic electric element comprising the same, and an electronic device thereof.

In an aspect of the present invention, the present invention provides the compound represented by the following formula.

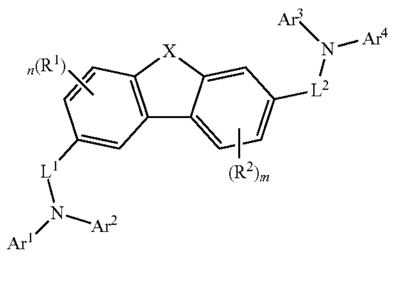

In another aspect of the present invention, the present invention provides an organic electric element employing the compound represented by formula above and an electronic device thereof.

By using the compound according to embodiment of the present invention, a driving voltage of an organic electric element can be lowered and the luminous efficiency, color purity and lifetime of the element can be largely improved.

DETAILED DESCRIPTION

Figure 1:
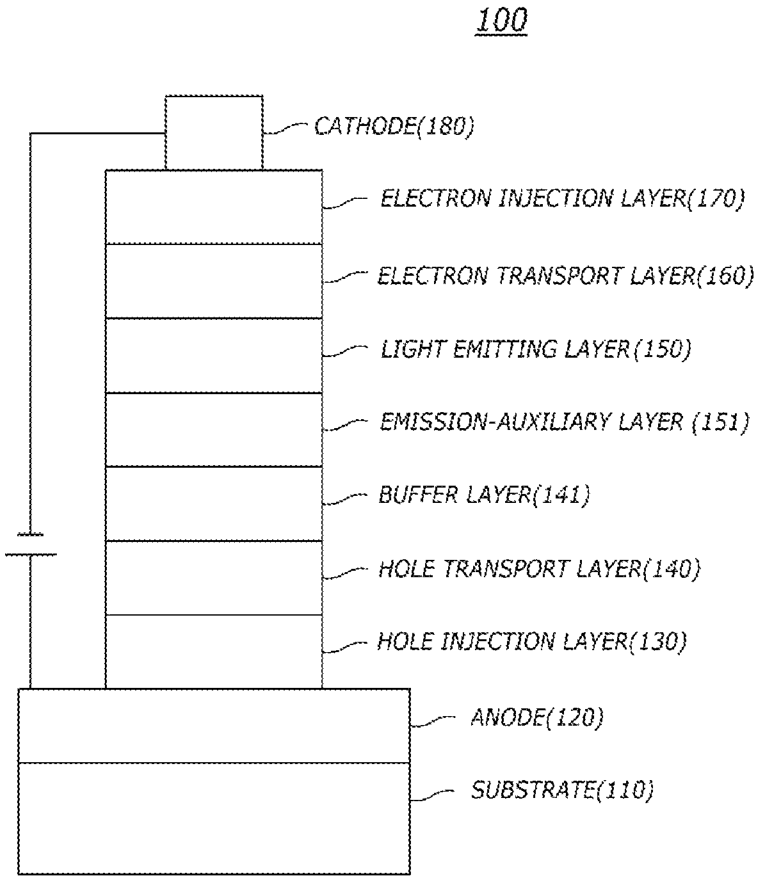
FIG. 1 illustrates an example of an organic electroluminescent element according to the present invention: 100 is an organic electric element, 110 is a substrate, 120 is a first electrode, 130 is a hole injection layer, 140 is a hole transport layer, 141 is a buffer layer, 150 is a light emitting layer, 151 is an emission-auxiliary layer, 160 is an electron transport layer, 170 is an electron injection layer, and 180 is a second electrode.

Unless otherwise stated, the term "aryl group" or "arylene group" as used herein has, but not limited to, 6 to 60 carbon atoms. The aryl group or arylene group in the present invention may comprise a monocyclic ring, ring assemblies, a fused polycyclic system, spiro compounds and the like. In addition, unless otherwise stated, a fluorenyl group may be comprised in an aryl group and a fluorenylene group may be comprised in an arylene group.

Unless otherwise stated, the term "fluorenyl group" or "fluorenylene group" as used herein means "substituted or unsubstituted fluorenyl group" "substituted or unsubstituted fluorenylene group", respectively. "Fluorenyl group" or "fluorenylene group" as used herein may be represented by the following formula, wherein R, R' and R" may be hydrogen or a substituent other than hydrogen and R and R' are linked to each other to form the spiro compound together with the carbon to which they are bonded.

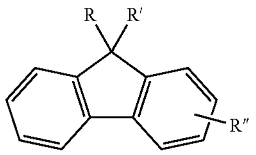

The term "spiro compound" as used herein has a spiro union which means union having one atom as the only common member of two rings. The common atom is designated as 'spiro atom'. The compounds are defined as 'monospiro-', 'dispiro-' or 'trispiro-' depending on the number of spiro atoms in one compound.

Unless otherwise stated, the term "heterocyclic group" as used herein means, but not limited to, a non-aromatic ring as well as an aromatic ring like "heteroaryl group" or "heteroarylene group". The heterocyclic group as used herein means, but not limited to, a ring containing one or more heteroatoms, and having 2 to 60 carbon atoms. Unless otherwise stated, the term "heteroatom" as used herein represents N, O, S, P or Si. The heterocyclic group means a monocyclic, ring assemblies, fused polycyclic system or spiro compound containing a heteroatom.

In addition, "heterocyclic group" means a ring comprising a heteroatom such as N, O, S, P, Si and so on instead of carbon forming a ring, it comprises a non-aromatic ring as well as an aromatic ring like "heteroaryl group" or "heteroarylene group", and it comprises the compound comprising a heteroatom group such as $SO_2$, P=O etc. instead of carbon forming a ring such as the following compound.

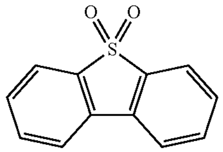 [SMILES: O=S1(=O)c2ccccc2-c2ccccc21]

The term "aliphatic ring group" as used herein refers to a cyclic hydrocarbon except for aromatic hydrocarbons, and comprises a monocyclic ring, ring assemblies, a fused polycyclic system, spiro compounds, and the like, and unless otherwise specified, it means a ring of 3 to 60 carbon atoms, but not limited thereto. For example, a fused ring formed by benzene being an aromatic ring with cyclohexane being a non-aromatic ring corresponds to aliphatic ring.

In this specification, a 'group name' corresponding to an aryl group, an arylene group, a heterocyclic group, and the like exemplified for each symbol and its substituent may be written in the name of functional group reflecting the valence, and may also be described as the name of a parent compound. For example, in the case of phenanthrene which is a kind of aryl group, it may be described by distinguishing valence such as 'phenanthryl (group)' when it is 'monovalent group', and as 'phenanthrylene (group)' when it is 'divalent group', and it may also be described as a parent compound name, 'phenanthrene', regardless of its valence. Similarly, in the case of pyrimidine, it may be described as 'pyrimidine' regardless of its valence, and it may also be described as the name of corresponding functional group such as pyrimidinyl (group) when it is 'monovalent group', and as 'pyrimidylene (group)' when it is 'divalent group'.

In addition, in the present specification, the numbers and alphabets indicating a position may be omitted when describing a compound name or a substituent name. For example, pyrido[4,3-d]pyrimidine, benzopuro[2,3-d] pyrimidine and 9,9-dimethyl-9H-fluorene can be described as pyridopyrimidine, benzofurropyrimidine and dimethylfluorene, respectively. Therefore, both benzo[g]quinoxaline and benzo[f]quinoxaline can be described as benzoquinoxaline.

In addition, unless otherwise expressed, where any formula of the present invention is represented by the following formula, the substituent according to the index may be defined as follows.

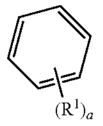

In the above formula, where a is an integer of zero, the substituent $R^1$ is absent, that is, hydrogen atoms are bonded to all the carbon constituting the benzene ring. Here, chemical formulas or compounds may be written without explicitly describing the hydrogen. In addition, one substituent $R^1$ is bonded to any carbon of the carbons forming the benzene ring when "a" is an integer of 1. Similarly, where "a" is an integer of 2 or 3, substituents $R^1$s may be bonded to the carbon of the benzene ring, for example, as followings. Also, where "a" is an integer of 4 to 6, substituents $R^1$s are bonded to the carbon of the benzene ring in a similar manner. Further, where "a" is an integer of 2 or more, $R^1$s may be the same or different from each other.

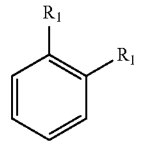

(a = 2)

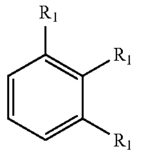

(a = 3)

Hereinafter, a laminated structure of the electric element comprising the compound of the present invention will be described with reference to FIG. 1.

FIG. 1 illustrates a laminated structure of an organic electric element according to an embodiment of the present invention.

Referring to FIG. 1, an organic electric element 100 according to an embodiment of the present invention includes a first electrode 120 formed on a substrate 110, a second electrode 180, and an organic material layer formed between the first electrode 120 and the second electrode 180 and comprising the compound of the present invention. Here, the first electrode 120 may be an anode (positive electrode), and the second electrode 180 may be a cathode (negative electrode). In the case of an inverted organic electroluminescent element, the first electrode may be a cathode, and the second electrode may be an anode.

The organic material layer may include a hole injection layer 130, a hole transport layer 140, a light emitting layer 150, an electron transport layer 160, and an electron injection layer 170 formed in sequence on the first electrode 120. Here, at least one layer of the organic material layer may be omitted, or the organic material layer may further include a hole blocking layer, an electron blocking layer, an emission-auxiliary layer 151, a buffer layer 141, etc., and the electron transport layer 160 or the like may serve as a hole blocking layer.

In addition, although not shown, the organic electric element according to an embodiment of the present invention may further include a protective layer or a layer for improving luminous efficiency formed on at least one side of sides of the first electrode and the second electrode, wherein at least one side is not facing the organic material layer.

The inventive compound employed in the organic material layer may be used as a material of a hole injection layer 130, a hole transport layer 140, electron transport layer 160, an electron injection layer 170, a light emitting layer 150, a layer for improving luminous efficiency, an emission-auxiliary layer and so on. Preferably, the inventive compound may be used as material of a hole transport layer 140 and/or an emission-auxiliary layer 151, more preferably, as material of an emission-auxiliary layer 151.

On the other hand, even if the core is same, the band gap, the electrical characteristics, the interface characteristics and the like may be different depending on which substituent is bonded at which position. Therefore, the selection of the core and the combination of the core and the sub-substituent bonded to the core are very important. In particular, long life span and high efficiency can be simultaneously achieved when the optimal combination of energy levels and $T_1$ values, inherent material properties (mobility, interfacial properties, etc.), and the like among the respective layers of an organic material layer is achieved.

As already described above, recently, in order to solve the emission problem with a hole transport layer of an organic electric element, it is preferable that an emission-auxiliary layer is formed between the hole transport layer and a light emitting layer, and it is necessary to develop different emission-auxiliary layers according to respective light emitting layers (R, G, B). On the other hand, even if the core of an emission-auxiliary layer is similar, it is very difficult to infer the characteristics of an emission-auxiliary layer because it is necessary to grasp the correlation between the emission-auxiliary layer and a hole transport layer and a light emitting layer (host).

Therefore, according to the present invention, energy level and $T_1$ value between the respective layers of the organic material layer, inherent material properties (mobility, interfacial properties, etc.) and the like can be optimized by forming a hole transport layer and/or an emission-auxiliary layer with the compound of the present invention, and thus it is possible to simultaneously improve the life span and efficiency of the organic electric element.

The organic electric element according to an embodiment of the present invention may be manufactured using various deposition methods. The organic electric element according to an embodiment of the present invention may be manufactured using a PVD (physical vapor deposition) method or CVD (chemical vapor deposition) method. For example, the organic electric element may be manufactured by depositing a metal, a conductive metal oxide, or a mixture thereof on the substrate to form the anode 120, forming the organic material layer including the hole injection layer 130, the hole transport layer 140, the light emitting layer 150, the electron transport layer 160, and the electron injection layer 170 thereon, and then depositing a material, which can be used as the cathode 180, thereon. In particular, an emitting auxiliary layer 151 may be formed between a hole transport layer 140 and a light emitting layer 150.

Also, the organic material layer may be manufactured in such a manner that a smaller number of layers are formed using various polymer materials by a soluble process or solvent process, for example, spin coating, nozzle printing, inkjet printing, slot coating, dip coating, roll-to-roll, doctor blading, screen printing, or thermal transfer, instead of deposition. Since the organic material layer according to the present invention may be formed in various ways, the scope of protection of the present invention is not limited by a method of forming the organic material layer.

The organic electric element according to the present invention may be one of an organic light emitting device (OLED), an organic solar cell, an organic photo conductor (OPC), an organic transistor, an element for monochromatic or white illumination and an element quantum dot display.

Another embodiment of the present invention provides an electronic device including a display device which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electric dictionary, a point-to-multipoint (PMP), a remote controller, a navigation unit, a game player, various kinds of TVs, and various kinds of computers, and the display device may comprise an electroluminescent display, a quantum dot display and so on.

Hereinafter, referring to FIG. 2, the compound according to an aspect of the present invention will be described.

Figure 2:
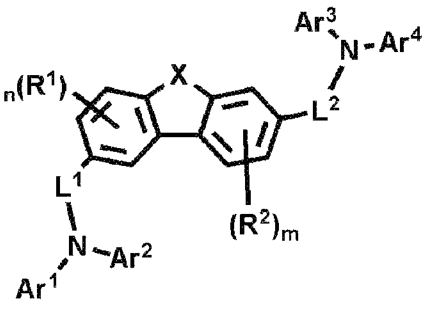
FIG. 2 shows Formula according to an aspect of the present invention.

FIG. 2 is Formula according to an aspect of the present invention, which is as shown in Formula 1 below.

<Formula 1>

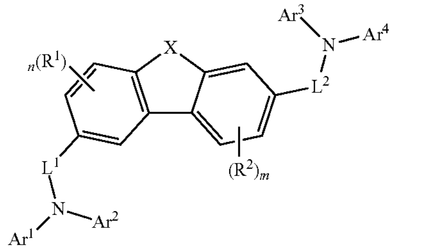

<Formula 1-1>

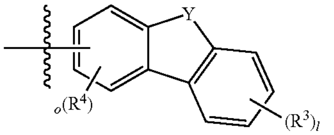

In the formula above, each of symbols may be defined as follows.

X and Y are each independently O or S.

$Ar^1$ to $Ar^4$ are each independently selected from the group consisting of halogen, a $C_6$-$C_{60}$ aryl group, a fluorenyl group, a $C_2$-$C_{60}$ heterocyclic group containing at least one heteroatom of O, N, S, Si, and P, a $C_3$-$C_{60}$ aliphatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group, -L'-N($R_a$)($R_b$) and Formula 1-1, with the proviso that at least one of $Ar^1$ to $Ar^4$ is Formula 1-1.

In addition, $Ar^1$ and $Ar^2$ together or $Ar^3$ and $Ar^4$ together may be bonded to each other to form a ring. Therefore, where they combine with each other to form a ring, a $C_2$-$C_{60}$ heterocyclic group comprising N, preferably, a $C_2$-$C_{30}$ heterocyclic group, more preferably, a $C_2$-$C_{12}$ heterocyclic group may be formed.

Where $Ar^1$ to $Ar^4$ are an aryl group, the aryl group may be preferably a $C_6$-$C_{30}$, more preferably a $C_6$-$C_{18}$ aryl group, for example, phenyl, biphenyl, terphenyl, naphthyl, phenanthrene, pyrene and the like. Where $Ar^1$ to $Ar^4$ are a heterocyclic group, the heterocyclic group may be preferably a $C_2$-$C_{30}$, more preferably a $C_2$-$C_{12}$ heterocyclic group, for example, quinazoline, dibenzothiophene, dibenzofuran and the like. Where $Ar^1$ to $Ar^4$ are a fluorenyl group, the fluorenyl group may be 9,9-dimethyl-9H-fluorene, 9,9-diphenyl-9H-fluorene, 9,9'-spirofluorene and the like.

$L^1$ and $L^2$ are each independently selected from the group consisting of a single bond, a $C_6$-$C_{60}$ arylene group, a fluorenylene group, a $C_2$-$C_{60}$ heterocyclic group containing at least one heteroatom of O, N, S, Si, and P, a $C_3$-$C_{60}$ aliphatic ring and a combination thereof.

Where $L^1$ and $L^2$ are an arylene group, the arylene group may be preferably a $C_6$-$C_{30}$, more preferably a $C_6$-$C_{18}$ arylene group, for example, phenyl, biphenyl, terphenyl, naphthyl and the like.

$R^1$ to $R^4$ are each independently selected from the group consisting of hydrogen, deuterium, halogen, a $C_6$-$C_{60}$ aryl group, a fluorenyl group, a $C_2$-$C_{60}$ heterocyclic group containing at least one heteroatom of O, N, S, Si, and P, a $C_3$-$C_{60}$ aliphatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N($R_a$)($R_b$).

In addition, adjacent $R^1$ groups to adjacent $R^4$ groups together may be bonded to each other to form a ring. Specifically, adjacent $R^1$s, adjacent $R^2$s, adjacent $R^3$s or adjacent $R^4$s together may be bonded to each other to form a ring selected from the group consisting of a $C_6$-$C_{60}$ aromatic hydrocarbon, a $C_2$-$C_{60}$ heterocyclic group containing at least one heteroatom of O, N, S, Si, and P, a $C_3$-$C_{60}$ aliphatic ring, and a combination thereof. Where adjacent groups together may be bonded to each other to form an aromatic hydrocarbon, the aromatic hydrocarbon is preferably a $C_6$-$C_{30}$ aromatic ring, more preferably a $C_6$-$C_{14}$, for example, benzene, naphthalene, phenanthrene and the like.

With the proviso that at least one of $R^2$s is -L'-N($R_a$)($R_b$) where X is S.

l is an integer of 1 to 4, m, n and o are each an integer of 1 to 3, where they are each an integer of 2 or more, each of a plurality of $R^1$s, each of a plurality of $R^2$s, each of a plurality of $R^3$s, each of a plurality of $R^4$s are the same or different from each other.

Where $R^1$ to $R^4$ are an aryl group, the aryl group may be preferably a $C_6$-$C_{30}$, more preferably a $C_6$-$C_{18}$ aryl group, for example, phenyl, biphenyl, terphenyl, naphthyl and the like. Where $R^1$ to $R^4$ are an alkyl group, the alkyl group may be preferably a $C_2$-$C_{20}$, more preferably a $C_2$-$C_{10}$ alkyl group, for example, methyl, ethyl, t-butyl and the like. Where $R^1$ to $R^4$ are halogen, the halogen may be chlorine, fluorine and the like.

L' is selected from the group consisting of a single bond, a $C_6$-$C_{60}$ arylene group, a fluorenylene group, a $C_3$-$C_{60}$ aliphatic ring and a $C_2$-$C_{60}$ heterocyclic group containing at least one heteroatom of O, N, S, Si, and P.

Where L' is an arylene group, the arylene group may be preferably a $C_6$-$C_{30}$, more preferably a $C_6$-$C_{18}$ arylene group, for example, phenyl, biphenyl, terphenyl, naphthyl and the like.

$R_a$ and $R_b$ are each independently selected from the group consisting of a $C_6$-$C_{60}$ aryl group, a fluorenyl group, a fused ring group formed by a $C_3$-$C_{60}$ aliphatic ring with a $C_6$-$C_{60}$ aromatic ring, and a $C_2$-$C_{60}$ heterocyclic group containing at least one heteroatom of O, N, S, Si, and P.

Where $R_a$ and $R_b$ are an aryl group, the aryl group may be preferably a $C_6$-$C_{30}$, more preferably a $C_6$-$C_{18}$ aryl group, for example, phenyl, biphenyl, terphenyl, naphthyl and the like. Where $R_a$ and $R_b$ are a heterocyclic group, the heterocyclic group may be preferably a $C_2$-$C_{30}$, more preferably a $C_2$-$C_{12}$ heterocyclic group, for example, pyridine, dibenzothiophene, dibenzofuran and the like. Where $R_a$ and $R_b$ are a fluorenyl group, the fluorenyl group may be 9,9-dimethyl-9H-fluorene, 9,9-diphenyl-9H-fluorene, 9,9'-spirofluorene and the like.

$Ar^1$ to $Ar^4$, $L^1$, $L^2$, L', $R^1$ to $R^4$, $R_a$, $R_b$, the ring formed by adjacent groups may be each optionally substituted with one or more substituents selected from the group consisting of deuterium, halogen, a silane group unsubstituted or substituted with a $C_1$-$C_{20}$ alkyl group or a $C_6$-$C_{20}$ aryl group, a siloxane group, a boron group, a germanium group, a cyano group, a nitro group, a phosphine oxide group unsubstituted or substituted with a $C_1$-$C_{20}$ alkyl group or a $C_6$-$C_{20}$ aryl group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom of O, N, S, Si, and P, a $C_3$-$C_{20}$ cycloalkyl group, a $C_7$-$C_{20}$ arylalkyl group, and $C_8$-$C_{20}$ arylalkenyl group.

Preferably, Formula 1 may be represented by Formula 2 or Formula 3.

<Formula 2>

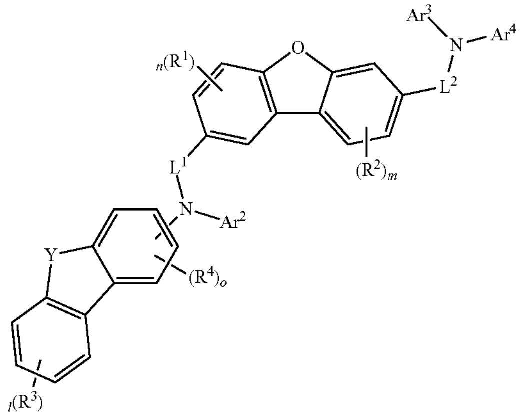

<Formula 3>

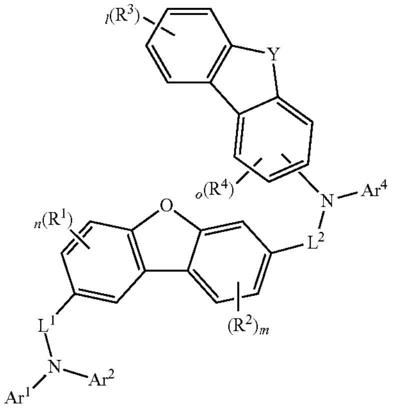

In Formulas 2 and 3, $Ar^1$ to $Ar^4$, $R^1$ to $R^4$, $L^1$, $L^2$, Y, l, m, n, o are the same as defined for Formula 1.

In addition, Formula 1 may be represented by one of Formula 4 to Formula 7.

<Formula 4>

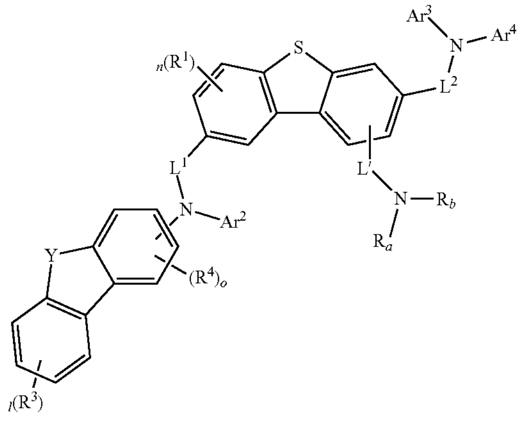

-continued

<Formula 5>

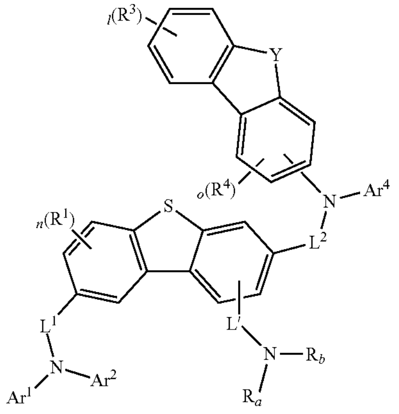

<Formula 6>

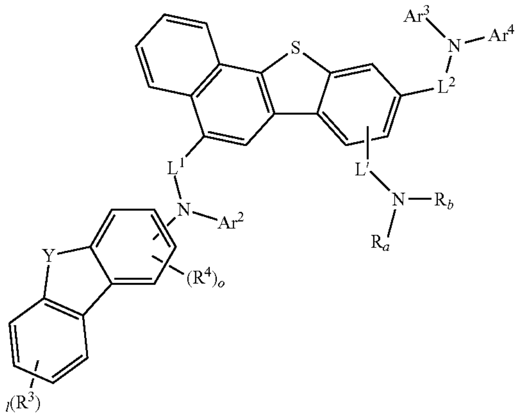

<Formula 7>

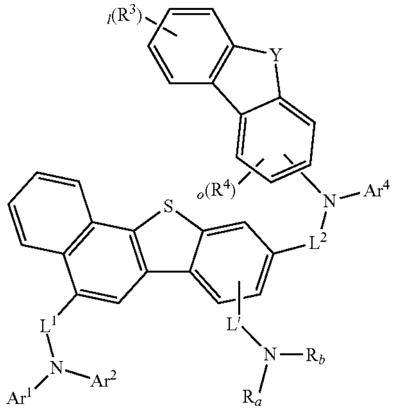

In Formulas 4 to 7, $Ar^1$ to $Ar^4$, $R^1$, $R^3$, $R^4$, $R_a$, $R_b$, $L^2$, L', Y, l, n, o are the same as defined for Formula 1.

In addition, Formula 1 may be represented by one of Formula 8 to Formula 13.

<Formula 8>
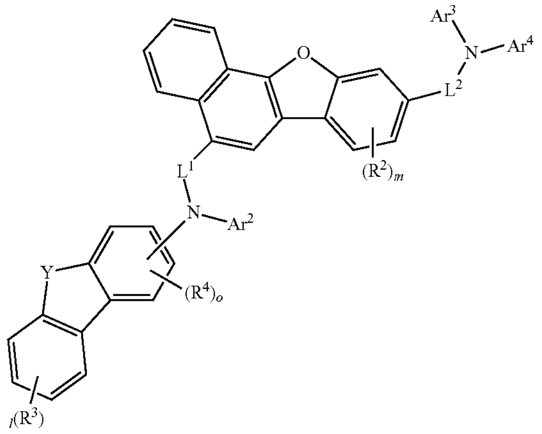
<Formula 9>
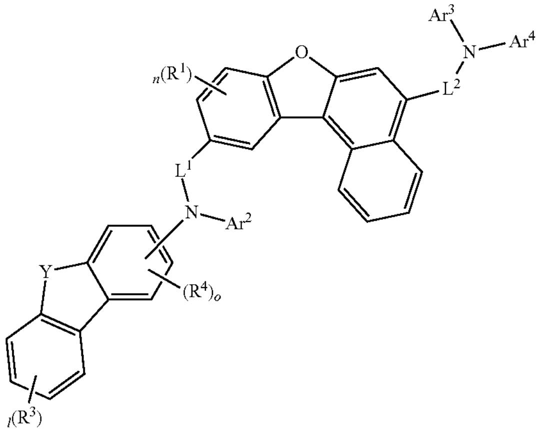
<Formula 10>
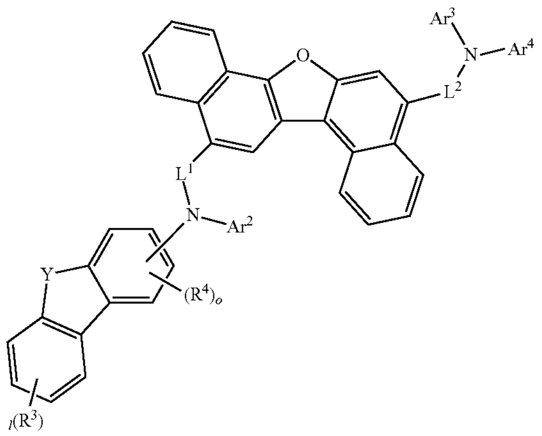
-continued
<Formula 11>
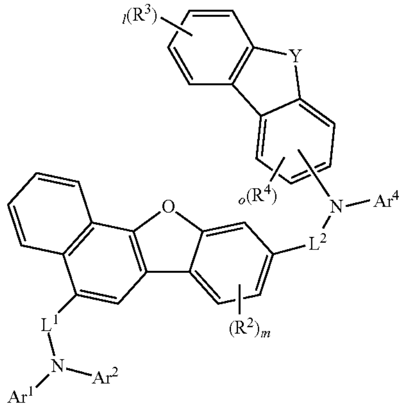
<Formula 12>
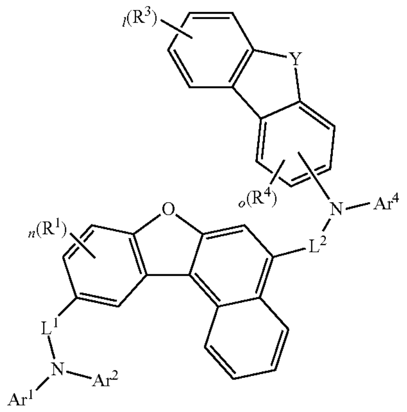
<Formula 13>
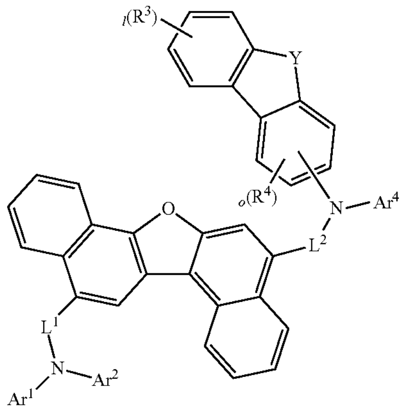
In Formulas 8 to 13, $Ar^1$ to $Ar^4$, $R^1$ to $R^4$, $L^1$, $L^2$, Y, l, m, n, o are the same as defined for Formula 1.
In addition, Formula 1 may be represented by Formula 14 or Formula 15.

<Formula 14>

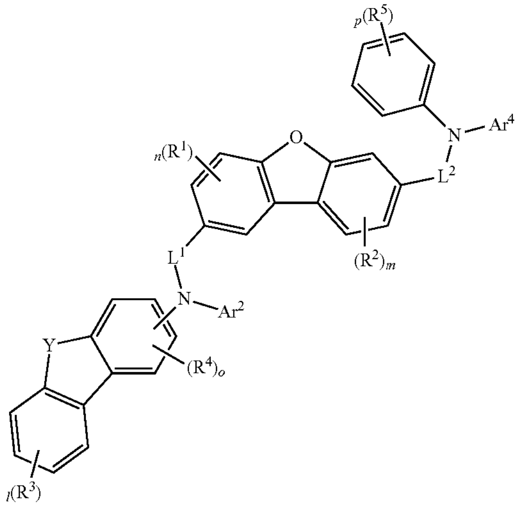

<Formula 15>

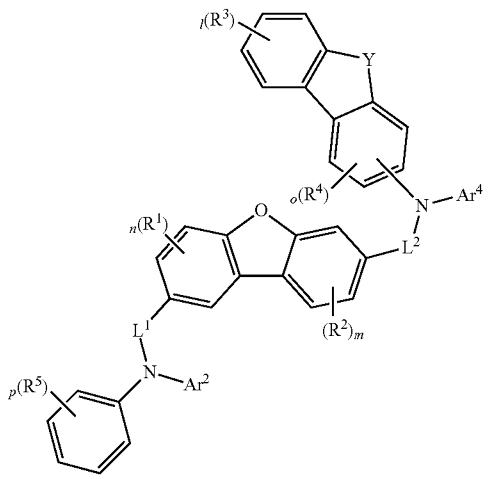

In Formulas 14 and 15, Are, $Ar^4$, $R^1$ to $R^4$, $L^1$, $L^2$, Y, l, m, n, o are the same as defined for Formula 1.

$R^5$ is each independently selected from the group consisting of hydrogen, deuterium, halogen, a $C_6$-$C_{20}$ aryl group, a fluorenyl group, a $C_2$-$C_{20}$ heterocyclic group containing at least one heteroatom of O, N, S, Si, and P, a $C_3$-$C_{20}$ aliphatic ring, a $C_1$-$C_{20}$ alkyl group, a $C_2$-$C_{10}$ alkenyl group, a $C_2$-$C_{10}$ alkynyl group, a $C_1$-$C_{10}$ alkoxyl group, a $C_6$-$C_{10}$ aryloxy group and -L'-N($R_a$)($R_b$).

In addition, adjacent $R^5$s together may be bonded to each other to form a ring, for example, the ring may be selected from the group consisting of a $C_6$-$C_{60}$ aromatic hydrocarbon, a $C_2$-$C_{60}$ heterocyclic group containing at least one heteroatom of O, N, S, Si, and P, a $C_3$-$C_{60}$ aliphatic ring and a combination thereof.

p is an integer of 0 to 5, and when p is an integer of 2 or more, each of a plurality of $R^5$s is the same or different from each other.

Specifically, the compound represented by formula 1 may be one of the following compounds, but there is no limitation thereto.

P-1

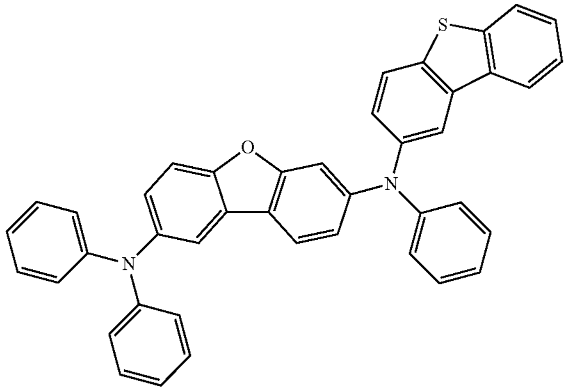

P-2

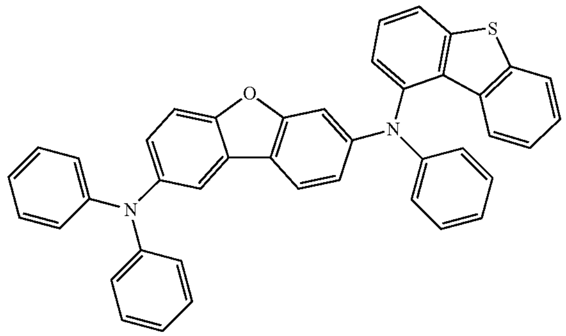

P-3

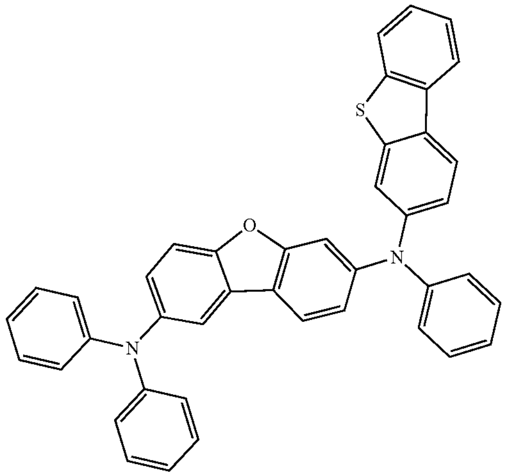

P-4

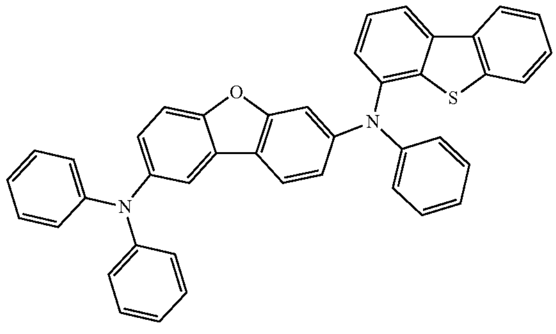

-continued
P-5
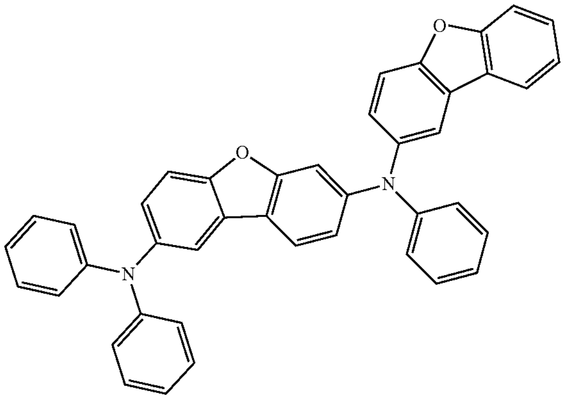
P-6
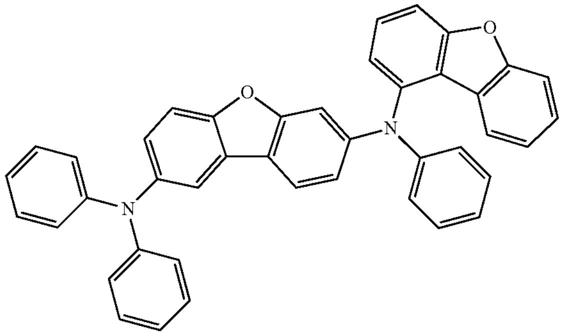
P-7
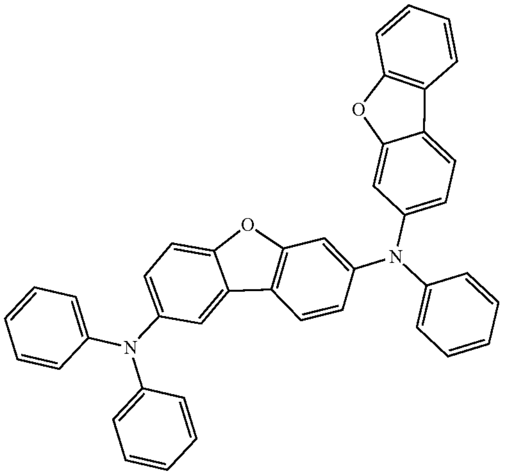
P-8
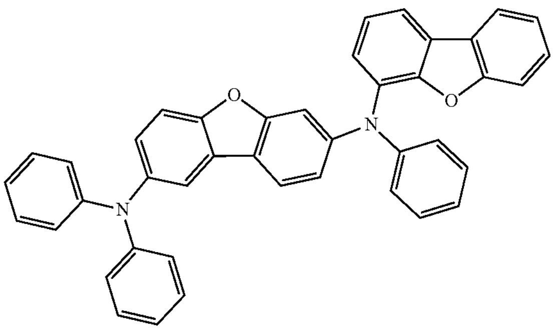
-continued
P-9
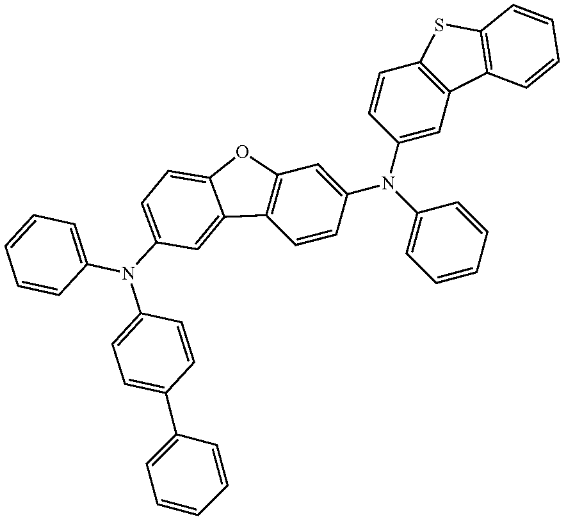
P-10
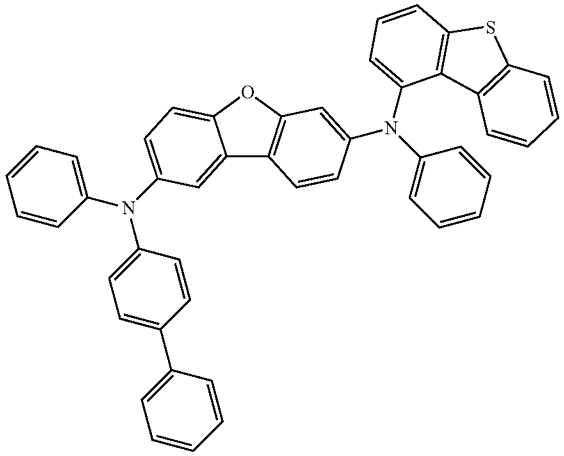
P-11
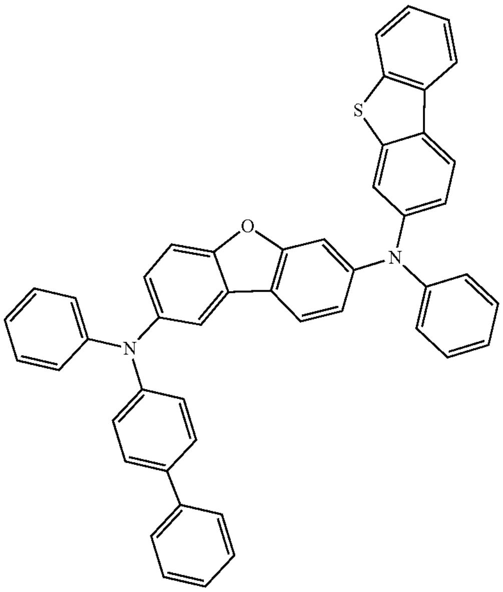

-continued
P-12
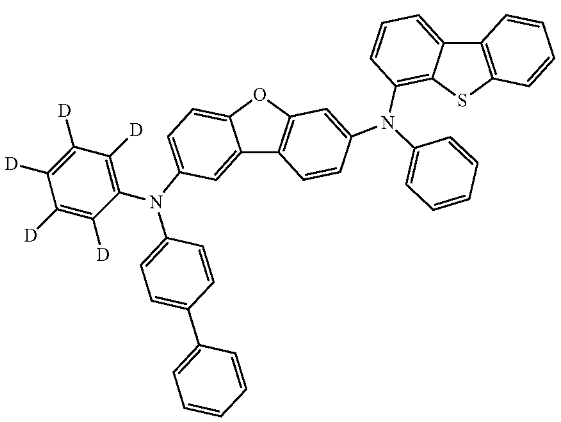
P-13
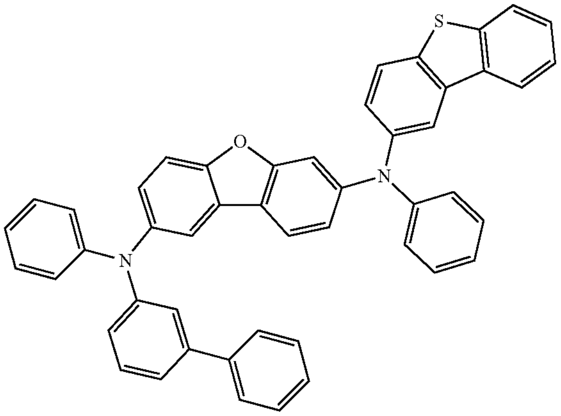
P-14
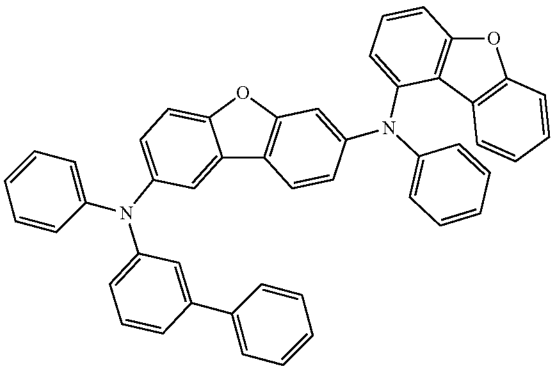
-continued
P-15
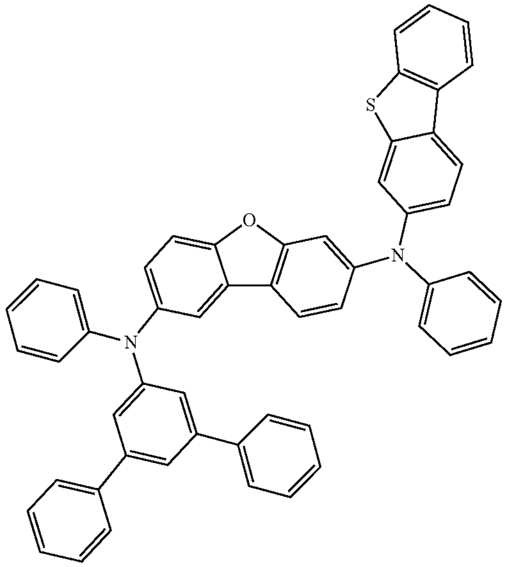
P-16
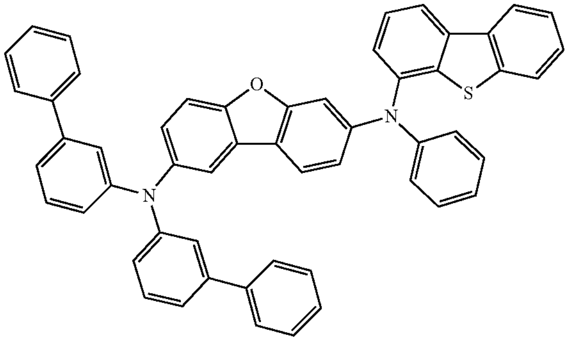
P-17
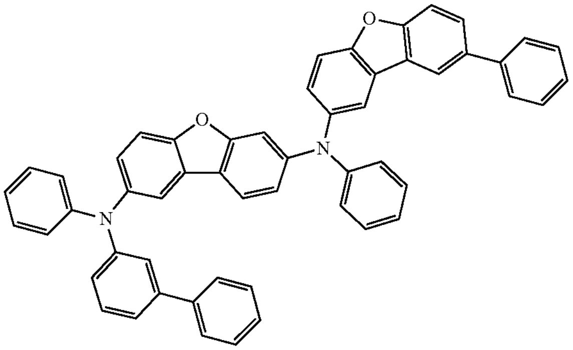

-continued
P-18
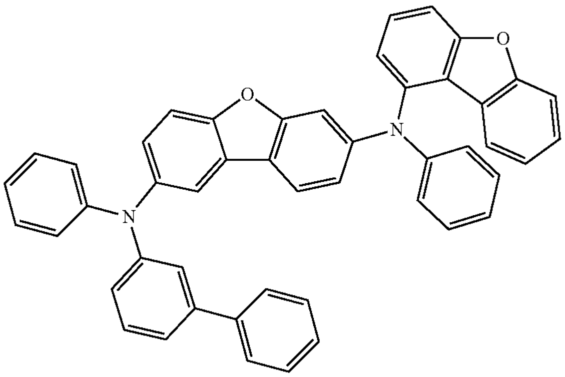
P-19
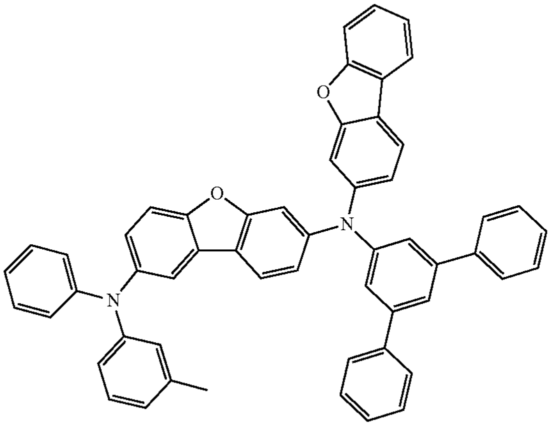
P-20
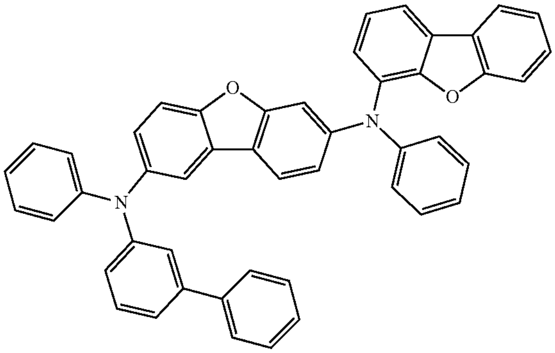
P-21
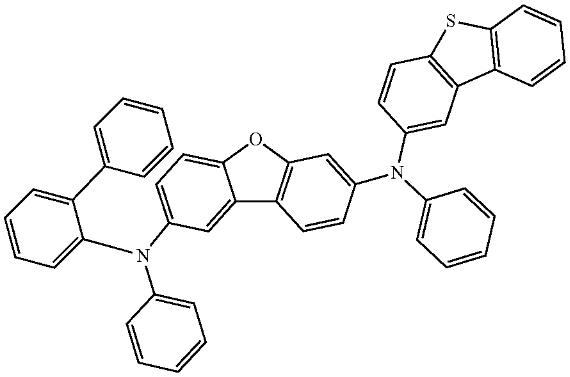
-continued
P-22
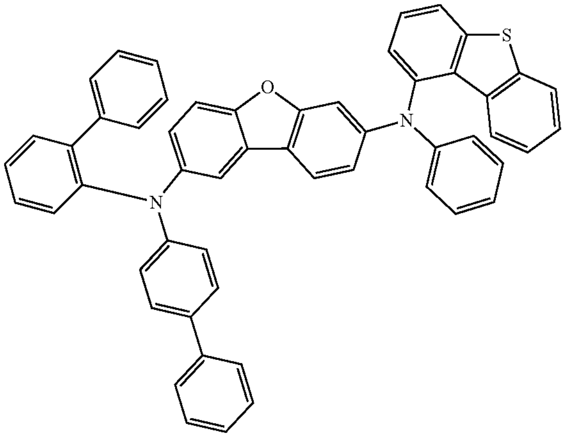
P-23
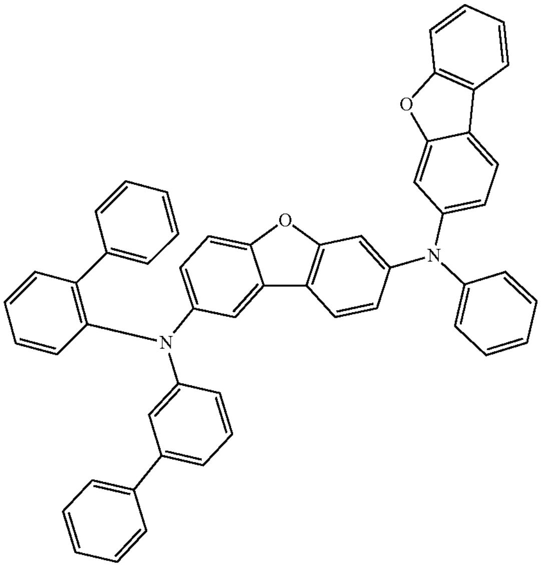
P-24
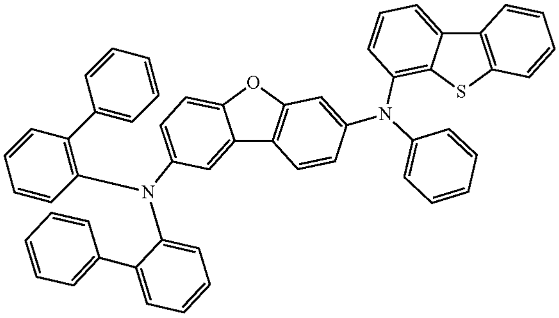

-continued
P-25
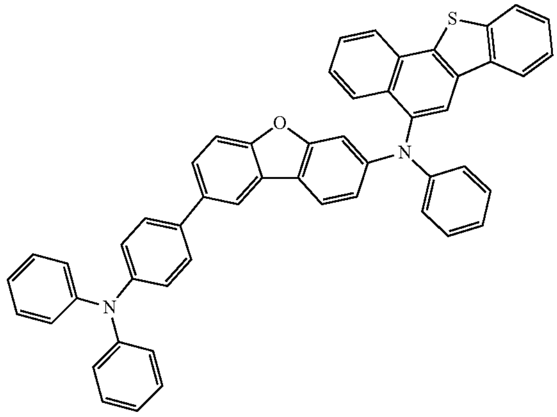
P-26
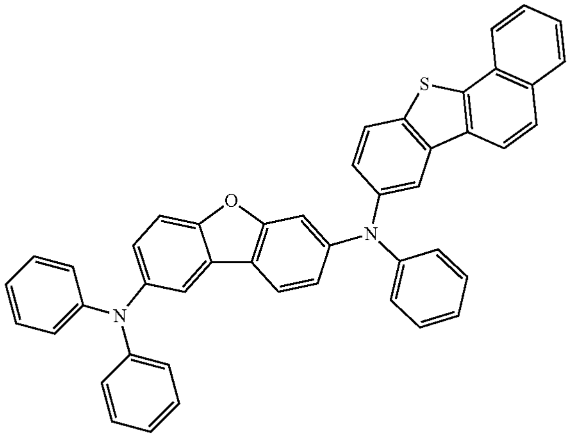
P-27
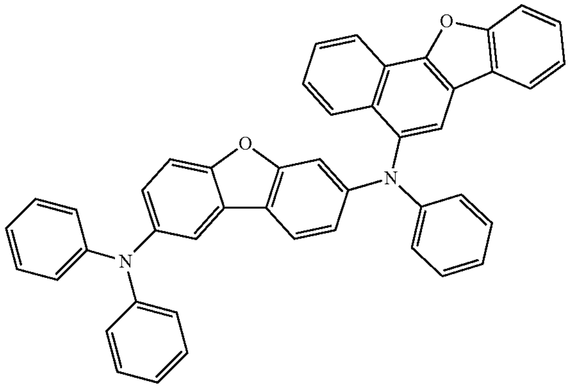
-continued
P-28
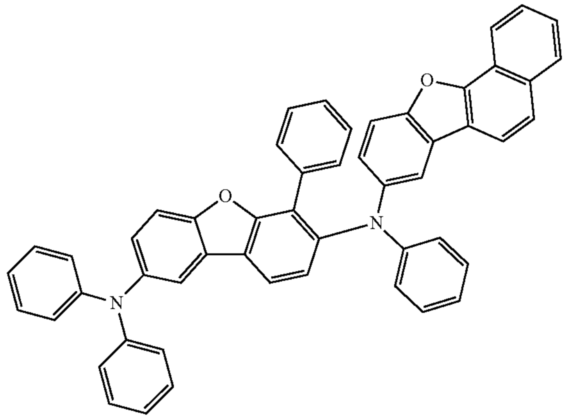
P-29
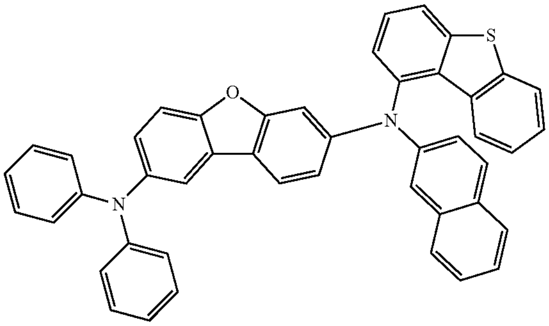
P-30
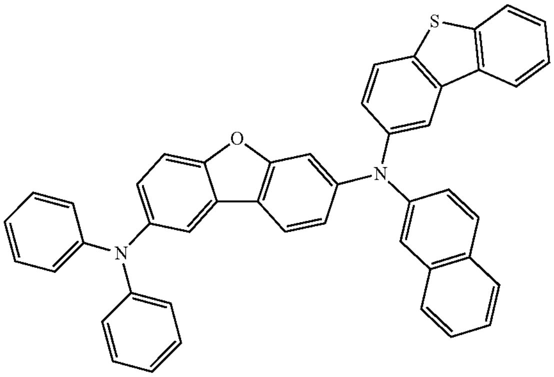
P-31
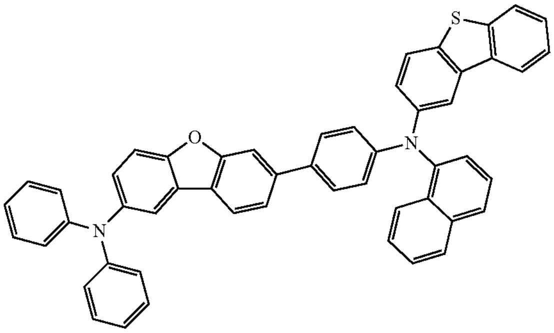

-continued
P-32
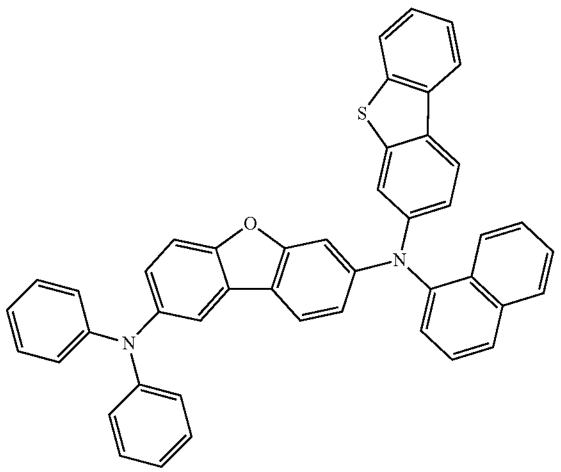
P-33
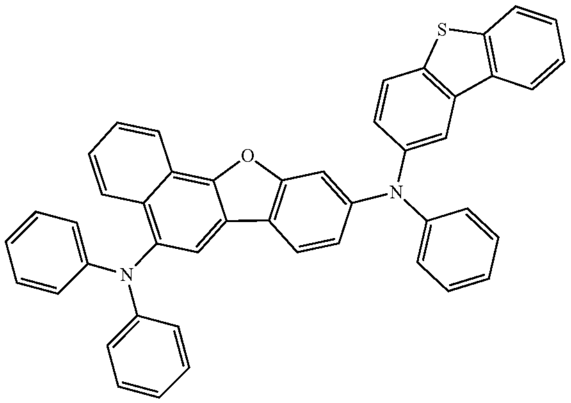
P-34
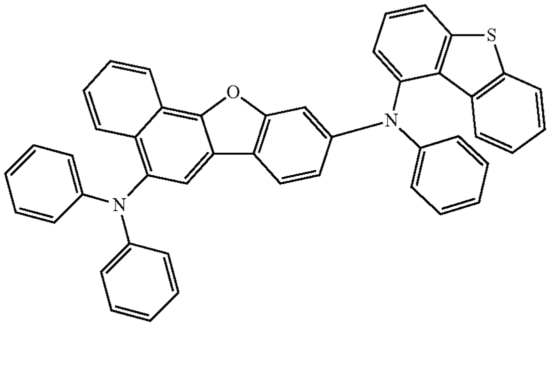
-continued
P-35
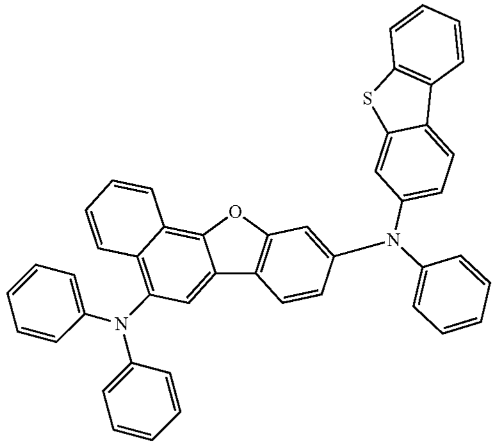
P-36
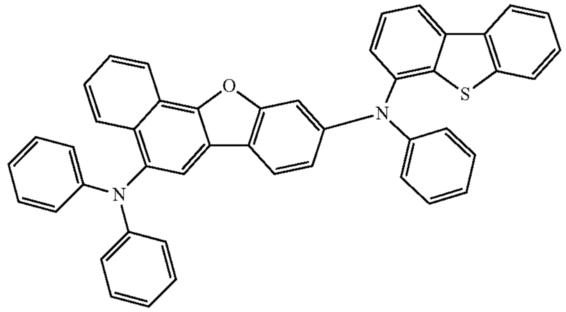
P-37
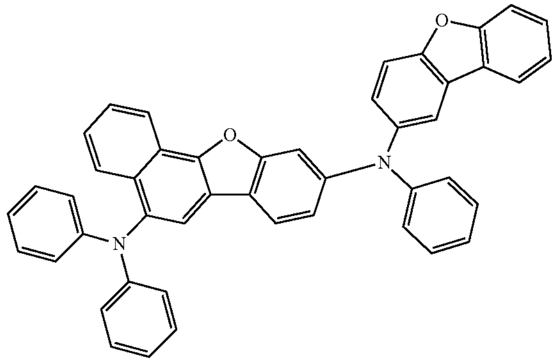
P-38
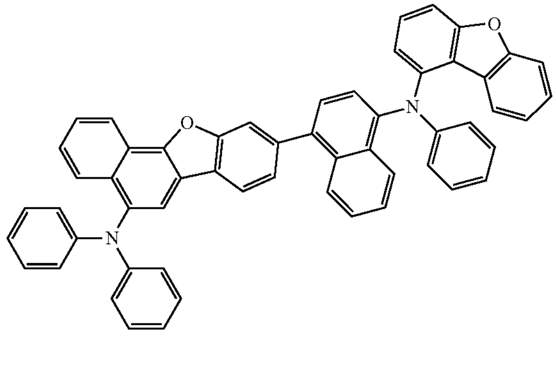

-continued
P-39
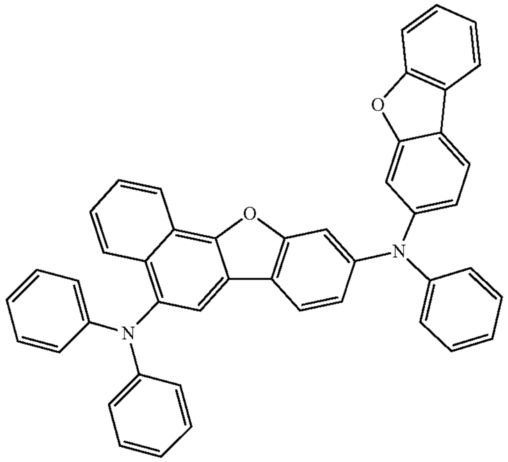
P-40
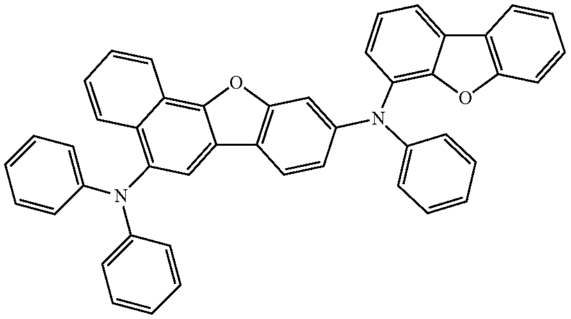
P-41
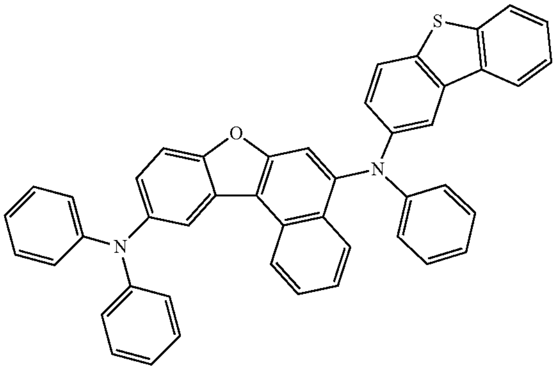
P-42
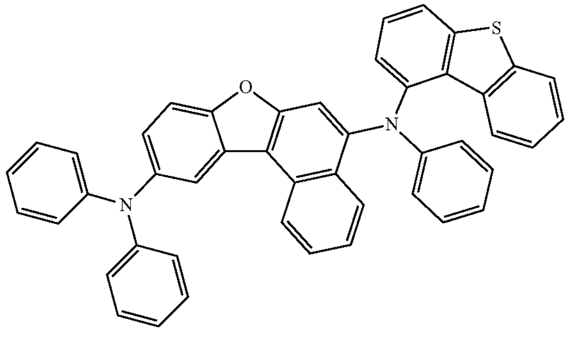
-continued
P-43
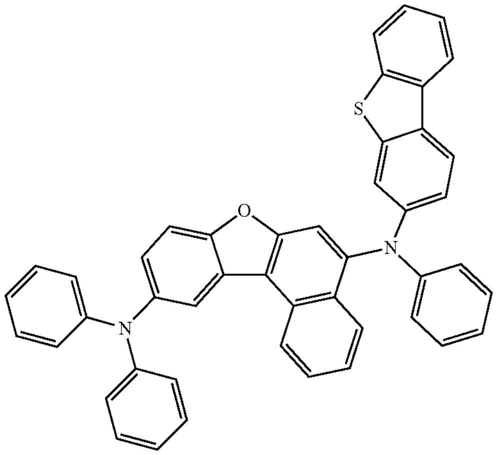
P-44
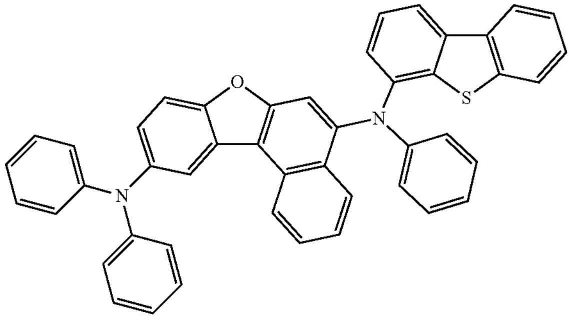
P-45
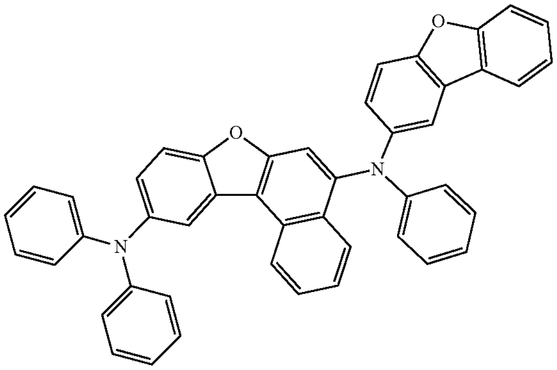
P-46
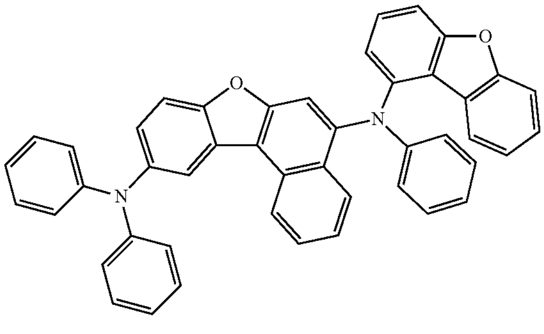

-continued
P-47
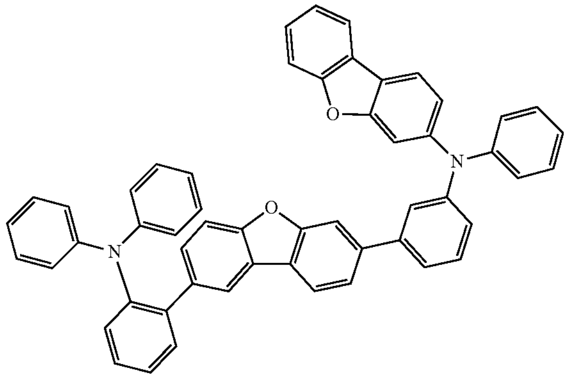
P-48
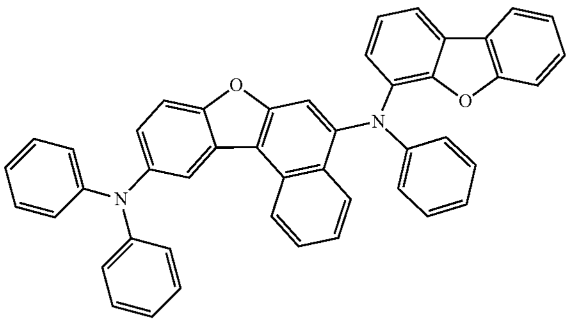
P-49
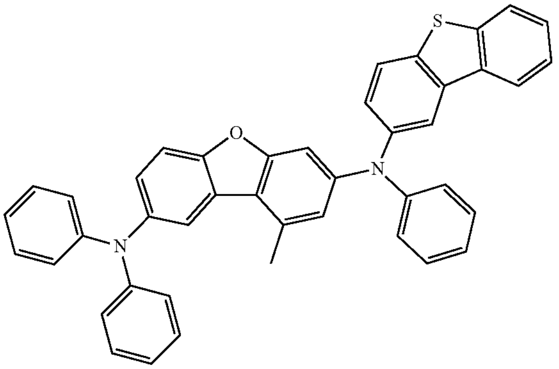
P-50
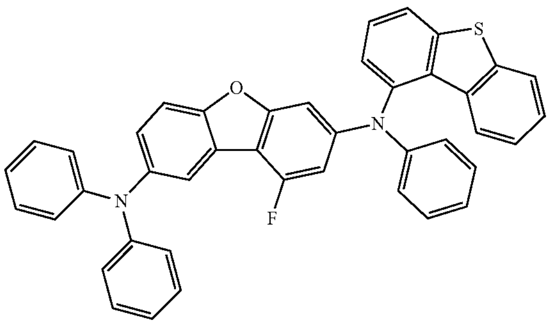
-continued
P-51
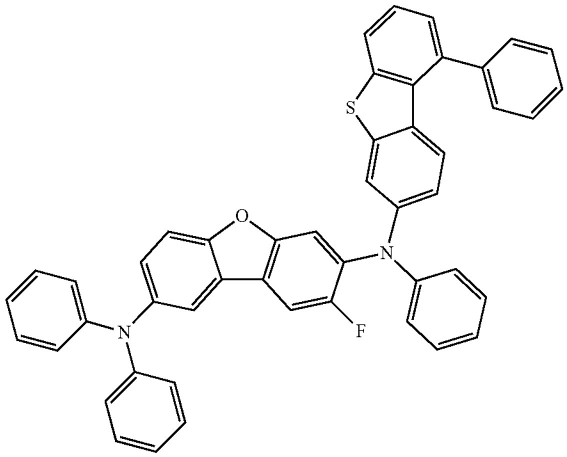
P-52
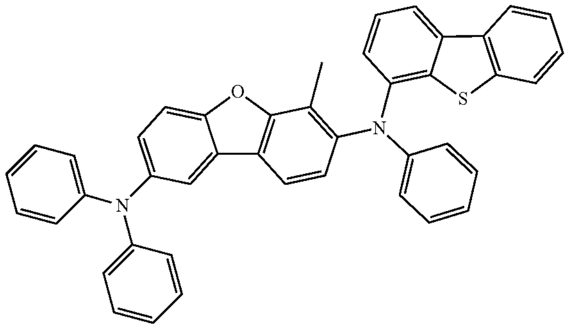
P-53
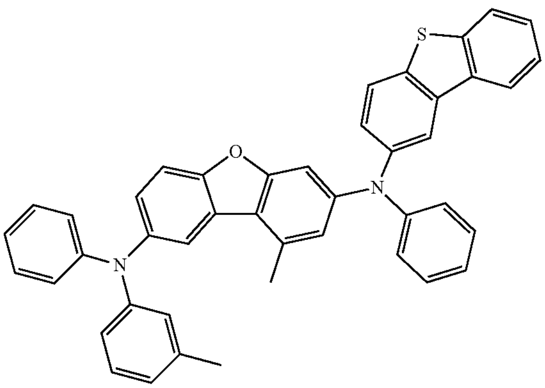
P-54
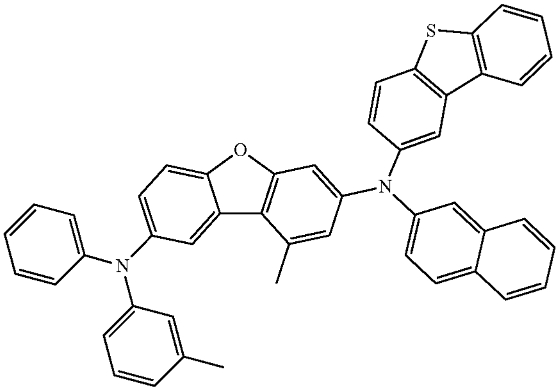

-continued
P-55
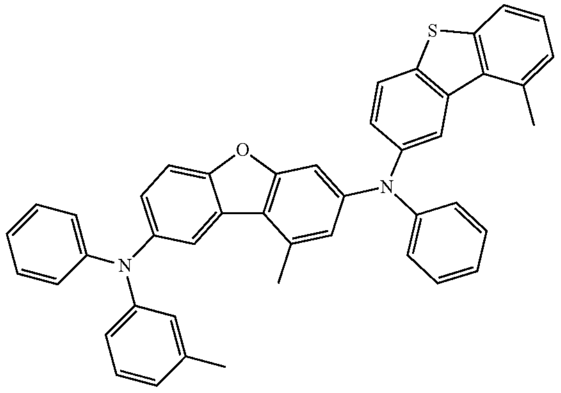
P-56
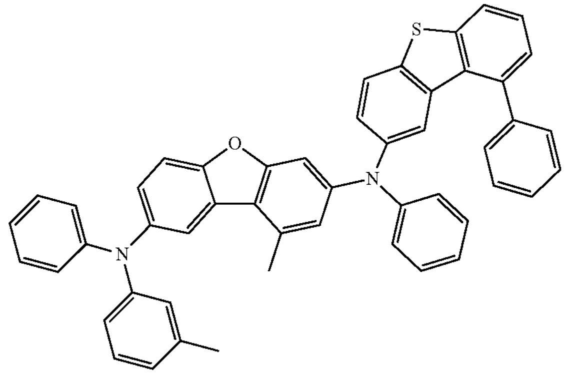
P-57
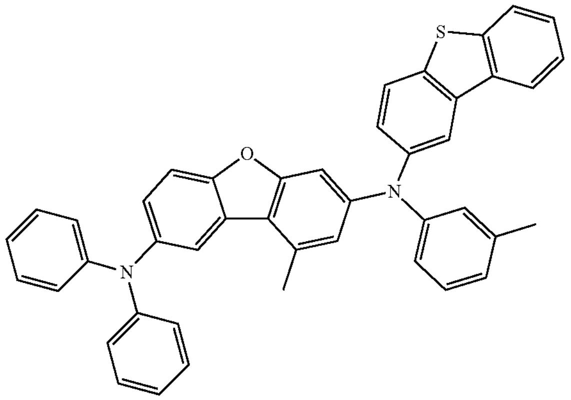
P-58
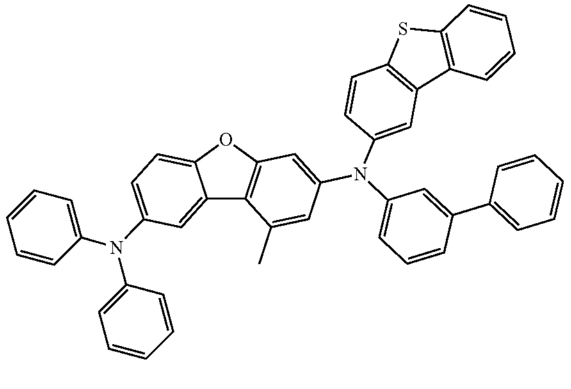
-continued
P-59
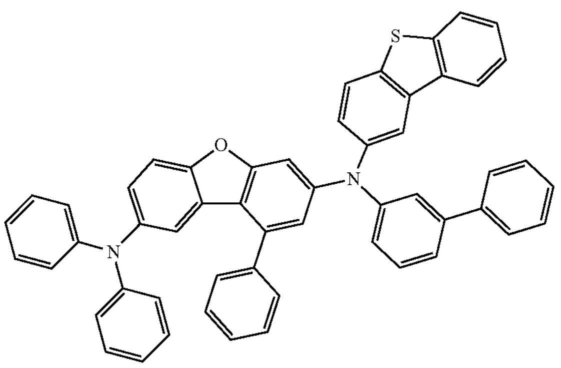
P-60
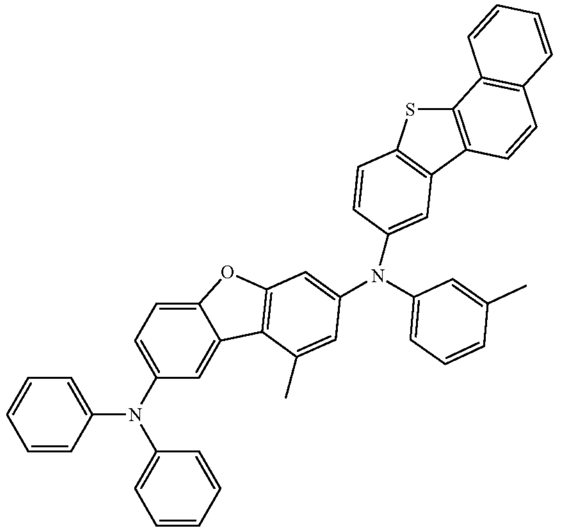
P-61
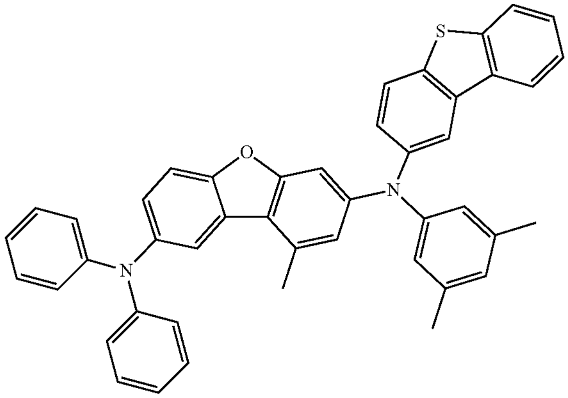

-continued
P-62
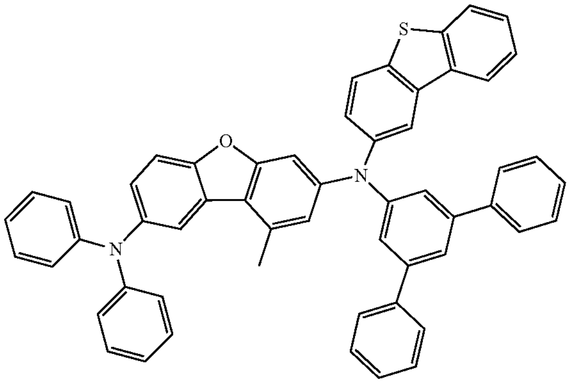
P-63
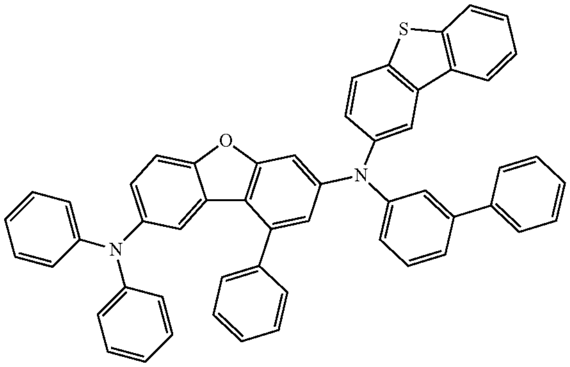
P-64
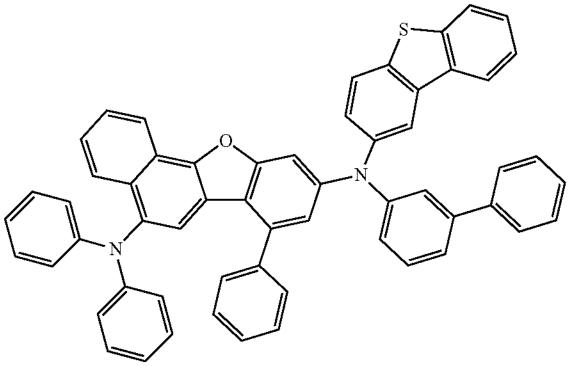
P-65
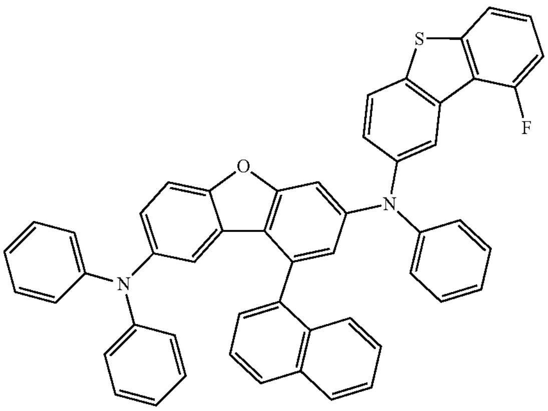
-continued
P-66
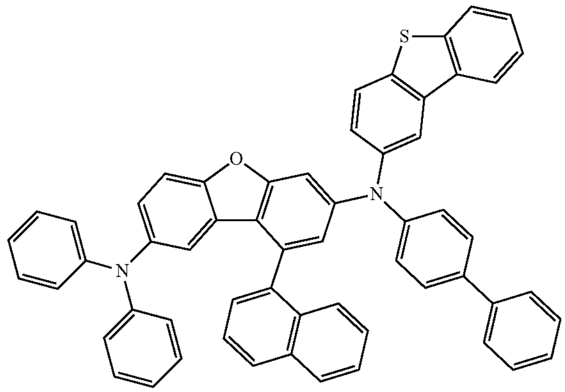
P-67
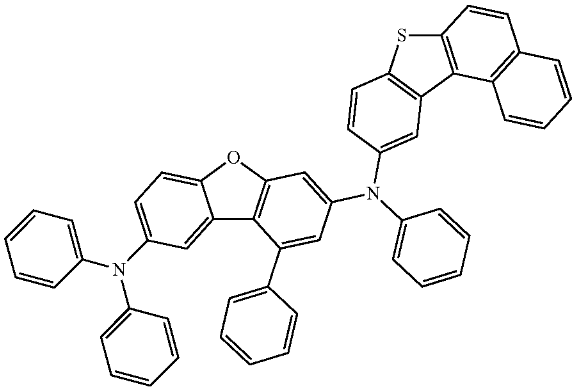
P-68
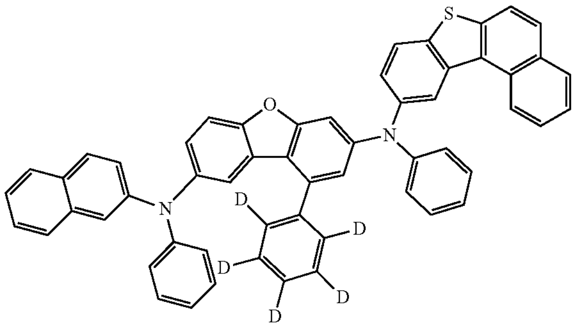
P-69
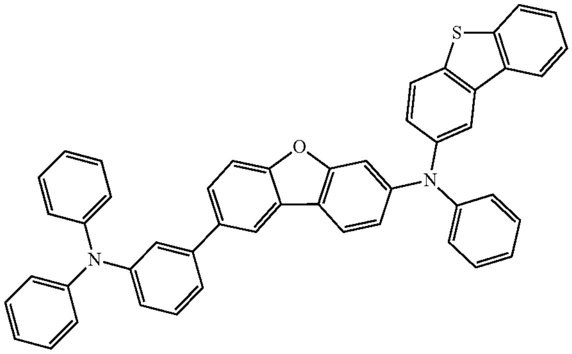

-continued
P-70
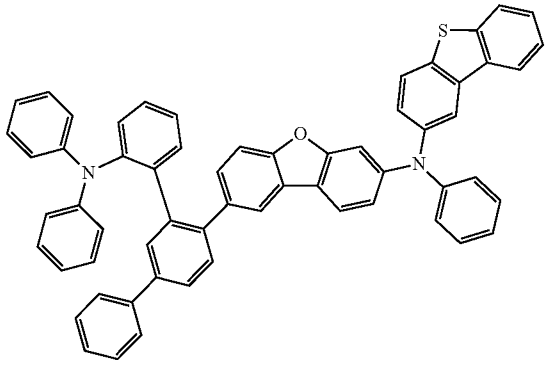
P-71
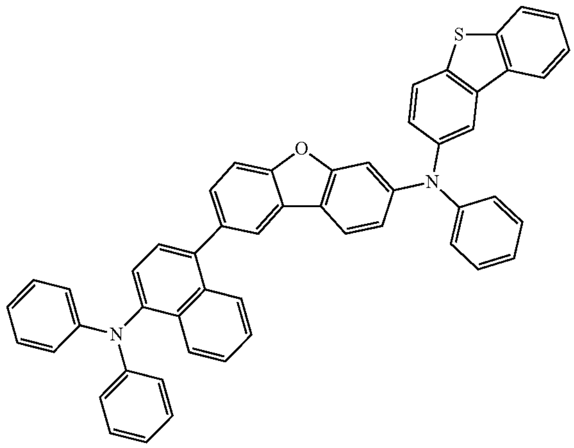
P-72
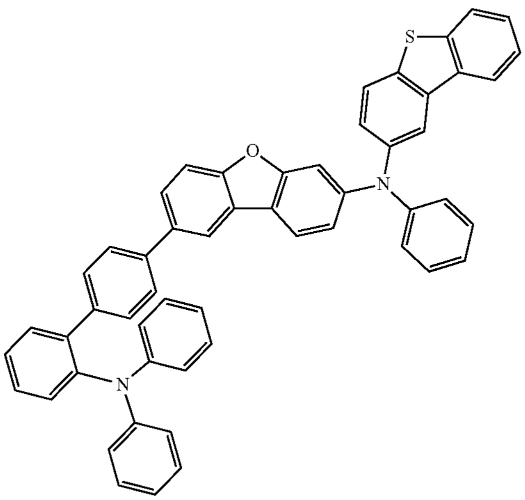
-continued
P-73
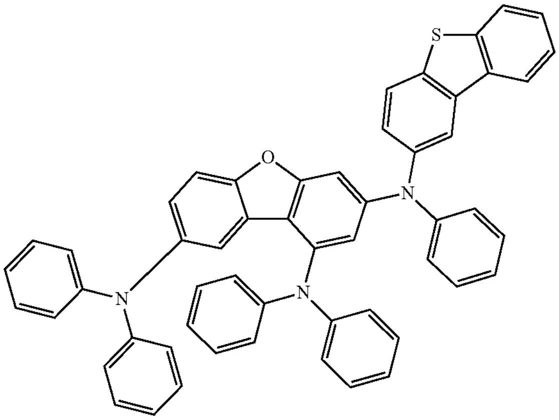
P-74
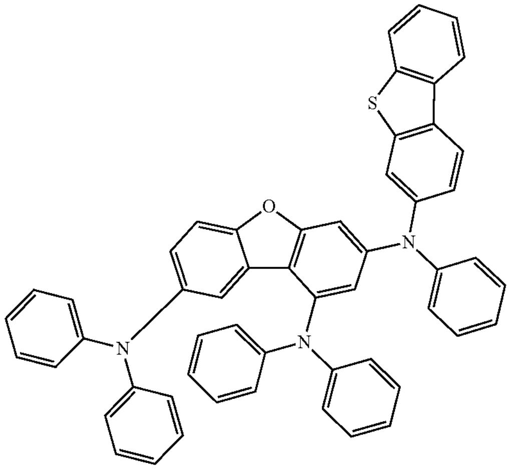
P-75
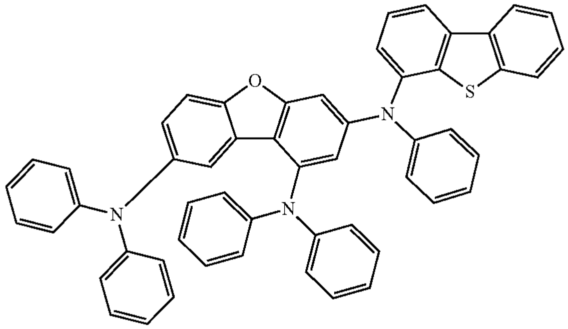
P-76
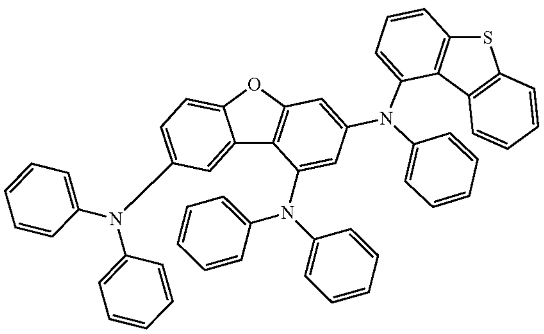

-continued
P-77
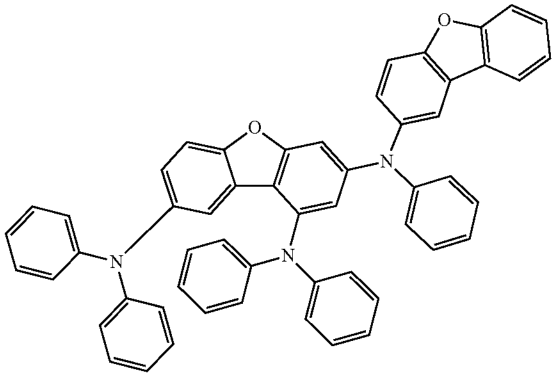
P-78
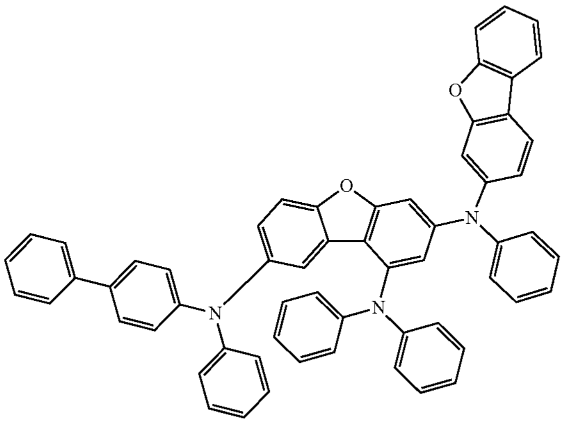
P-79
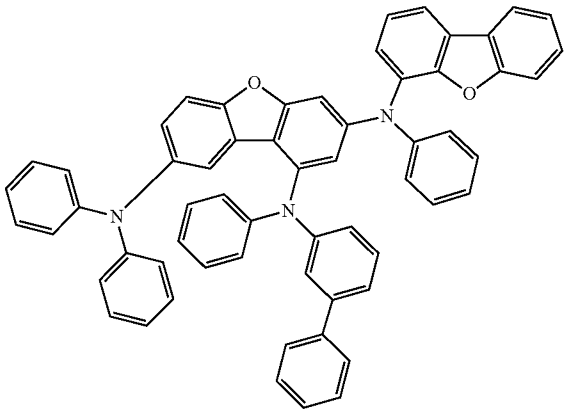
P-80
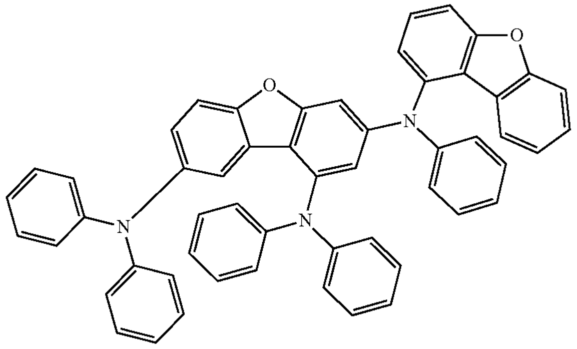
-continued
P-81
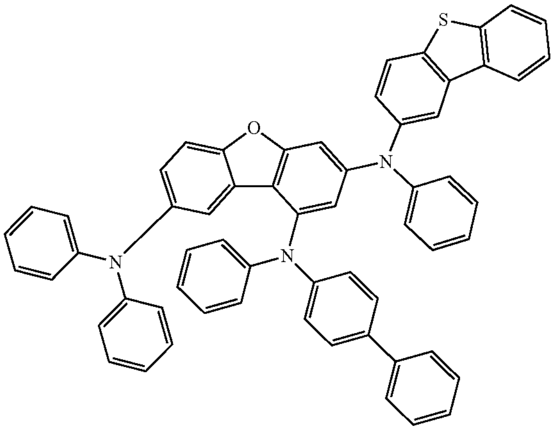
P-82
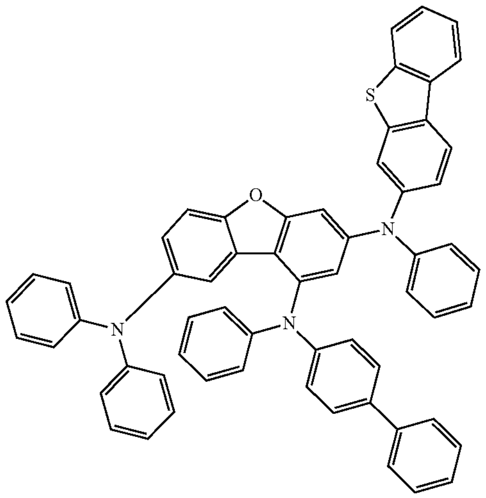
P-83
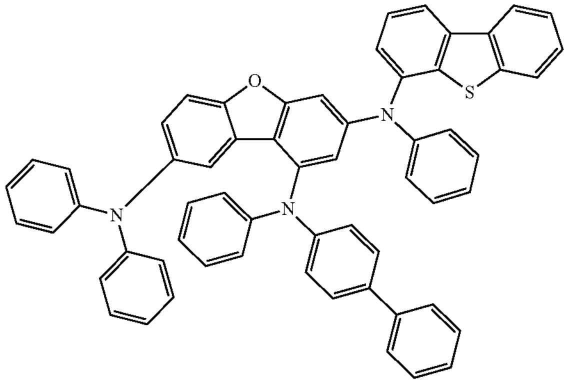

-continued
P-84
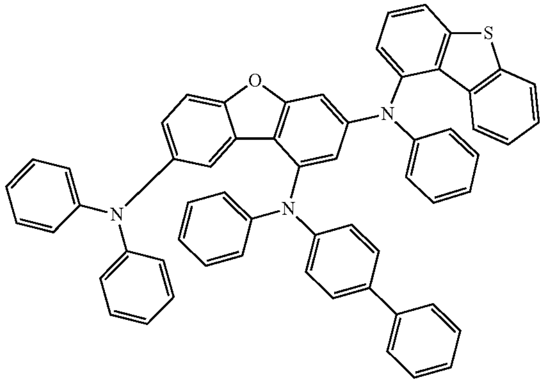
P-85
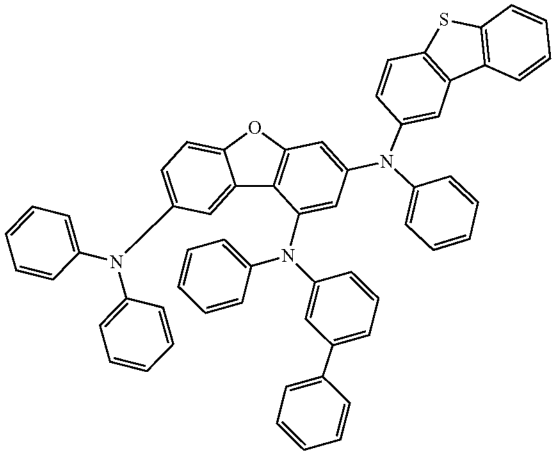
P-86
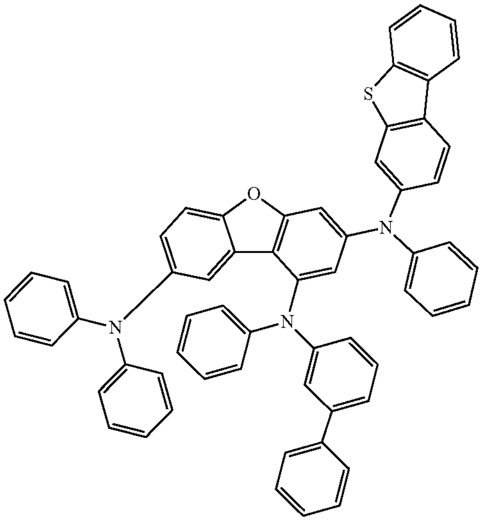
-continued
P-87
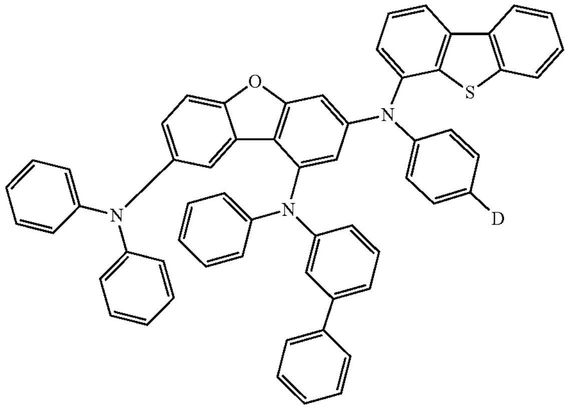
P-88
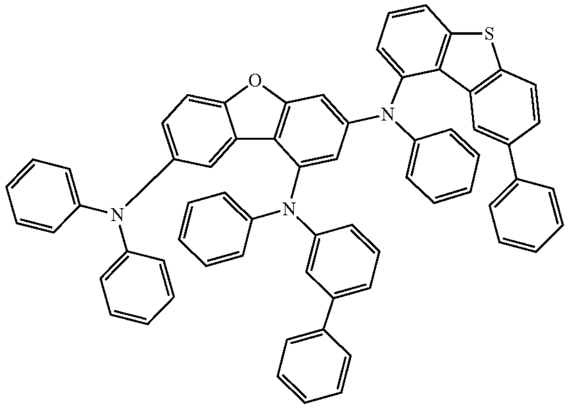
P-89
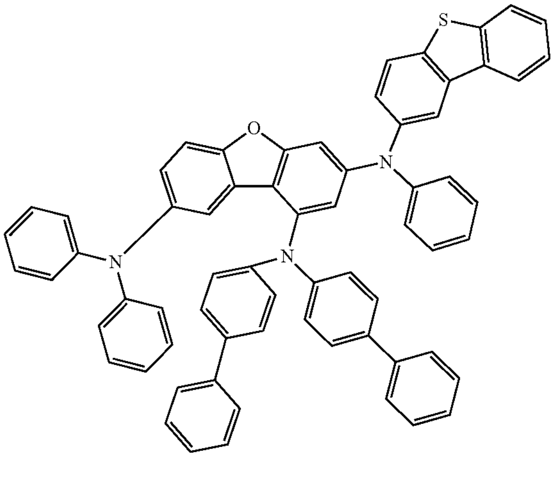

-continued
P-90
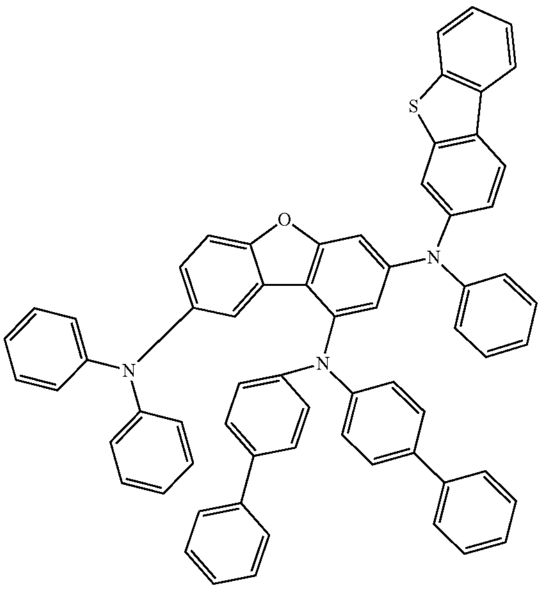
P-91
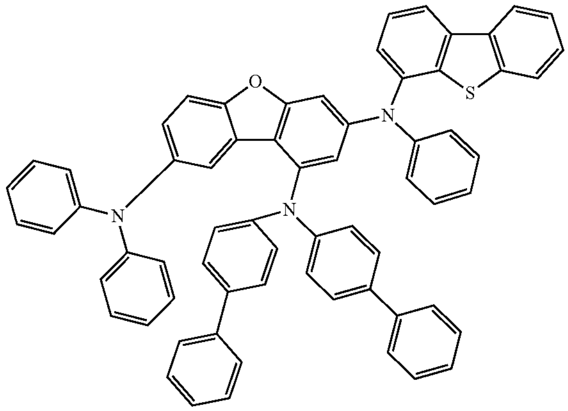
P-92
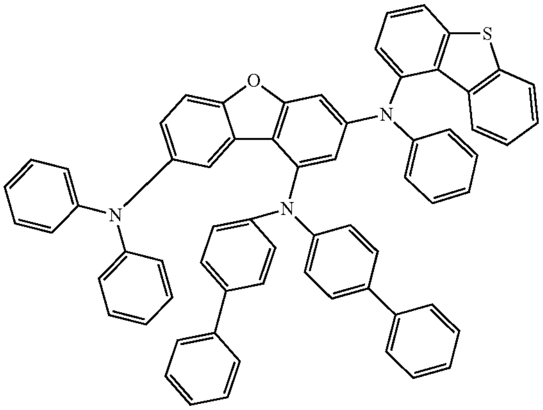
-continued
P-93
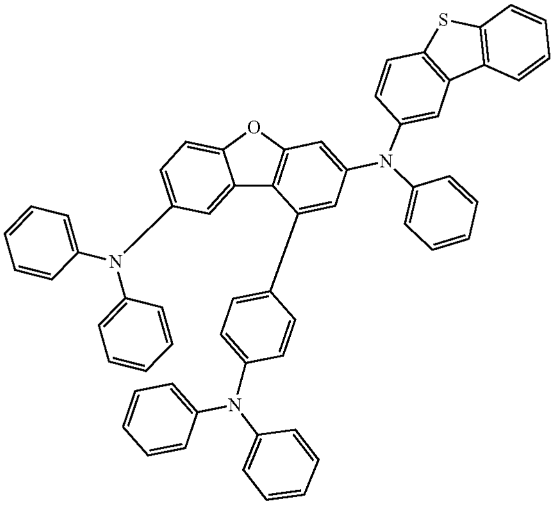
P-94
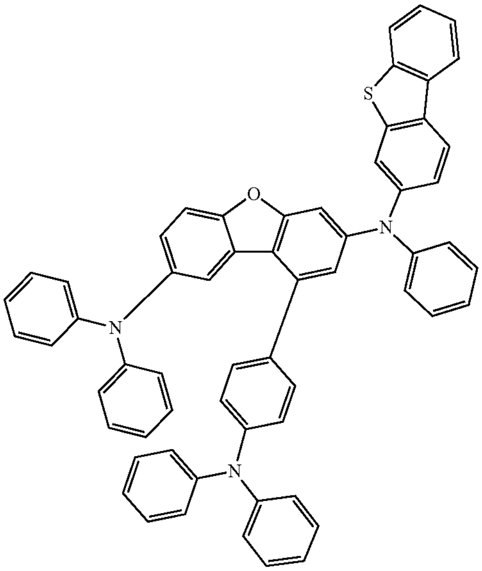
P-95
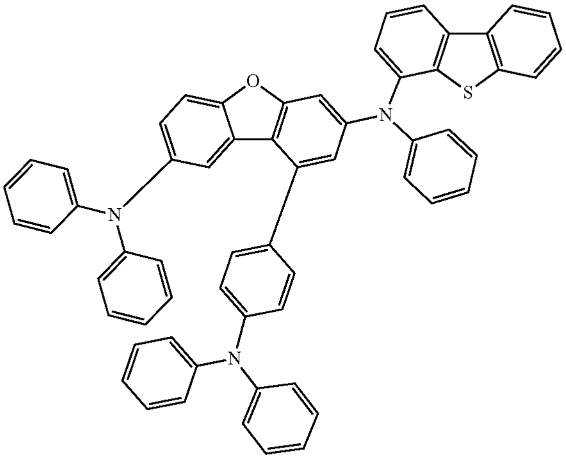

-continued
P-96
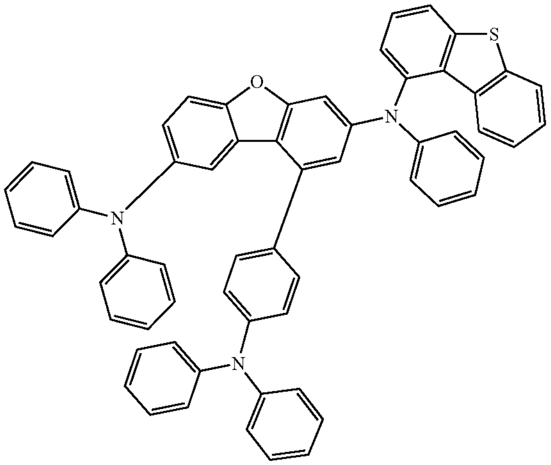
P-97
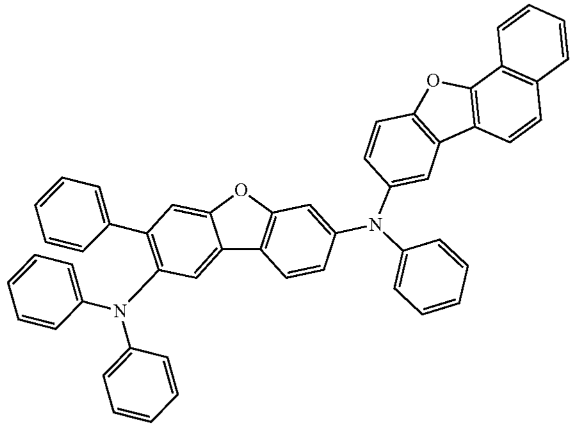
P-98
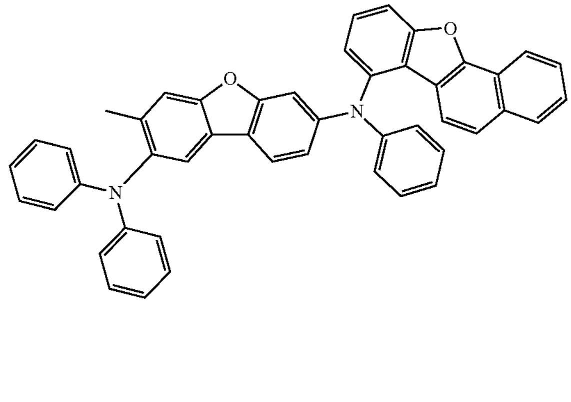
-continued
P-99
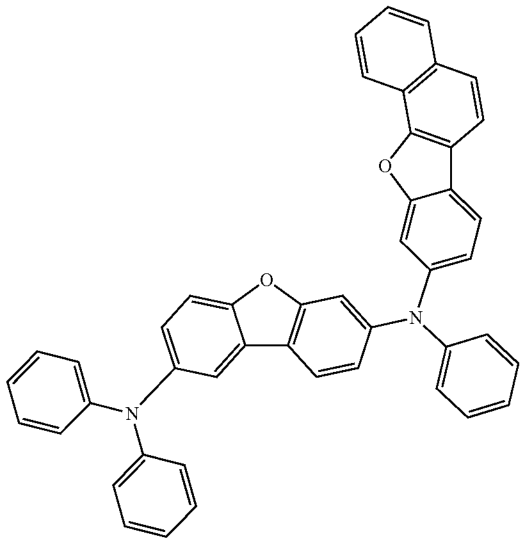
P-100
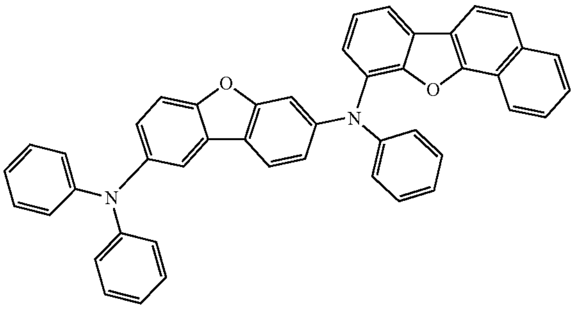
P-101
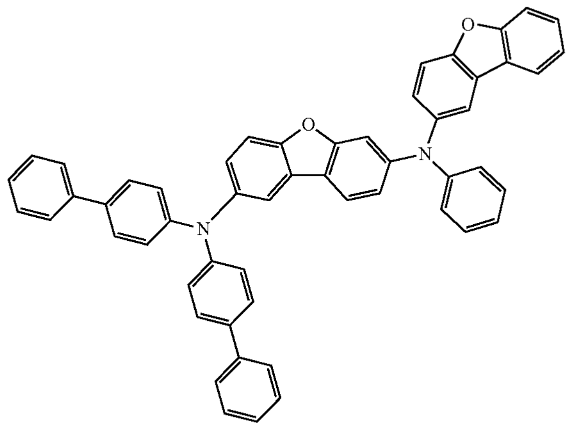

-continued
P-102
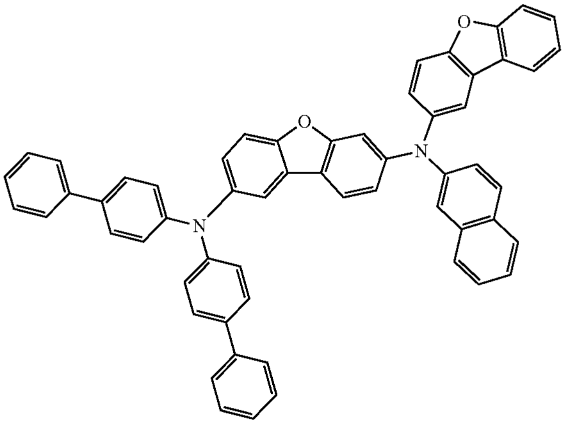
P-103
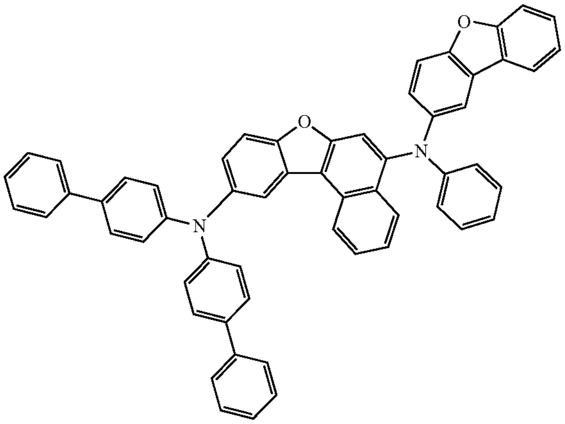
P-104
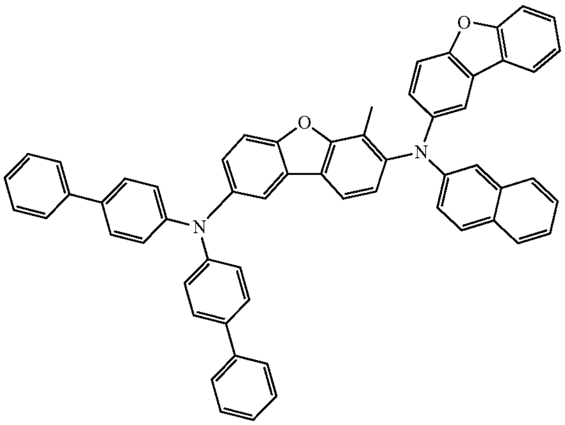
-continued
P-105
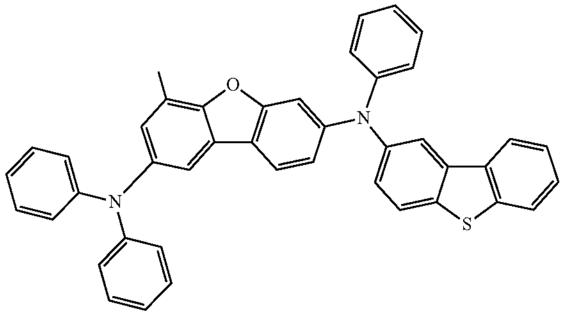
P-106
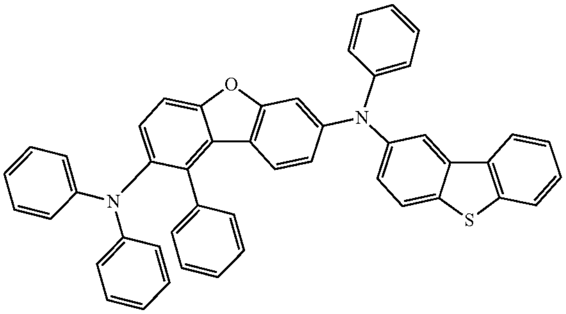
P-107
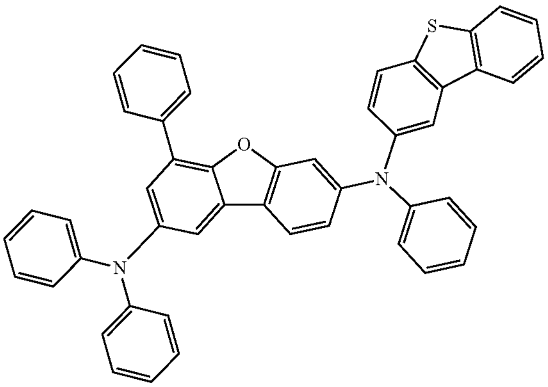
P-108
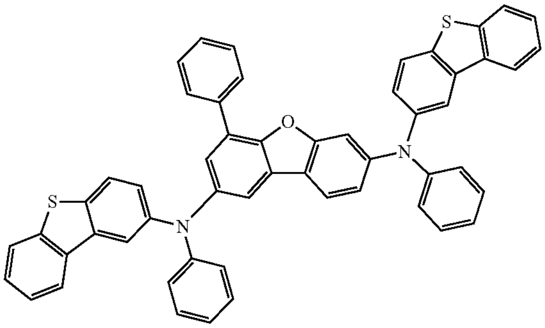

P-109
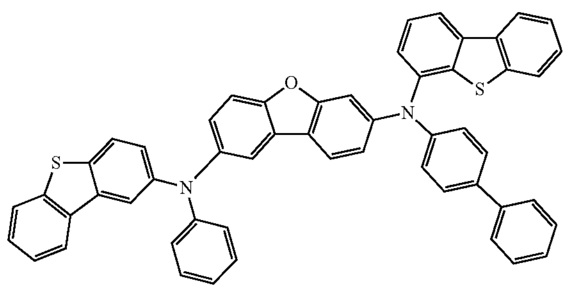
P-110
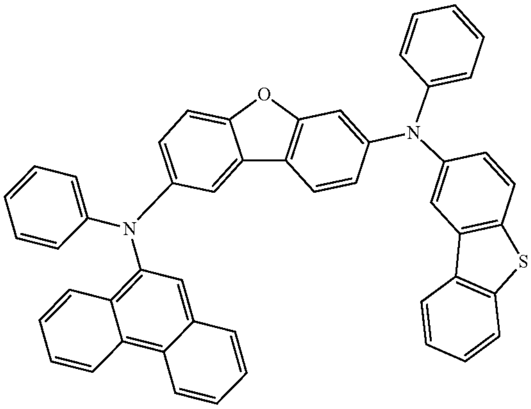
P-111
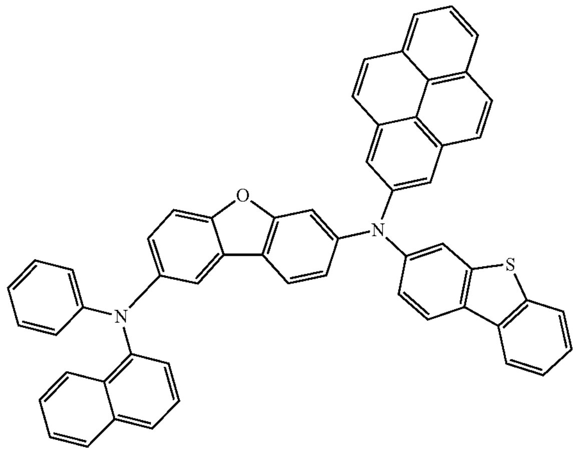
P-112
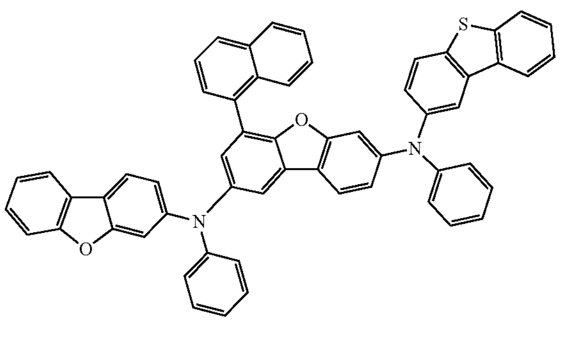
P-113
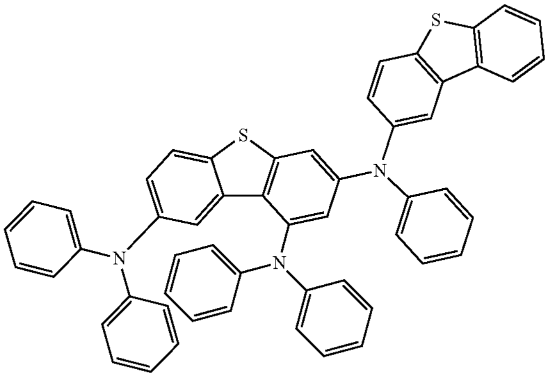
P-114
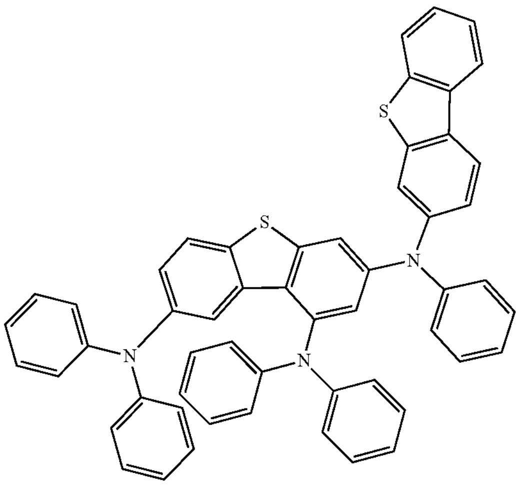
P-115
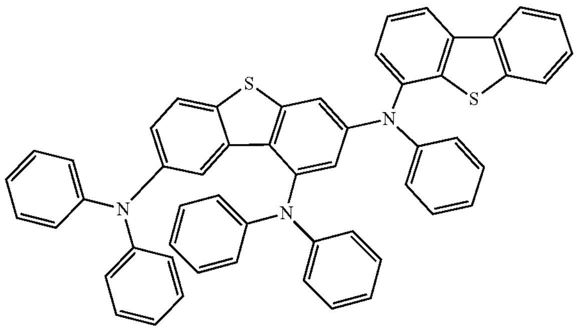
P-116
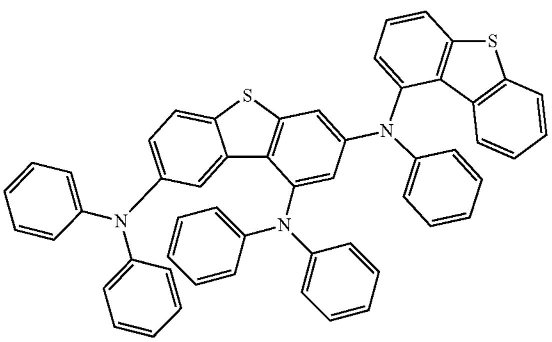

-continued
P-117
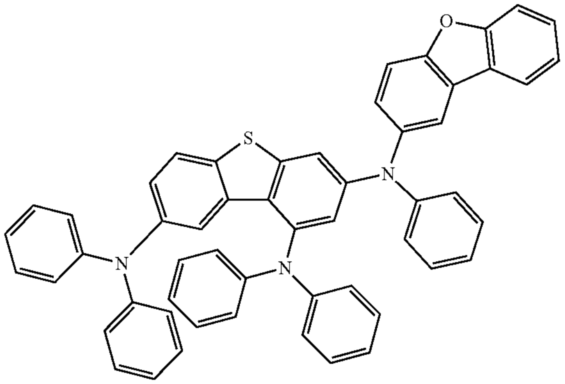
P-118
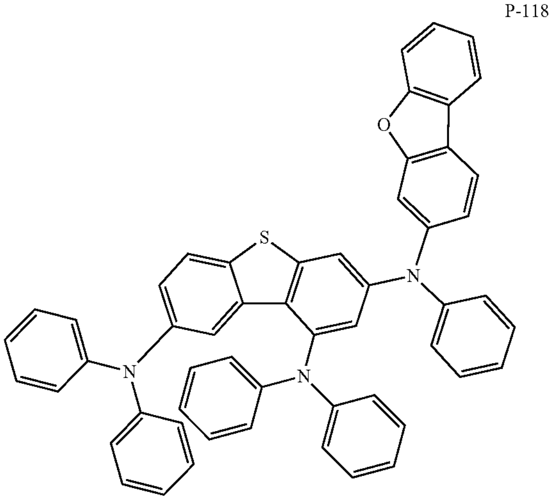
P-119
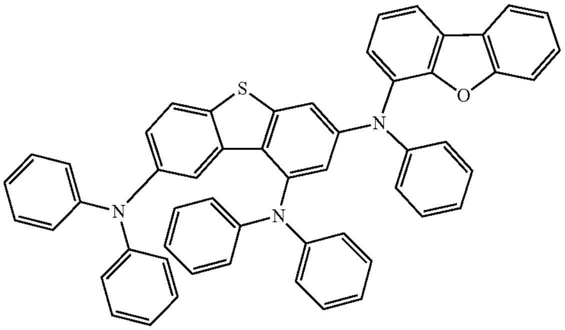
P-120
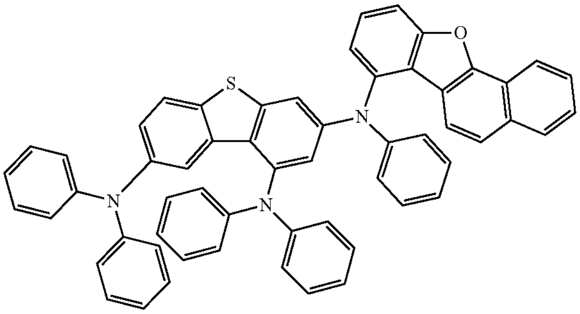
-continued
P-121
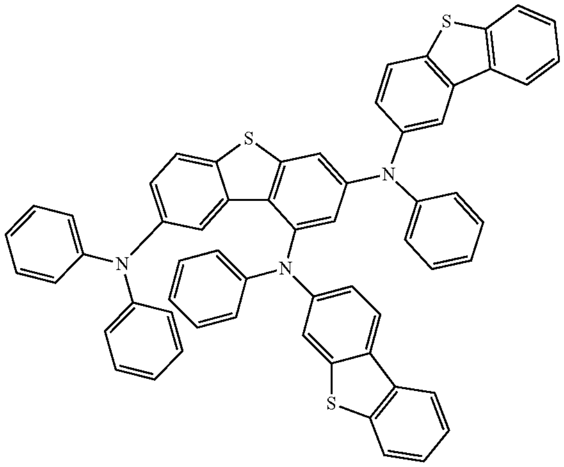
P-122
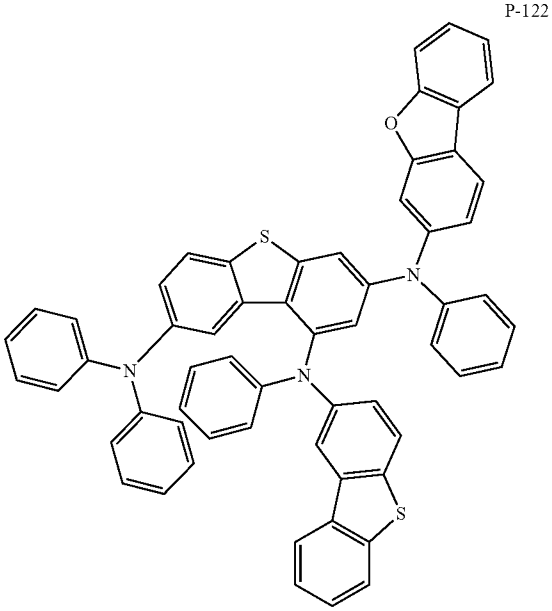
P-123
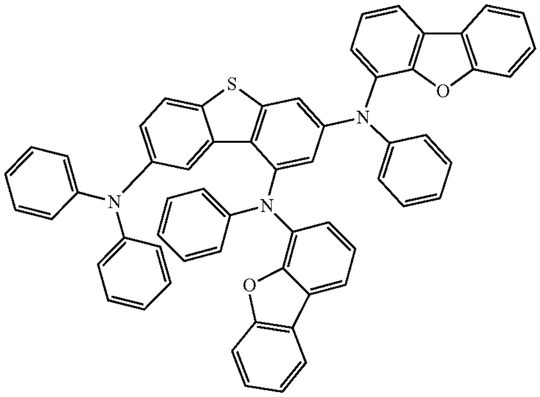

-continued
P-124
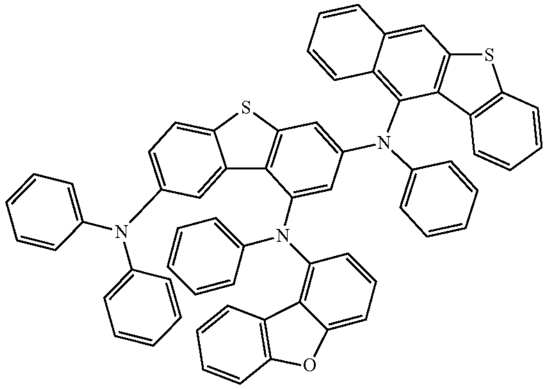
P-125
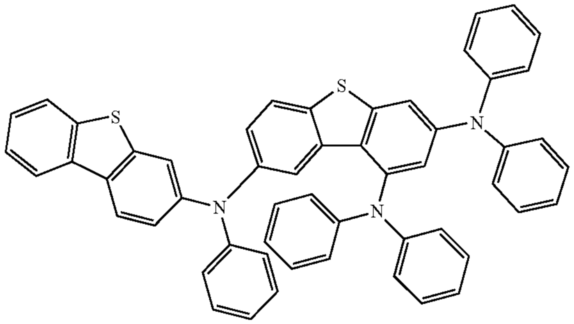
P-126
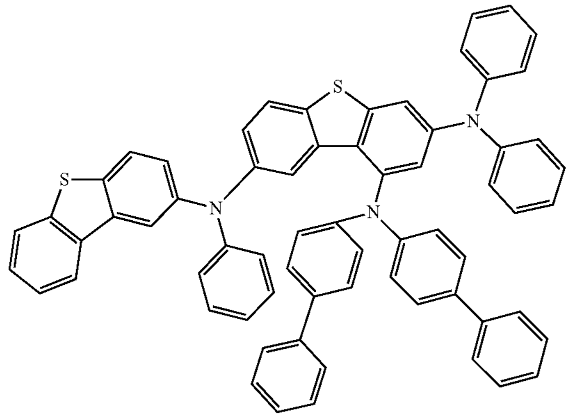
P-127
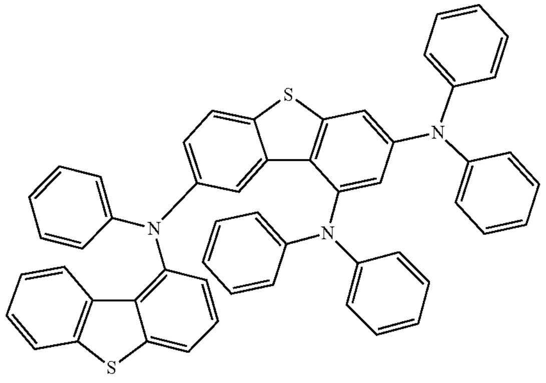
-continued
P-128
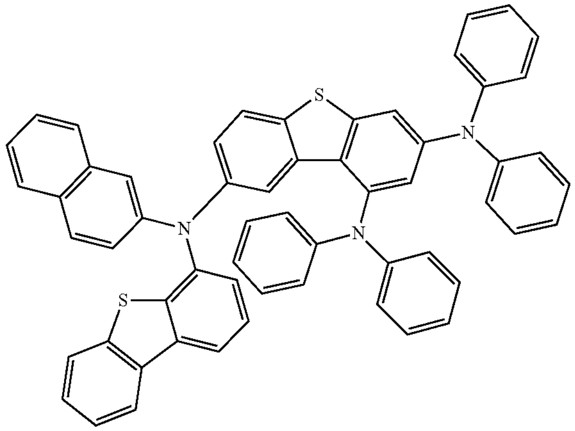
P-129
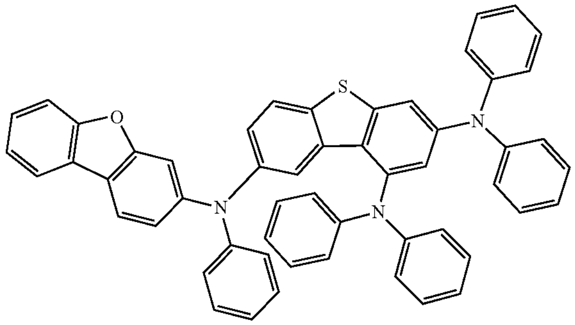
P-130
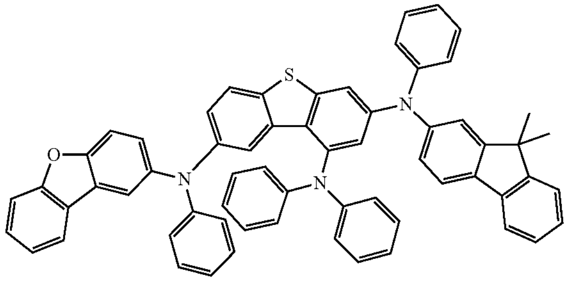
P-131
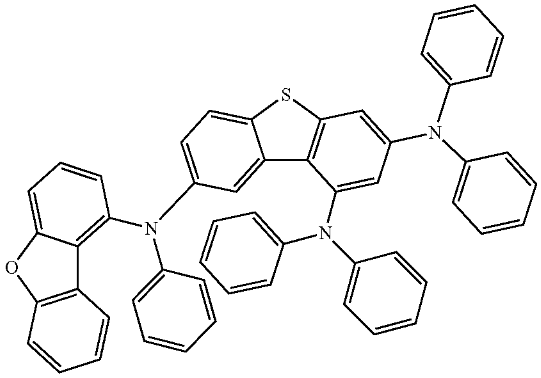

-continued
P-132
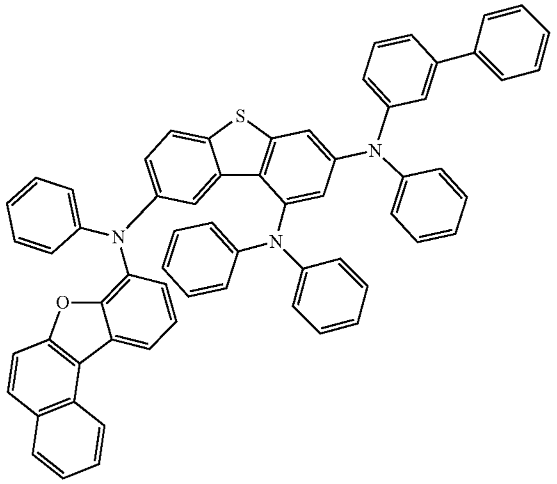
P-133
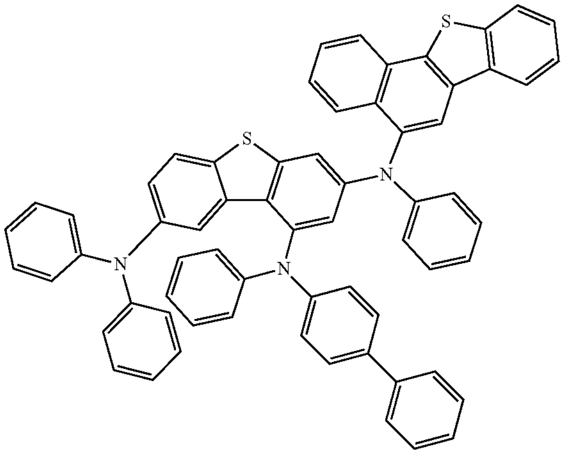
P-134
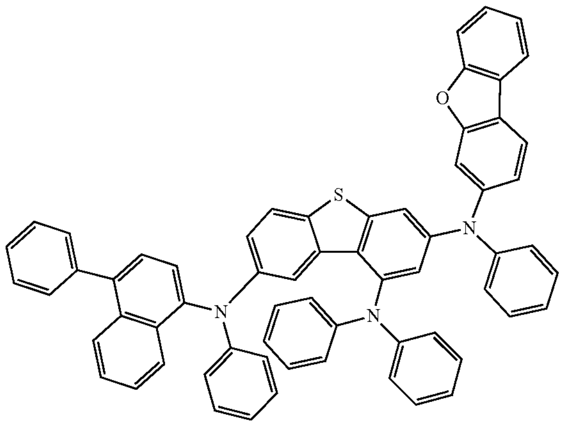
-continued
P-135
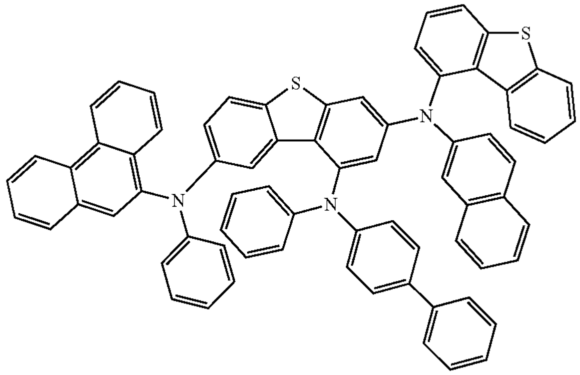
P-136
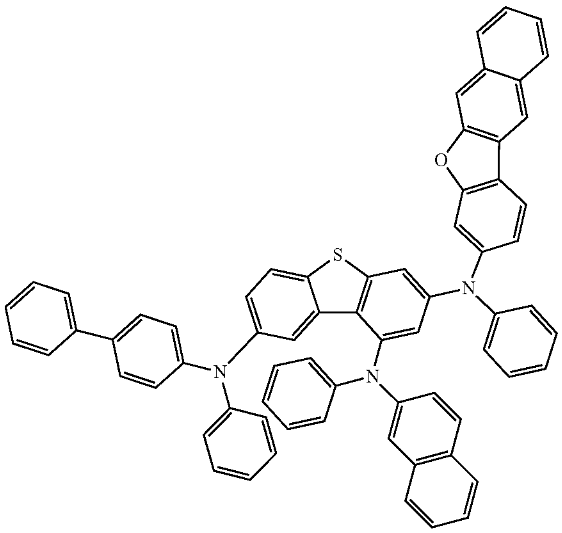
P-137
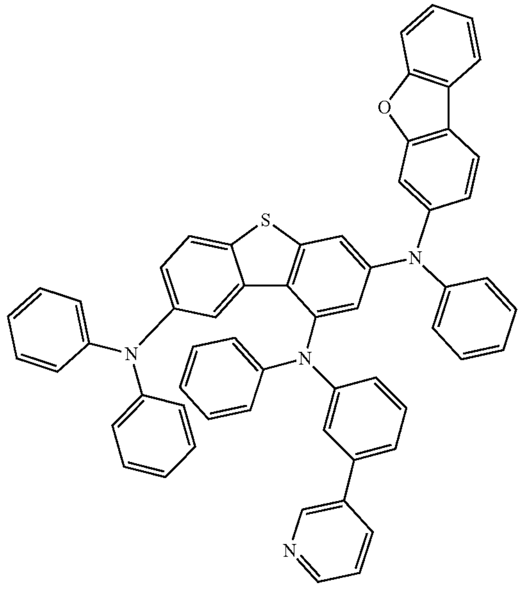

-continued
P-138
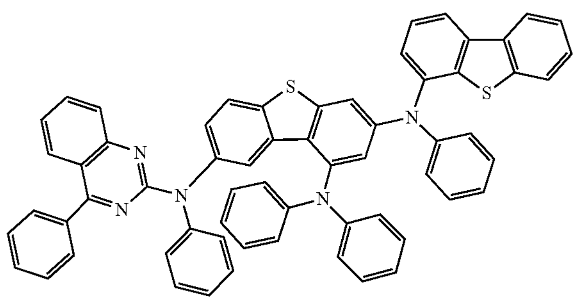
P-139
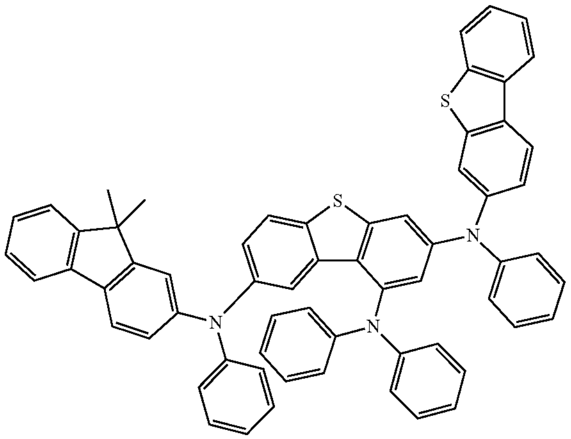
P-140
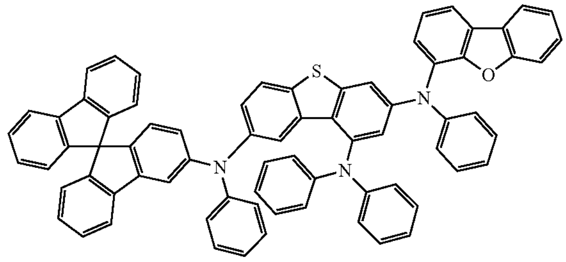
P-141
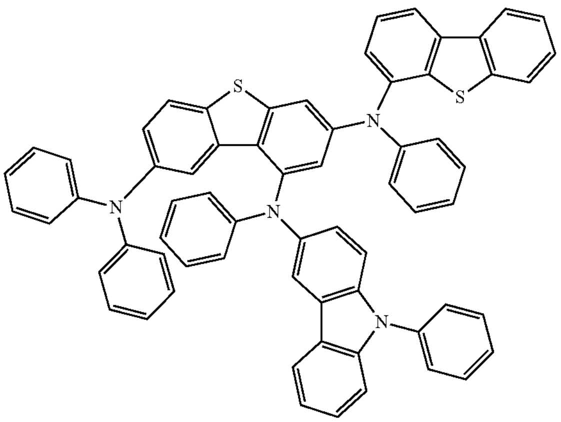
-continued
P-142
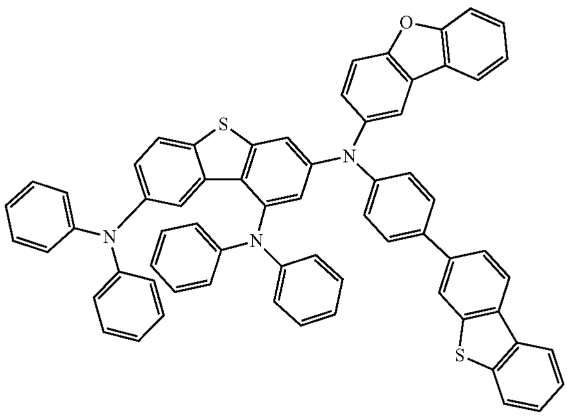
P-143
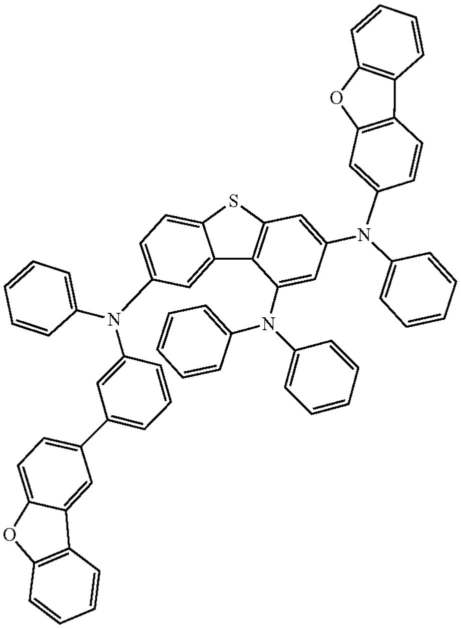
P-144
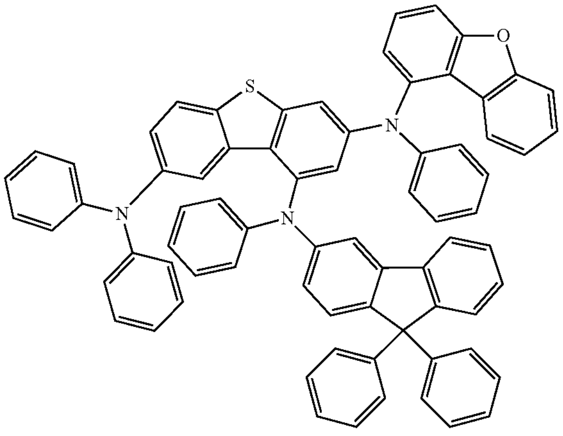

-continued
P-145
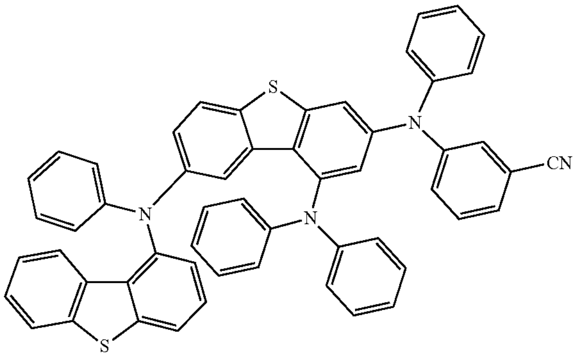
P-146
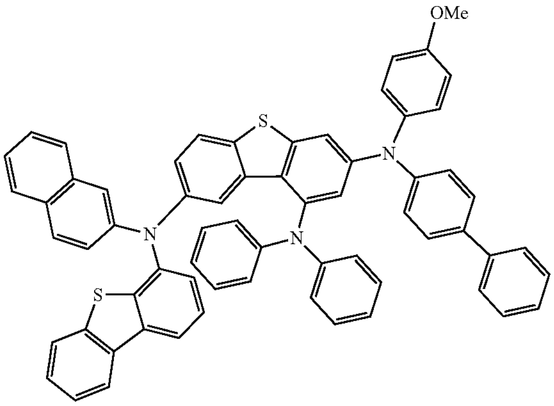
P-147
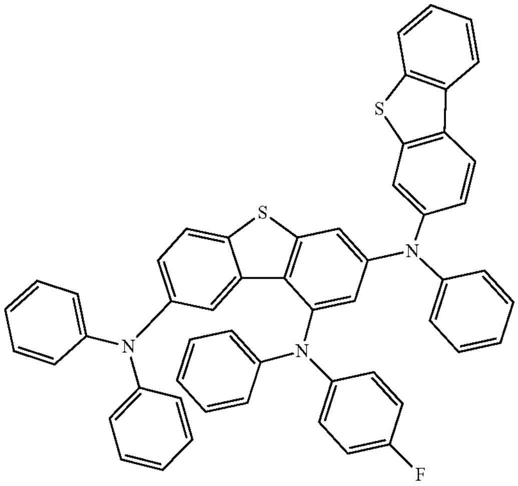
P-148
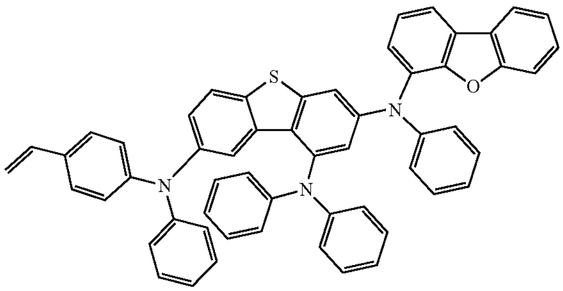
-continued
P-149
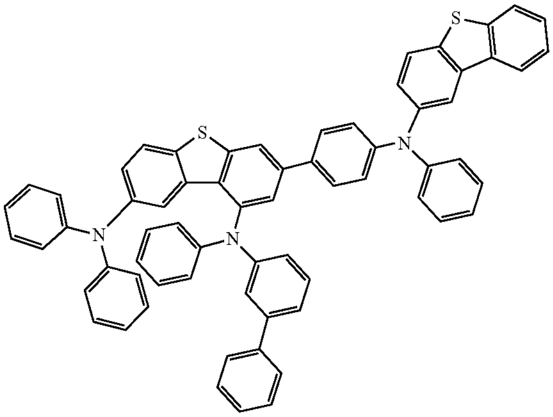
P-150
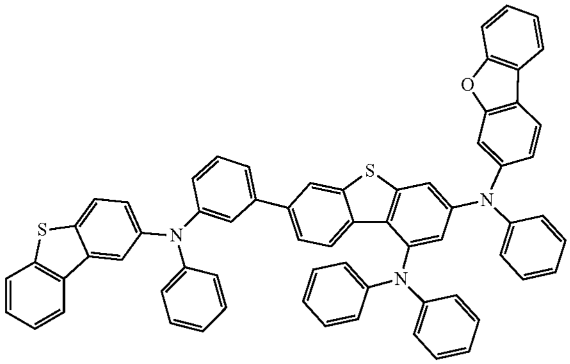
P-151
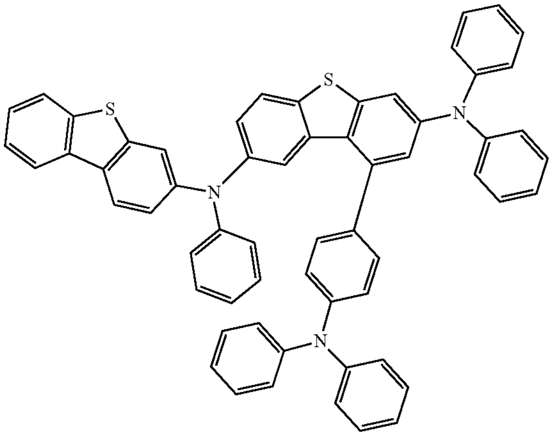
P-152
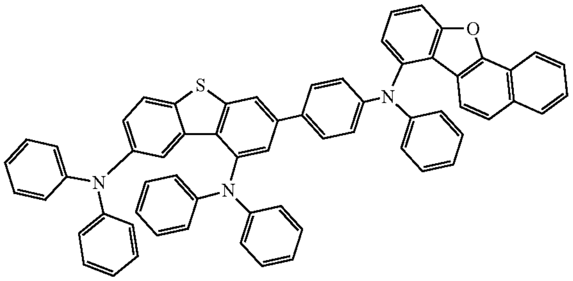

-continued
P-153
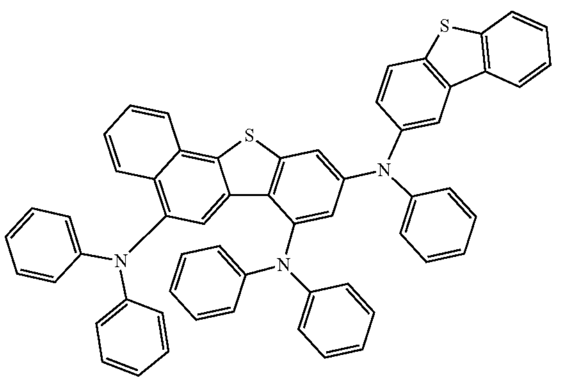
P-154
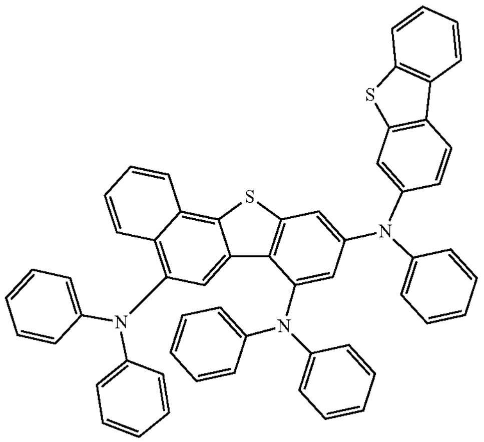
P-155
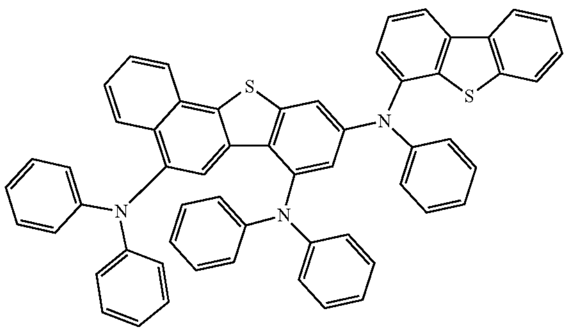
P-156
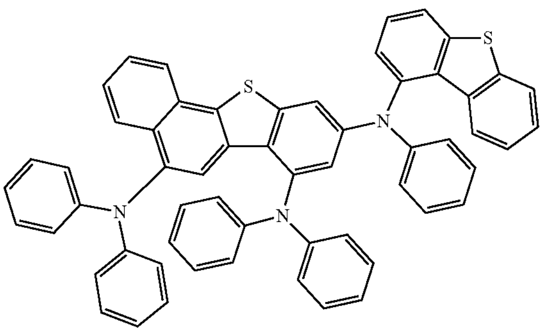
-continued
P-157
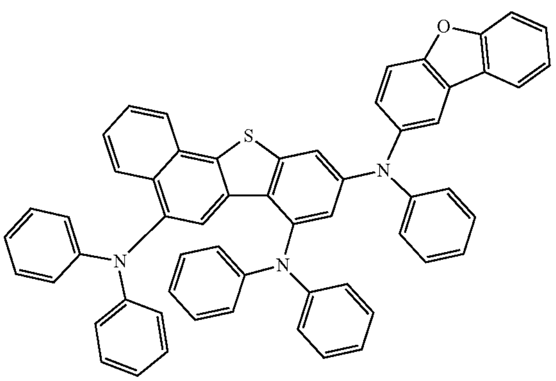
P-158
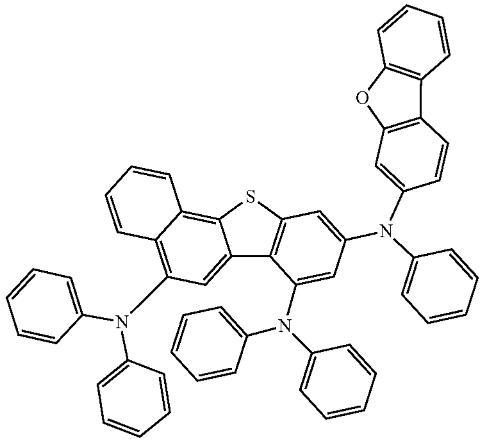
P-159
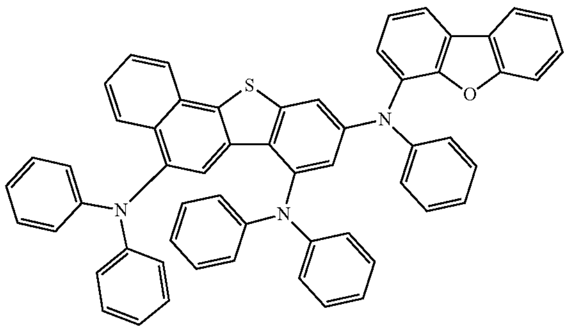
P-160
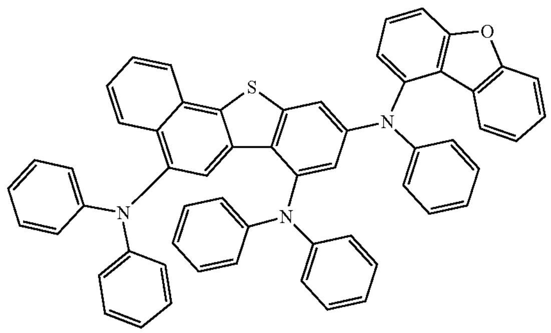

-continued
P-161
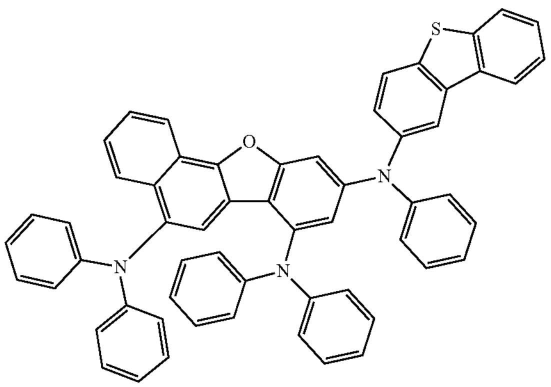
P-162
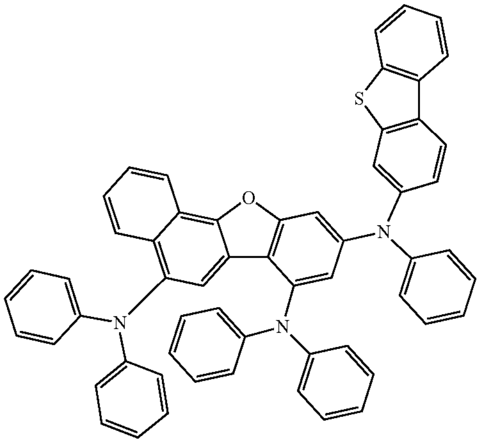
P-163
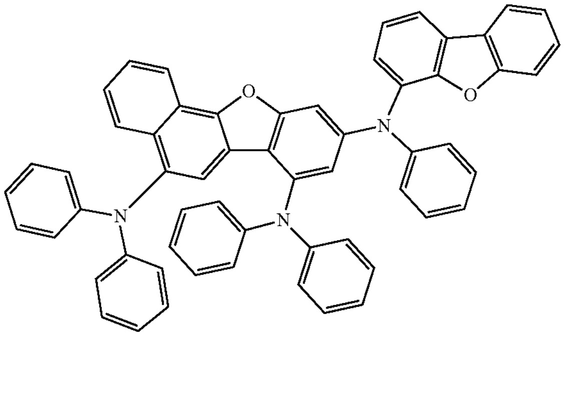
P-164
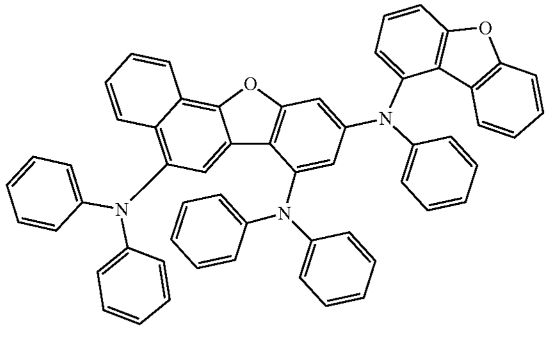
-continued
P-165
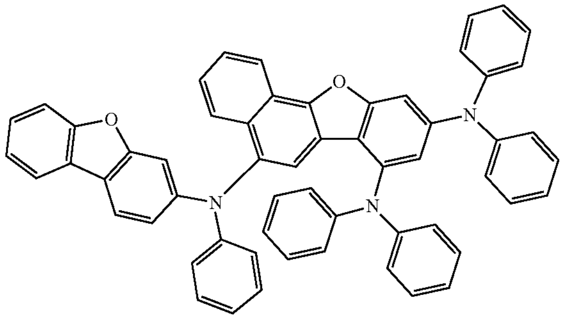
P-166
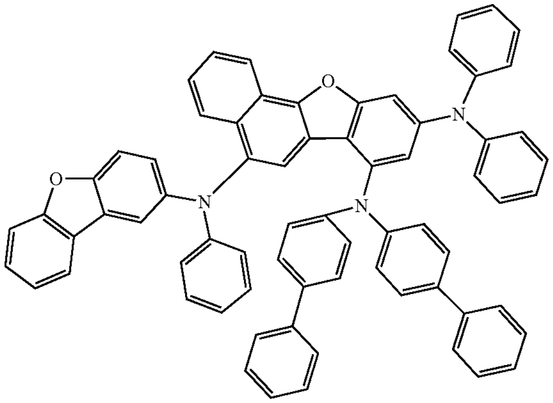
P-167
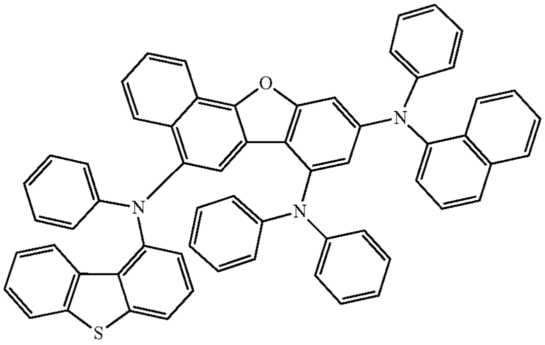
P-168
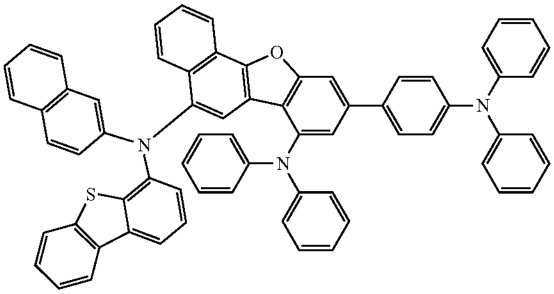

-continued
P-169
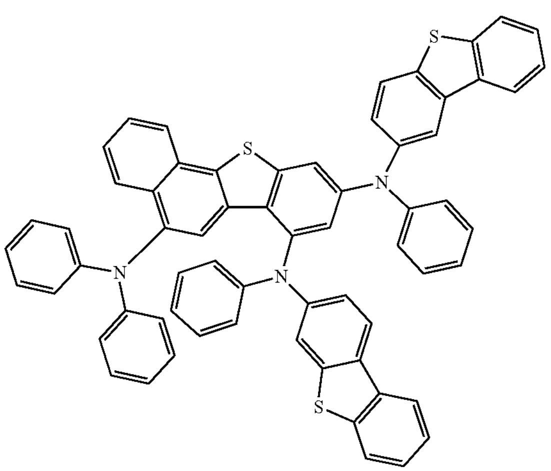
P-170
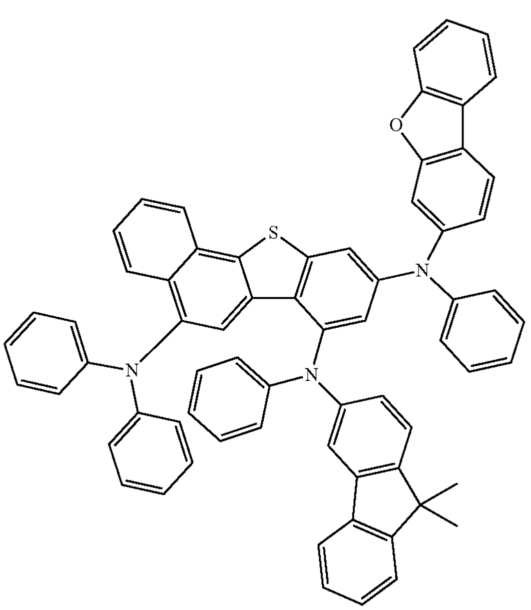
P-171
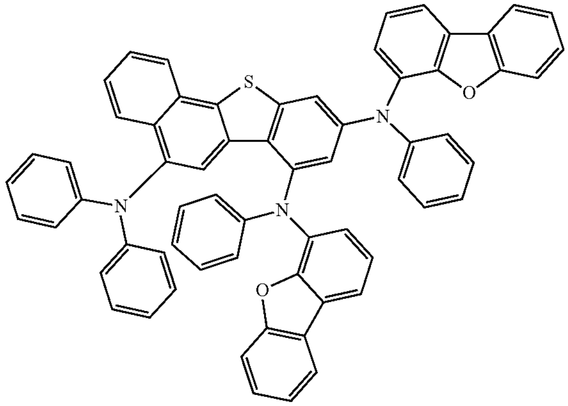
-continued
P-172
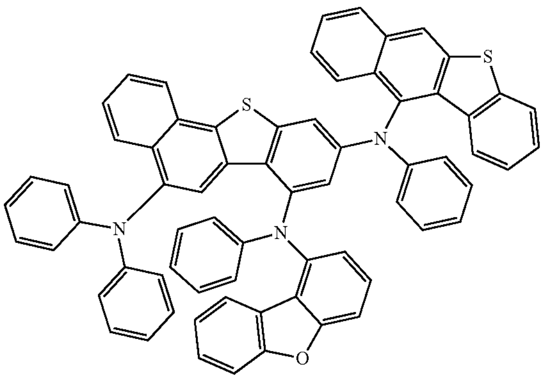
P-173
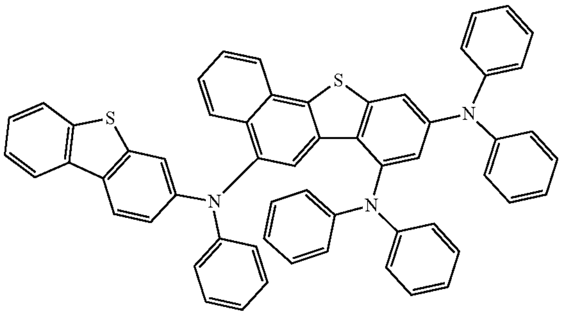
P-174
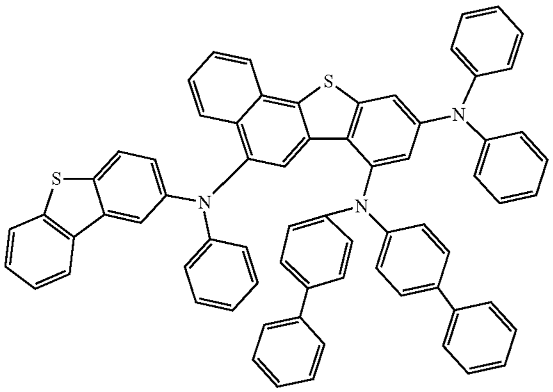
P-175
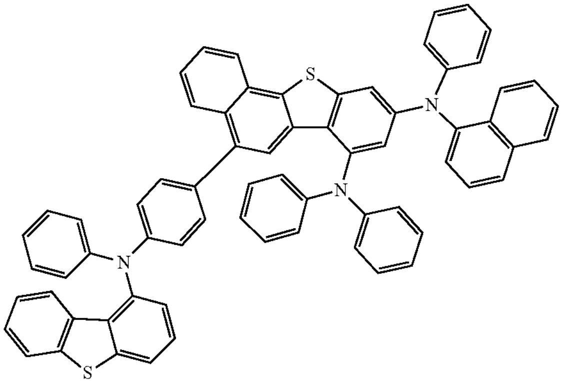

-continued
P-176
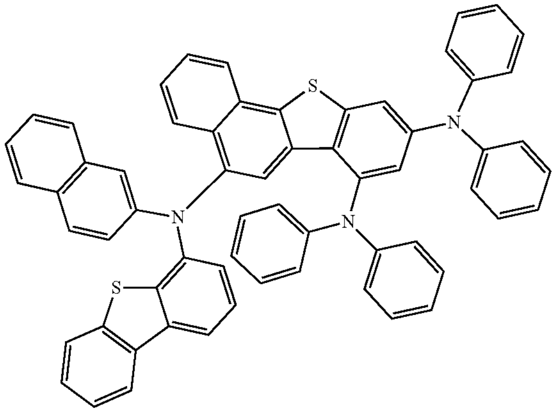
P-177
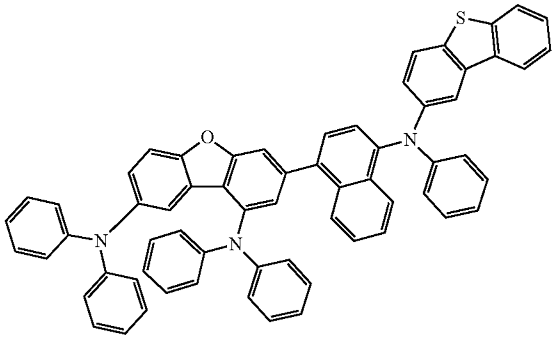
P-178
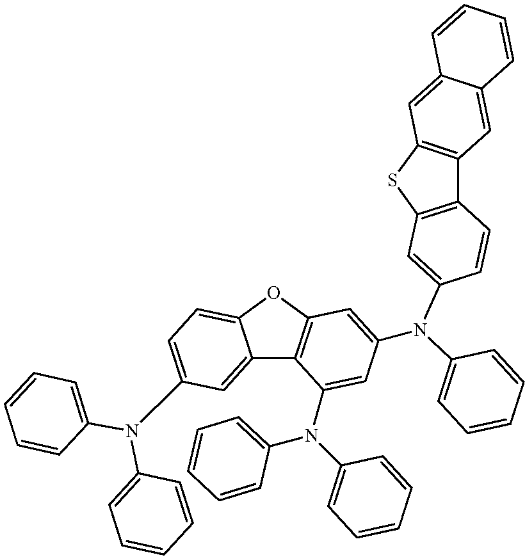
-continued
P-179
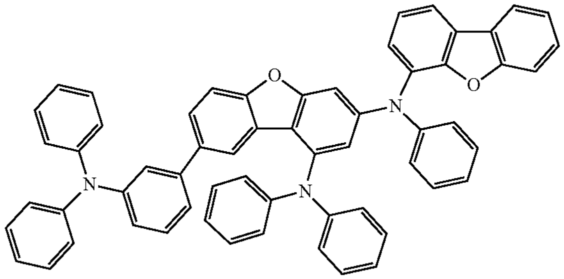
P-180
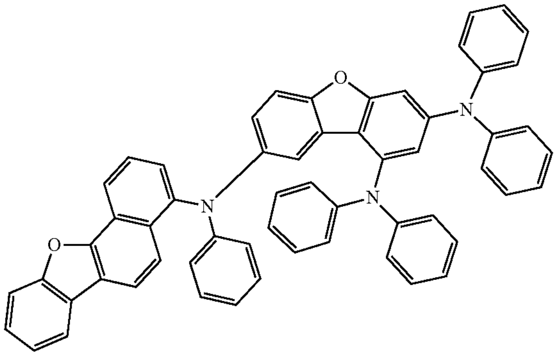
P-181
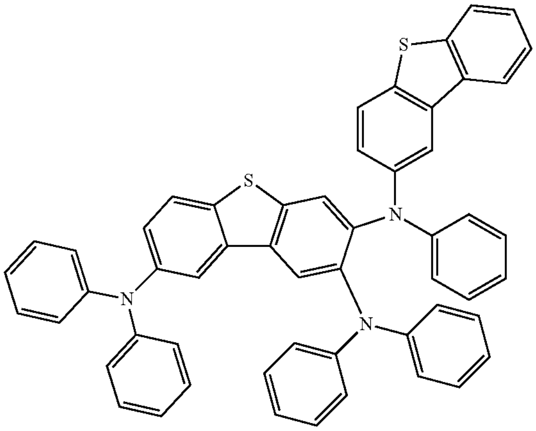
P-182
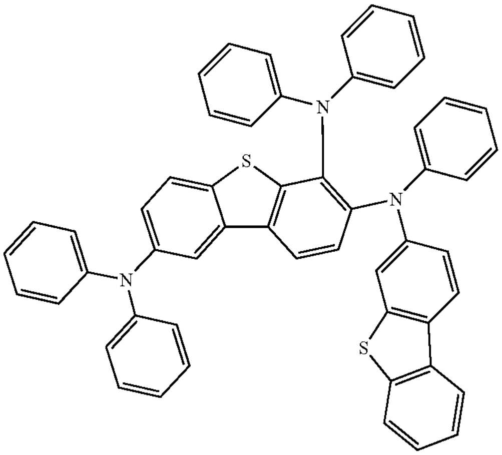

-continued

P-183

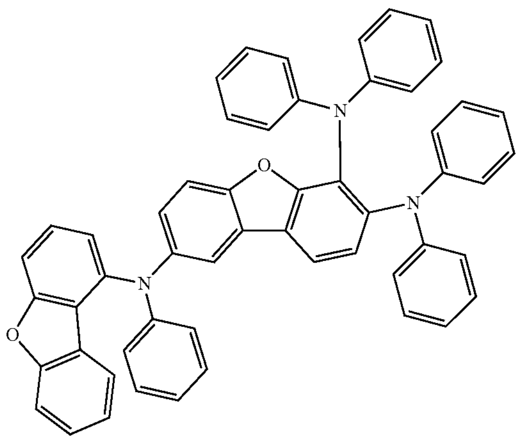

-continued

P-184

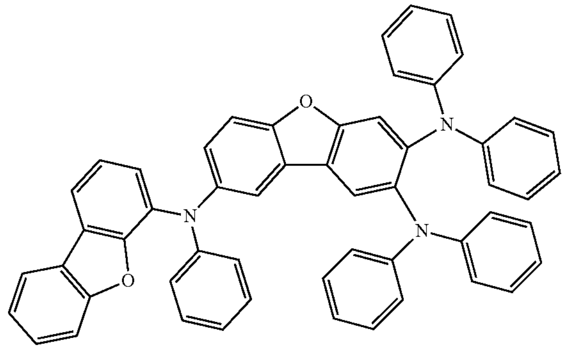

The FD-MS values of the compounds P-1 to P-184 above are shown in the following Table 1.

TABLE 1

| Compound | FD-MS | Compound | FD-MS |
|---|---|---|---|
| P-1 | m/z = 608.19 ($C_{42}H_{28}N_2OS$ = 608.76) | P-2 | m/z = 608.19 ($C_{42}H_{28}N_2OS$ = 608.76) |
| P-3 | m/z = 608.19 ($C_{42}H_{28}N_2OS$ = 608.76) | P-4 | m/z = 608.19 ($C_{42}H_{28}N_2OS$ = 608.76) |
| P-5 | m/z = 592.22 ($C_{42}H_{28}N_2O_2$ = 592.70) | P-6 | m/z = 592.22 ($C_{42}H_{28}N_2O_2$ = 592.70) |
| P-7 | m/z = 592.22 ($C_{42}H_{28}N_2O_2$ = 592.70) | P-8 | m/z = 592.22 ($C_{42}H_{28}N_2O_2$ = 592.70) |
| P-9 | m/z = 684.22 ($C_{48}H_{32}N_2OS$ = 684.86) | P-10 | m/z = 684.22 ($C_{48}H_{32}N_2OS$ = 684.86) |
| P-11 | m/z = 684.22 ($C_{48}H_{32}N_2OS$ = 684.86) | P-12 | m/z = 689.25 ($C_{48}H_{27}D_5N_2OS$ = 689.89) |
| P-13 | m/z = 684.22 ($C_{48}H_{32}N_2OS$ = 684.86) | P-14 | m/z = 684.22 ($C_{48}H_{32}N_2OS$ = 684.86) |
| P-15 | m/z = 760.25 ($C_{54}H_{36}N_2OS$ = 760.96) | P-16 | m/z = 760.25 ($C_{54}H_{36}N_2OS$ = 760.96) |
| P-17 | m/z = 744.28 ($C_{54}H_{36}N_2O_2$ = 744.89) | P-18 | m/z = 668.28 ($C_{48}H_{32}N_2O_2$ = 668.80) |
| P-19 | m/z = 758.29 ($C_{55}H_{38}N_2O_2$ = 758.92) | P-20 | m/z = 668.28 ($C_{48}H_{32}N_2O_2$ = 668.80) |
| P-21 | m/z = 684.22 ($C_{48}H_{32}N_2OS$ = 684.86) | P-22 | m/z = 760.25 ($C_{54}H_{36}N_2OS$ = 760.96) |
| P-23 | m/z = 760.25 ($C_{54}H_{36}N_2OS$ = 760.96) | P-24 | m/z = 760.25 ($C_{54}H_{36}N_2OS$ = 760.96) |
| P-25 | m/z = 734.24 ($C_{52}H_{34}N_2OS$ = 734.92) | P-26 | m/z = 658.21 ($C_{46}H_{30}N_2OS$ = 658.82) |
| P-27 | m/z = 642.23 ($C_{46}H_{30}N_2O_2$ = 642.76) | P-28 | m/z = 718.26 ($C_{52}H_{34}N_2O_2$ = 718.86) |
| P-29 | m/z = 658.21 ($C_{46}H_{30}N_2OS$ = 658.82) | P-30 | m/z = 658.21 ($C_{46}H_{30}N_2OS$ = 658.82) |
| P-31 | m/z = 734.24 ($C_{52}H_{34}N_2OS$ = 734.92) | P-32 | m/z = 658.21 ($C_{46}H_{30}N_2OS$ = 658.82) |
| P-33 | m/z = 658.21 ($C_{46}H_{30}N_2OS$ = 658.82) | P-34 | m/z = 658.21 ($C_{46}H_{30}N_2OS$ = 658.82) |
| P-35 | m/z = 658.21 ($C_{46}H_{30}N_2OS$ = 658.82) | P-36 | m/z = 658.21 ($C_{46}H_{30}N_2OS$ = 658.82) |
| P-37 | m/z = 642.23 ($C_{46}H_{30}N_2O_2$ = 642.76) | P-38 | m/z = 768.28 ($C_{56}H_{36}N_2O_2$ = 768.92) |
| P-39 | m/z = 642.23 ($C_{46}H_{30}N_2O_2$ = 642.76) | P-40 | m/z = 642.23 ($C_{46}H_{30}N_2O_2$ = 642.76) |
| P-41 | m/z = 658.21 ($C_{46}H_{30}N_2OS$ = 658.82) | P-42 | m/z = 658.21 ($C_{46}H_{30}N_2OS$ = 658.82) |
| P-43 | m/z = 658.21 ($C_{46}H_{30}N_2OS$ = 658.82) | P-44 | m/z = 658.21 ($C_{46}H_{30}N_2OS$ = 658.82) |
| P-45 | m/z = 642.23 ($C_{46}H_{30}N_2O_2$ = 642.76) | P-46 | m/z = 642.23 ($C_{46}H_{30}N_2O_2$ = 642.76) |
| P-47 | m/z = 744.28 ($C_{54}H_{36}N_2O_2$ = 744.89) | P-48 | m/z = 642.23 ($C_{46}H_{30}N_2O_2$ = 642.76) |
| P-49 | m/z = 622.21 ($C_{43}H_{30}N_2OS$ = 622.79) | P-50 | m/z = 626.18 ($C_{42}H_{27}FN_2OS$ = 626.75) |
| P-51 | m/z = 702.21 ($C_{48}H_{31}FN_2OS$ = 702.85) | P-52 | m/z = 622.21 ($C_{43}H_{30}N_2OS$ = 622.79) |
| P-53 | m/z = 636.22 ($C_{44}H_{32}N_2OS$ = 636.81) | P-54 | m/z = 686.24 ($C_{48}H_{34}N_2OS$ = 686.87) |
| P-55 | m/z = 650.24 ($C_{45}H_{34}N_2OS$ = 650.84) | P-56 | m/z = 712.25 ($C_{50}H_{36}N_2OS$ = 712.91) |
| P-57 | m/z = 636.22 ($C_{44}H_{32}N_2OS$ = 636.81) | P-58 | m/z = 698.24 ($C_{49}H_{34}N_2OS$ = 698.88) |
| P-59 | m/z = 760.25 ($C_{54}H_{36}N_2OS$ = 760.96) | P-60 | m/z = 686.24 ($C_{48}H_{34}N_2OS$ = 686.87) |
| P-61 | m/z = 650.24 ($C_{45}H_{34}N_2OS$ = 650.84) | P-62 | m/z = 774.27 ($C_{55}H_{38}N_2OS$ = 774.98) |
| P-63 | m/z = 760.25 ($C_{54}H_{36}N_2OS$ = 760.96) | P-64 | m/z = 810.27 ($C_{58}H_{38}N_2OS$ = 811.02) |
| P-65 | m/z = 752.23 ($C_{52}H_{33}FN_2OS$ = 752.91) | P-66 | m/z = 810.27 ($C_{58}H_{38}N_2OS$ = 811.02) |
| P-67 | m/z = 734.24 ($C_{52}H_{34}N_2OS$ = 734.92) | P-68 | m/z = 789.29 ($C_{56}H_{31}D_5N_2OS$ = 790.01) |
| P-69 | m/z = 684.22 ($C_{48}H_{32}N_2OS$ = 684.86) | P-70 | m/z = 836.29 ($C_{60}H_{40}N_2OS$ = 837.05) |
| P-71 | m/z = 734.24 ($C_{52}H_{34}N_2OS$ = 734.92) | P-72 | m/z = 760.25 ($C_{54}H_{36}N_2OS$ = 760.96) |
| P-73 | m/z = 775.27 ($C_{54}H_{37}N_3OS$ = 775.97) | P-74 | m/z = 775.27 ($C_{54}H_{37}N_3OS$ = 775.97) |
| P-75 | m/z = 775.27 ($C_{54}H_{37}N_3OS$ = 775.97) | P-76 | m/z = 775.27 ($C_{54}H_{37}N_3OS$ = 775.97) |
| P-77 | m/z = 759.29 ($C_{54}H_{37}N_3O_2$ = 759.91) | P-78 | m/z = 835.32 ($C_{60}H_{31}N_3O_2$ = 836.01) |
| P-79 | m/z = 835.32 ($C_{60}H_{31}N_3O_2$ = 836.01) | P-80 | m/z = 759.29 ($C_{54}H_{37}N_3O_2$ = 759.91) |
| P-81 | m/z = 851.30 ($C_{60}H_{41}N_3OS$ = 852.07) | P-82 | m/z = 851.30 ($C_{60}H_{41}N_3OS$ = 852.07) |
| P-83 | m/z = 851.30 ($C_{60}H_{41}N_3OS$ = 852.07) | P-84 | m/z = 851.30 ($C_{60}H_{41}N_3OS$ = 852.07) |
| P-85 | m/z = 851.30 ($C_{60}H_{41}N_3OS$ = 852.07) | P-86 | m/z = 851.30 ($C_{60}H_{41}N_3OS$ = 852.07) |
| P-87 | m/z = 852.30 ($C_{60}H_{40}DN_3OS$ = 853.07) | P-88 | m/z = 927.33 ($C_{66}H_{45}N_3OS$ = 928.17) |
| P-89 | m/z = 92733 ($C_{66}H_{45}N_3OS$ = 928.17) | P-90 | m/z = 927.33 ($C_{66}H_{45}N_3OS$ = 928.17) |
| P-91 | m/z = 927.33 ($C_{66}H_{45}N_3OS$ = 928.17) | P-92 | m/z = 92733 ($C_{66}H_{45}N_3OS$ = 928.17) |
| P-93 | m/z = 851.30 ($C_{60}H_{41}N_3OS$ = 852.07) | P-94 | m/z = 851.30 ($C_{60}H_{41}N_3OS$ = 852.07) |
| P-95 | m/z = 851.30 ($C_{60}H_{41}N_3OS$ = 852.07) | P-96 | m/z = 851.30 ($C_{60}H_{41}N_3OS$ = 852.07) |
| P-97 | m/z = 718.26 ($C_{52}H_{34}N_2O_2$ = 718.86) | P-98 | m/z = 656.25 ($C_{47}H_{32}N_2O_2$ = 656.79) |
| P-99 | m/z = 642.23 ($C_{45}H_{30}N_2O_2$ = 642.76) | P-100 | m/z = 642.23 ($C_{46}H_{30}N_2O_2$ = 642.76) |
| P-101 | m/z = 744.28 ($C_{54}H_{36}N_2O_2$ = 744.89) | P-102 | m/z = 794.29 ($C_{58}H_{38}N_2O_2$ = 794.9S) |
| P-103 | m/z = 794.29 ($C_{58}H_{38}N_2O_2$ = 794.95) | P-104 | m/z = 808.31 ($C_{59}H_{40}N_2O_2$ = 808.98) |

TABLE 1-continued

| Compound | FD-MS | Compound | FD-MS |
|---|---|---|---|
| P-105 | m/z = 622.21 ($C_{43}H_{30}N_2OS$ = 622.79) | P-106 | m/z = 684.22 ($C_{48}H_{32}N_2OS$ = 684.86) |
| P-107 | m/z = 684.22 ($C_{48}H_{32}N_2OS$ = 684.86) | P-108 | m/z = 790.21 ($C_{54}H_{34}N_2OS_2$ = 791.00) |
| P-109 | m/z = 790.21 ($C_{54}H_{34}N_2OS_2$ = 791.00) | P-110 | m/z = 708.22 ($C_{50}H_{32}N_2OS$ = 708.88) |
| P-111 | m/z = 782.24 ($C_{56}H_{34}N_2OS$ = 782.96) | P-112 | m/z = 824.25 ($C_{58}H_{36}N_2O_2S$ = 825.00) |
| P-113 | m/z = 791.24 ($C_{54}H_{37}N_3S_2$ = 792.03) | P-114 | m/z = 791.24 ($C_{54}H_{37}N_3S_2$ = 792.03) |
| P-115 | m/z = 791.24 ($C_{54}H_{37}N_3S_2$ = 792.03) | P-116 | m/z = 791.24 ($C_{54}H_{37}N_3S_2$ = 792.03) |
| P-117 | m/z = 775.27 ($C_{54}H_{37}N_3OS$ = 775.97) | P-118 | m/z = 775.27 ($C_{54}H_{37}N_3OS$ = 775.97) |
| P-119 | m/z = 775.27 ($C_{54}H_{37}N_3OS$ = 775.97) | P-120 | m/z = 825.28 ($C_{58}H_{39}N_3OS$ = 826.03) |
| P-121 | m/z = 897.23 ($C_{60}H_{39}N_3S_3$ = 898.17) | P-122 | m/z = 881.25 ($C_{60}H_{39}N_3OS_2$ = 882.11) |
| P-123 | m/z = 865.28 ($C_{60}H_{39}N_3O_2S$ = 866.05) | P-124 | m/z = 931.27 ($C_{64}H_{41}N_3OS_2$ = 932.17) |
| P-125 | m/z = 791.24 ($C_{54}H_{37}N_3S_2$ = 792.03) | P-126 | m/z = 943.31 ($C_{66}H_{45}$ $N_3S_2$ = 944.23) |
| P-127 | m/z = 791.24 ($C_{54}H_{37}N_3S_2$ = 792.03) | P-128 | m/z = 841.26 ($C_{58}H_{39}N_3S_2$ = 842.09) |
| P-129 | m/z = 775.27 ($C_{54}H_{37}N_3OS$ = 775.97) | P-130 | m/z = 891.33 ($C_{63}H_{45}N_3OS$ = 892.13) |
| P-131 | m/z = 775.27 ($C_{54}H_{37}N_3OS$ = 775.97) | P-132 | m/z = 901.31 ($C_{64}H_{43}N_3OS$ = 902.13) |
| P-133 | m/z = 917.29 ($C_{64}H_{43}N_3S_2$ = 918.19) | P-134 | m/z = 901.31 ($C_{64}H_{43}N_3OS$ = 902.13) |
| P-135 | m/z = 1017.32 ($C_{72}H_{47}N_3S_2$ = 1018.31) | P-136 | m/z = 951.33 ($C_{68}H_{45}N_3OS$ = 952.19) |
| P-137 | m/z = 852.29 ($C_{59}H_{40}N_4OS$ = 853.06) | P-138 | m/z = 919.28 ($C_{62}H_{41}N_5S_2$ = 920.17) |
| P-139 | m/z = 907.31 ($C_{63}H_{45}N_3S_2$ = 908.19) | P-140 | m/z = 1013.34 ($C_{73}H_{47}N_3OS$ = 1014.26) |
| P-141 | m/z = 956.30 ($C_{66}H_{44}N_4S_2$ = 957.23) | P-142 | m/z = 957.28 ($C_{66}H_{43}N_3OS_2$ = 958.21) |
| P-143 | m/z = 941.31 ($C_{66}H_{43}N_3O_2S$ = 942.15) | P-144 | m/z = 1015.36 ($C_{73}H_{49}N_3OS$ = 1016.28) |
| P-145 | m/z = 816.24 ($C_{55}H_{36}N_4S_2$ = 817.04) | P-146 | m/z = 947.30 ($C_{65}H_{45}N_3OS_2$ = 948.22) |
| P-147 | m/z = 809.23 ($C_{54}H_{36}FN_3S_2$ = 810.02) | P-148 | m/z = 801.28 ($C_{56}H_{39}N_3OS$ = 802.01) |
| P-149 | m/z = 943.31 ($C_{66}H_{45}N_3S_2$ = 944.23) | P-150 | m/z = 957.28 ($C_{66}H_{43}N_3OS_2$ = 958.21) |
| P-151 | m/z = 867.27 ($C_{60}H_{41}N_3S_2$ = 868.13) | P-152 | m/z = 901.31 ($C_{64}H_{43}N_3OS$ = 902.13) |
| P-153 | m/z = 841.26 ($C_{58}H_{39}N_3S_2$ = 842.09) | P-154 | m/z = 841.26 ($C_{58}H_{39}N_3S_2$ = 842.09) |
| P-155 | m/z = 841.26 ($C_{58}H_{39}N_3S_2$ = 842.09) | P-156 | m/z = 841.26 ($C_{58}H_{39}N_3S_2$ = 842.09) |
| P-157 | m/z = 825.28 ($C_{58}H_{39}N_3OS$ = 826.03) | P-158 | m/z = 825.28 ($C_{58}H_{39}N_3OS$ = 826.03) |
| P-159 | m/z = 825.28 ($C_{58}H_{39}N_3OS$ = 826.03) | P-160 | m/z = 825.28 ($C_{58}H_{39}N_3OS$ = 826.03) |
| P-161 | m/z = 825.28 ($C_{58}H_{39}N_3OS$ = 826.03) | P-162 | m/z = 825.28 ($C_{58}H_{39}N_3OS$ = 826.03) |
| P-163 | m/z = 809.30 ($C_{58}H_{39}N_3O_2$ = 809.97) | P-164 | m/z = 809.30 ($C_{58}H_{39}N_3O_2$ = 809.97) |
| P-165 | m/z = 809.30 ($C_{58}H_{39}N_3O_2$ = 809.97) | P-166 | m/z = 961.37 ($C_{70}H_{47}N_3O_2$ = 962.17) |
| P-167 | m/z = 875.30 ($C_{62}H_{41}N_3OS$ = 876.09) | P-168 | m/z = 951.33 ($C_{68}H_{45}N_3OS$ = 952.19) |
| P-169 | m/z = 947.25 ($C_{64}H_{41}N_3S_3$ = 948.23) | P-170 | m/z = 941.34 ($C_{67}H_{47}N_3OS$ = 942.19) |
| P-171 | m/z = 915.29 ($C_{64}H_{41}N_3O_2S$ = 916.11) | P-172 | m/z = 981.28 ($C_{68}H_{43}N_3OS_2$ = 982.23) |
| P-173 | m/z = 841.26 ($C_{58}H_{39}N_3S_2$ = 842.09) | P-174 | m/z = 993.32 ($C_{70}H_{47}N_3S_2$ = 994.29) |
| P-175 | m/z = 967.31 ($C_{68}H_{45}N_3S_2$ = 968.25) | P-176 | m/z = 891.27 ($C_{62}H_{41}N_3S_2$ = 892.15) |
| P-177 | m/z = 901.31 ($C_{64}H_{43}N_3OS$ = 902.13) | P-178 | m/z = 825.28 ($C_{58}H_{39}N_3OS$ = 826.03) |
| P-179 | m/z = 835.32 ($C_{60}H_{41}N_3O_2$ = 836.01) | P-180 | m/z = 809.30 ($C_{58}H_{39}N_3O_2$ = 809.97) |
| P-181 | m/z = 791.24 ($C_{54}H_{37}N_3S_2$ = 792.03) | P-182 | m/z = 791.24 ($C_{54}H_{37}N_3S_2$ = 792.03) |
| P-183 | m/z = 759.29 ($C_{54}H_{37}N_3O_2$ = 759.91) | P-184 | m/z = 759.29 ($C_{54}H_{37}N_3O_2$ = 759.91) |

In another aspect of the present invention, the present invention provides an organic electric element comprising a first electrode, a second electrode, and an organic material layer formed between the first electrode and the second electrode, wherein the organic material layer comprises a single compound two or more compounds represented by Formula 1. The organic material layer comprises at least one of a hole injection layer, a hole transport layer, an emission-auxiliary layer, a light emitting layer, an electron transport-auxiliary layer, an electron transport layer and an electron injection layer, preferably, the compound is comprised in the emission-auxiliary layer.

Also, in another aspect of the present invention, the present invention provides an electronic device comprising a display device and a control unit for driving the display device, wherein the display device comprises the organic electric element. Here, the organic electric element comprises the compound represented by Formula 1.

Hereinafter, synthesis example of the compound represented by Formula 1 and preparation method of an organic electroluminescent element according to the present invention will be described in detail by way of examples. However, the present invention is not limited to the following examples.

SYNTHESIS EXAMPLE

The compound represented by Formula 1 according to the present invention can be synthesized by reacting Sub 1 and Sub 2 as shown in Reaction Scheme 1 below, but there is no limitation thereto.

<Reaction Scheme 1>

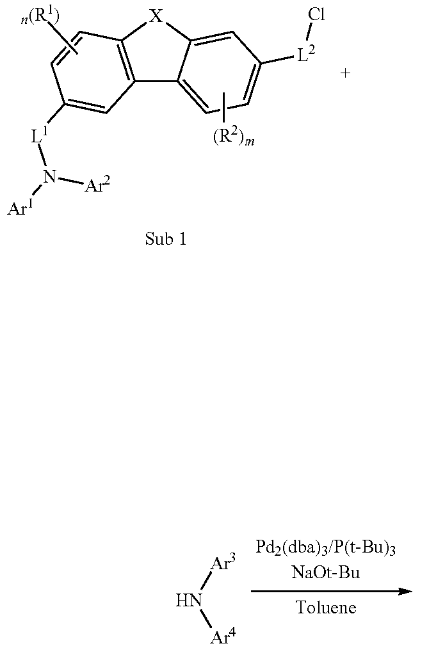

Sub 1

Sub 2

-continued
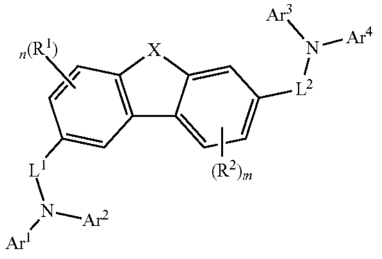
Final Products
Exemplary Compounds of Sub 1
The compounds belonging to Sub 1 of Reaction Scheme 1 may be the following compounds, but there is no limitation thereto.
Sub1-1
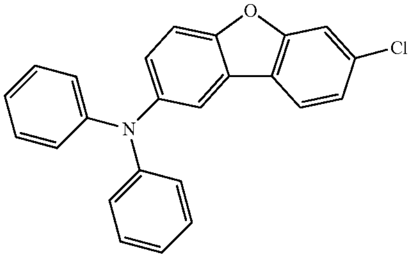
Sub1-2
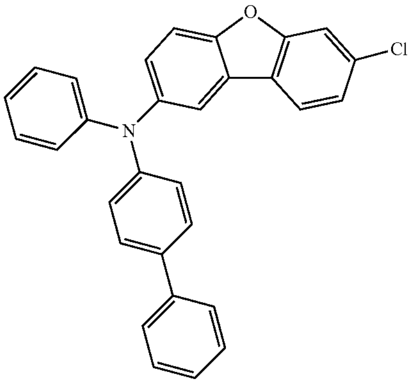
Sub1-3
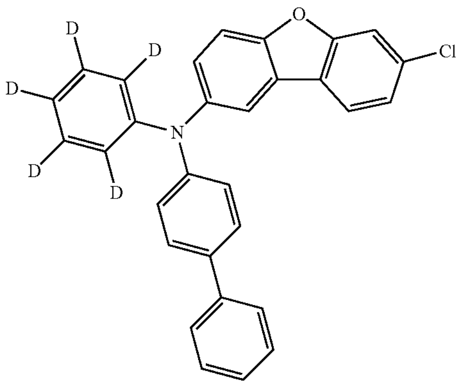
-continued
Sub1-4
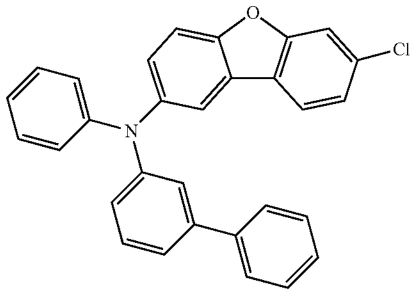
Sub1-5
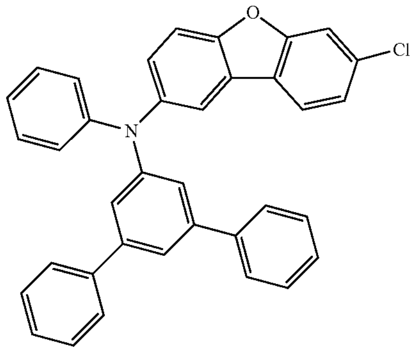
Sub1-6
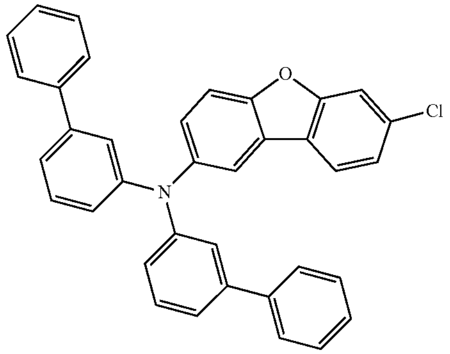
Sub1-7
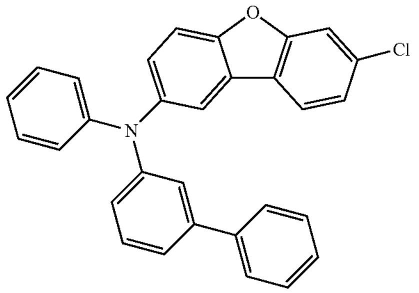
Sub1-8
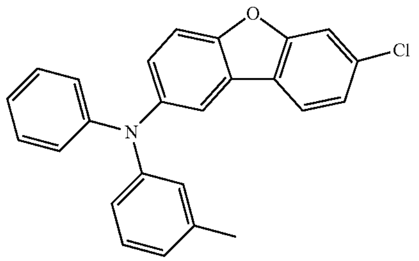

-continued
Sub1-9
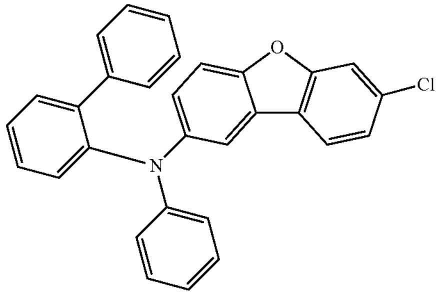
Sub1-10
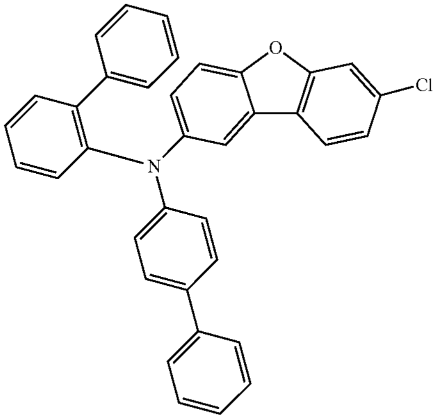
Sub1-11
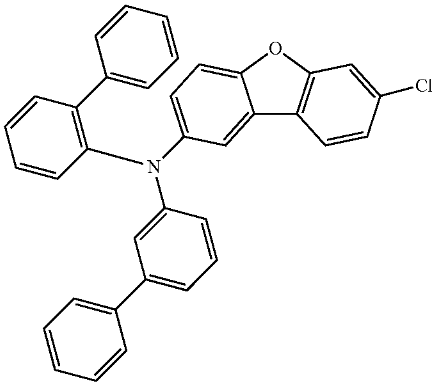
Sub1-12
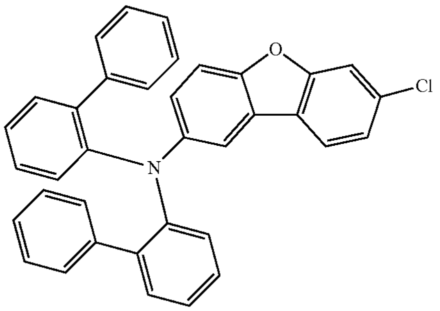
-continued
Sub1-13
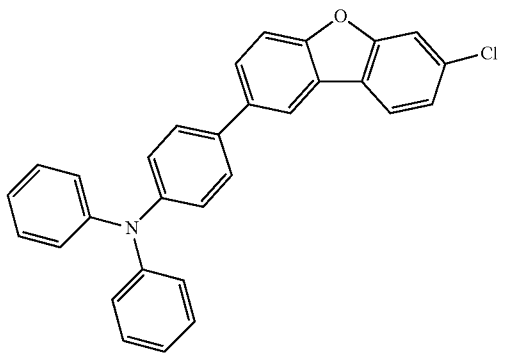
Sub1-14
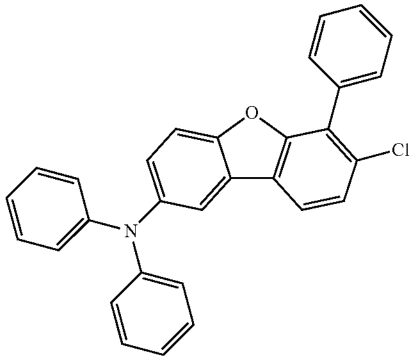
Sub1-15
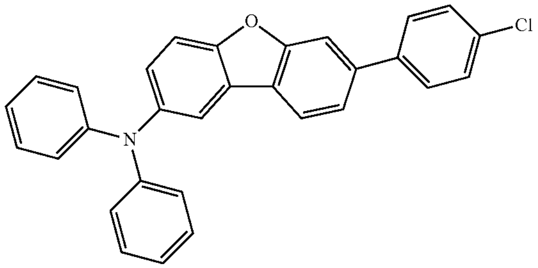
Sub1-16
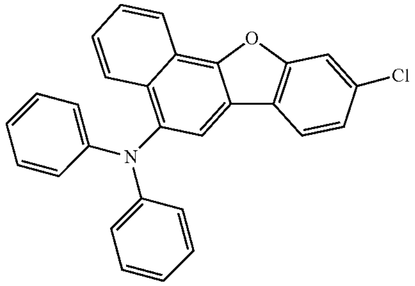
Sub1-17
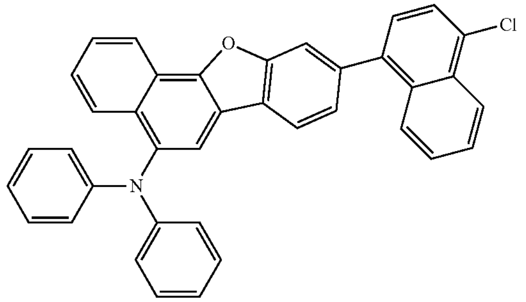

-continued
Sub1-18
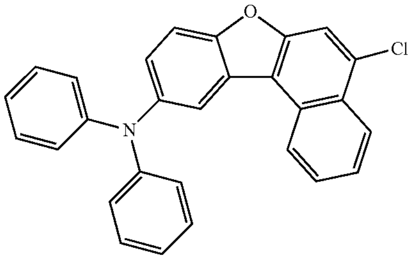
Sub1-19
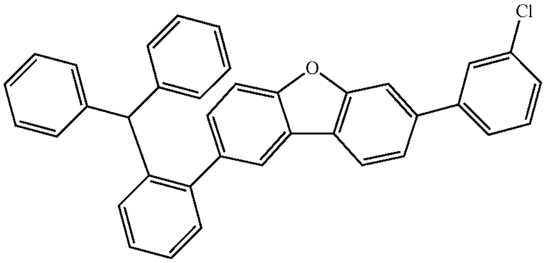
Sub1-20
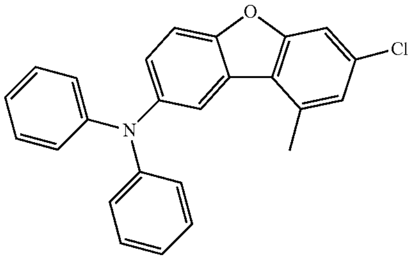
Sub1-21
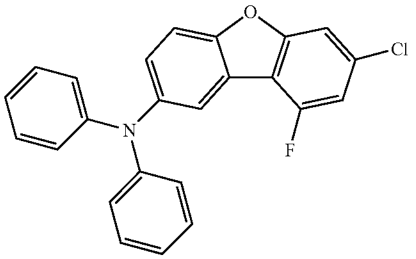
Sub1-22
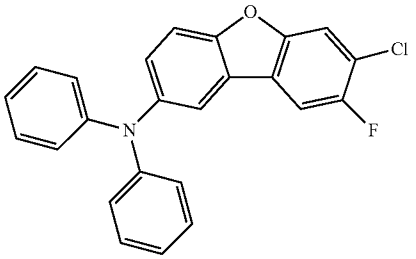
Sub1-23
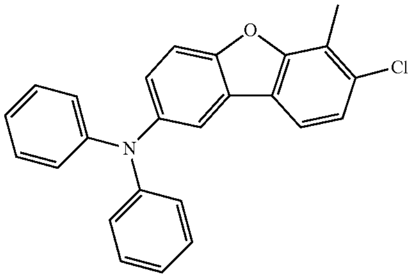
-continued
Sub1-24
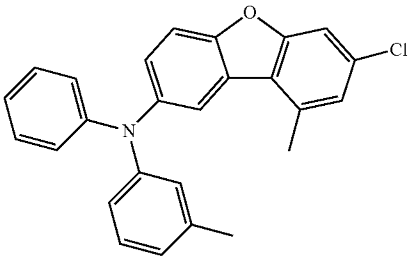
Sub1-25
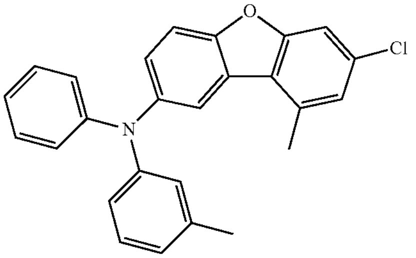
Sub1-26
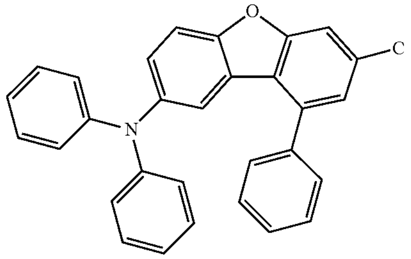
Sub1-27
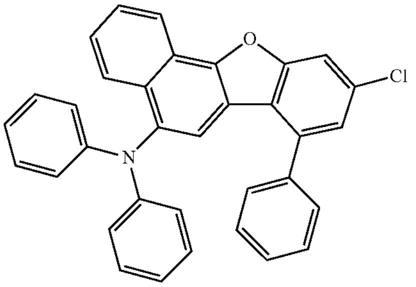
Sub1-28
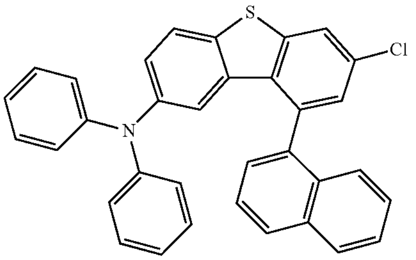

-continued
Sub1-29
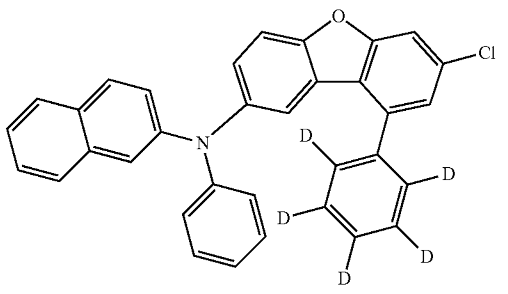
Sub1-30
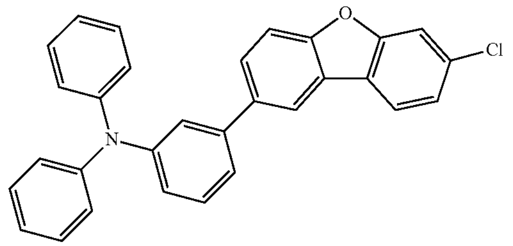
Sub1-31
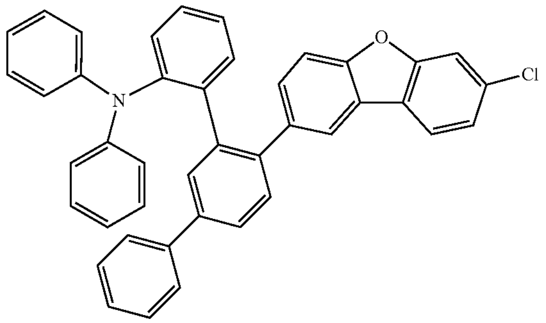
Sub1-32
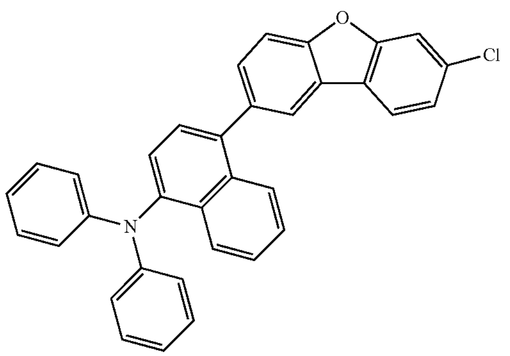
-continued
Sub1-33
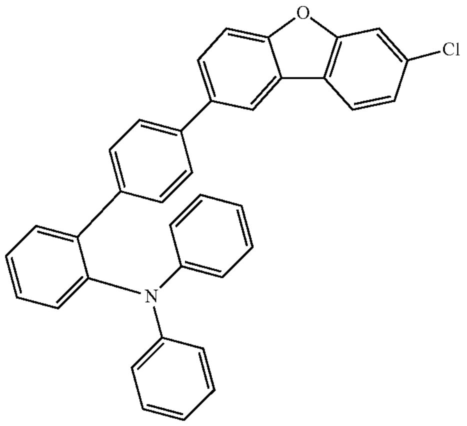
Sub1-34
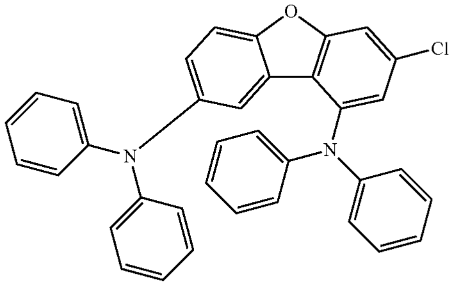
Sub1-35
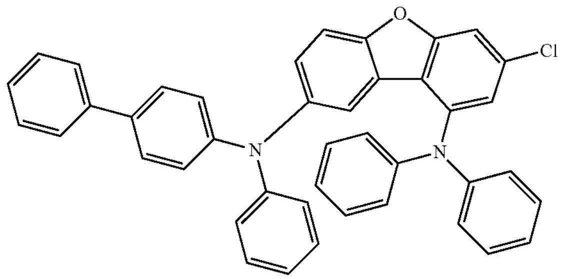
Sub1-36
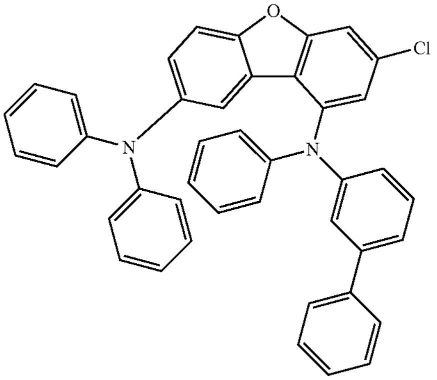

-continued
Sub1-37
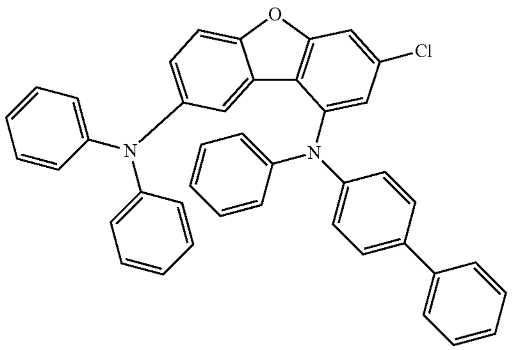
Sub1-38
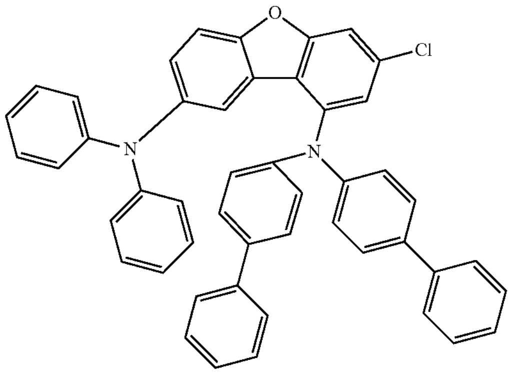
Sub1-39
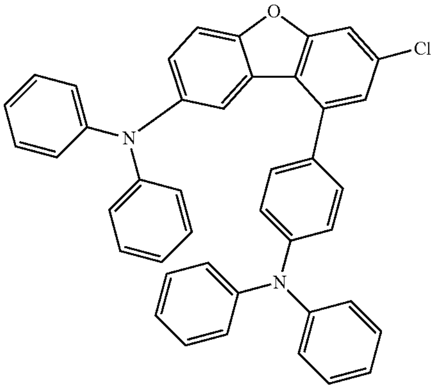
Sub1-40
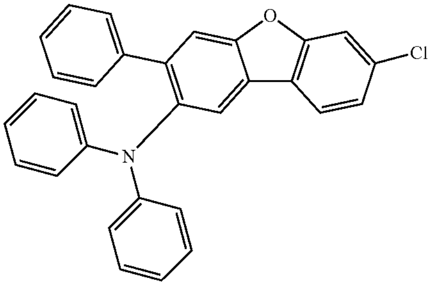
-continued
Sub1-41
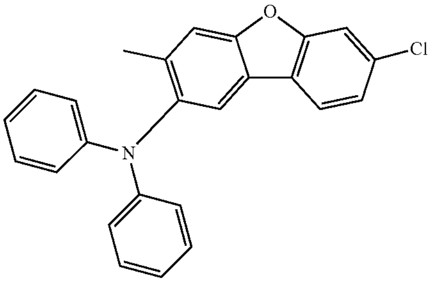
Sub1-42
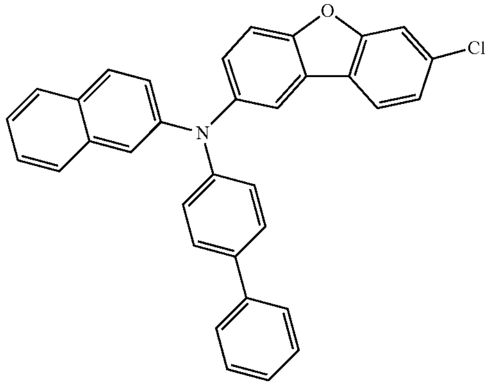
Sub1-43
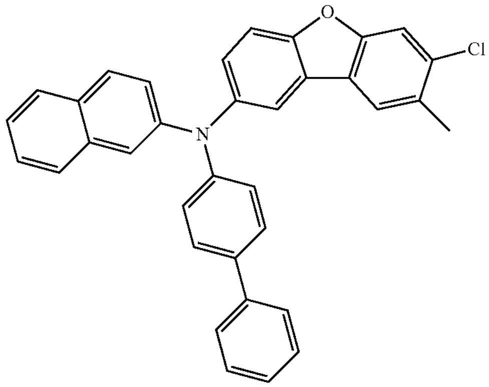
Sub1-44
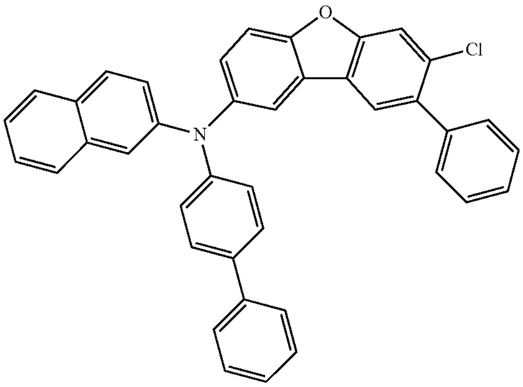

-continued
Sub1-45
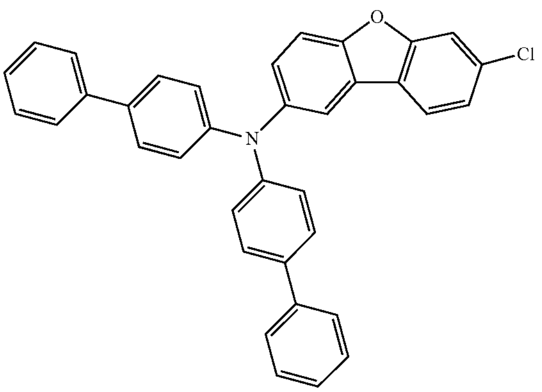
Sub1-46
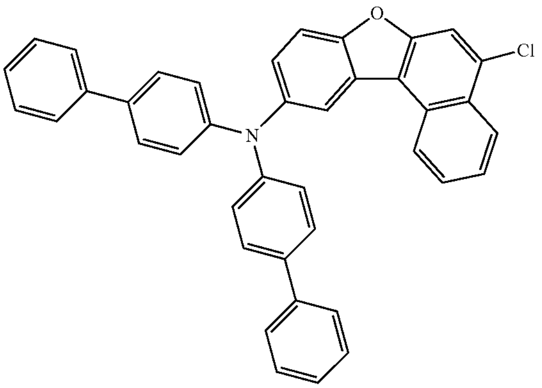
Sub1-47
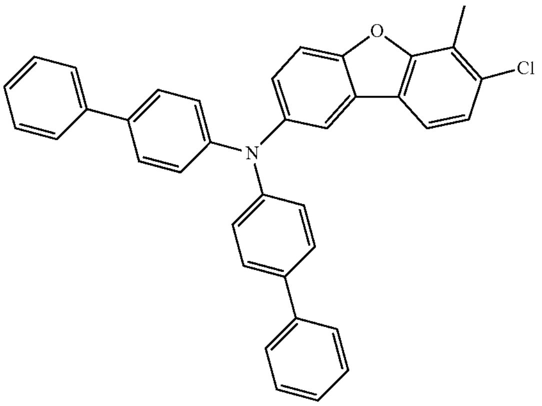
Sub1-48
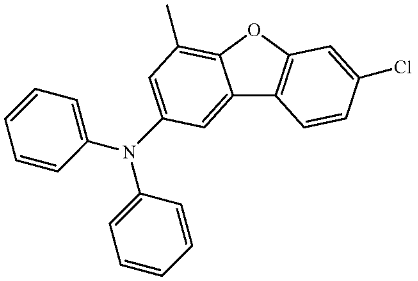
-continued
Sub1-49
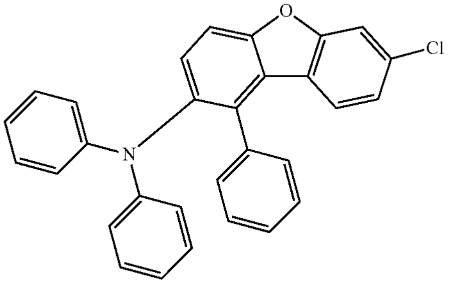
Sub1-50
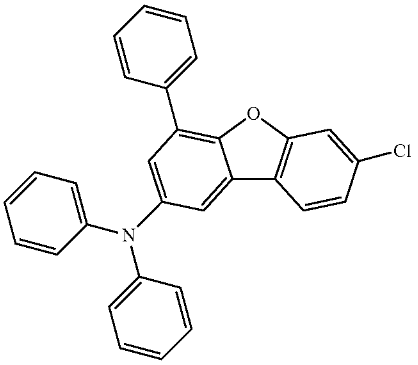
Sub1-51
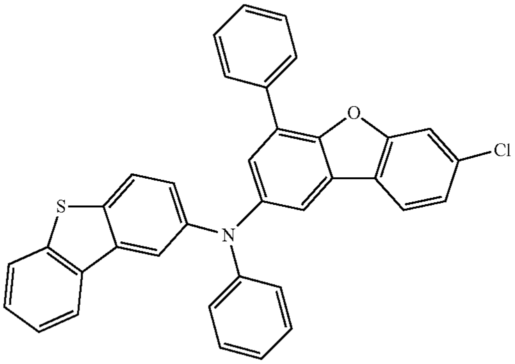
Sub1-52
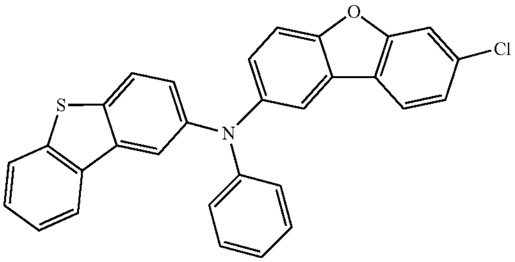
Sub1-53
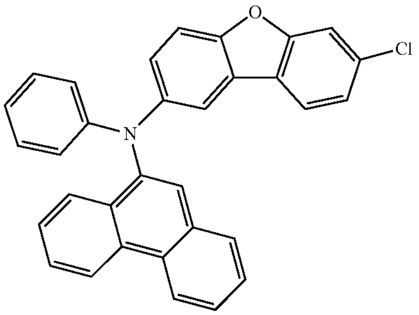

-continued
Sub1-54
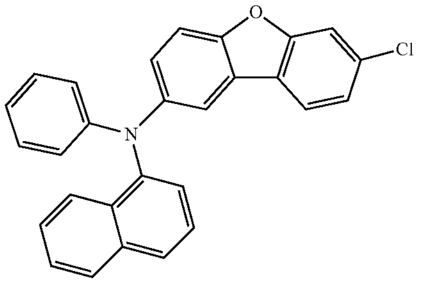
Sub1-55
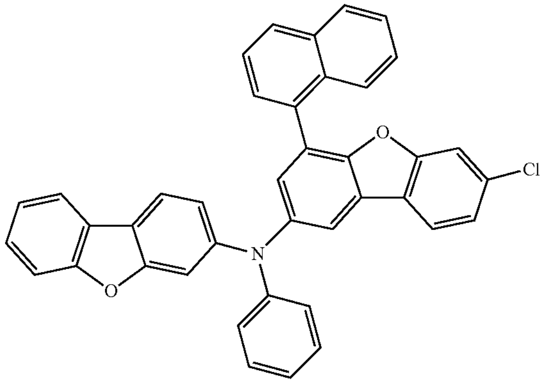
Sub1-56
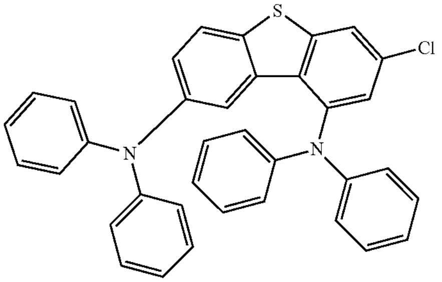
Sub1-57
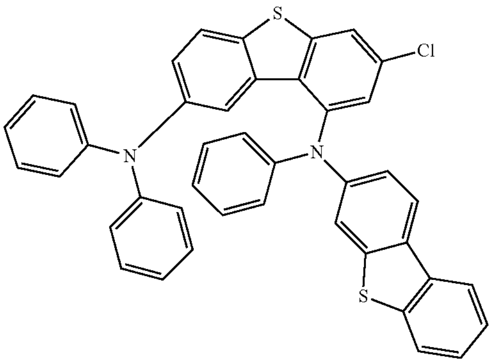
-continued
Sub1-58
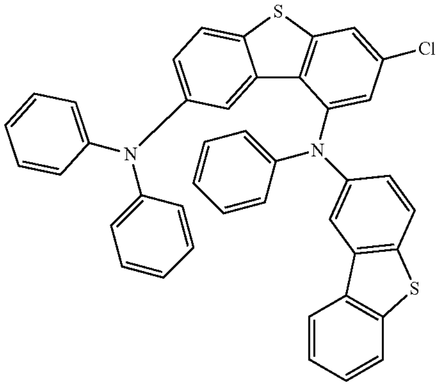
Sub1-59
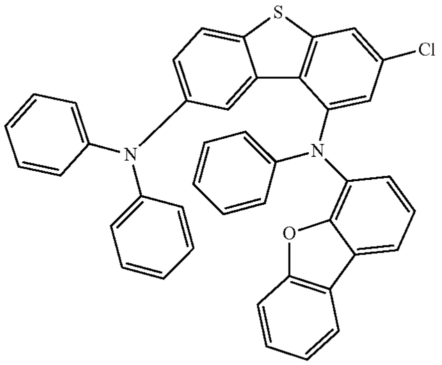
Sub1-60
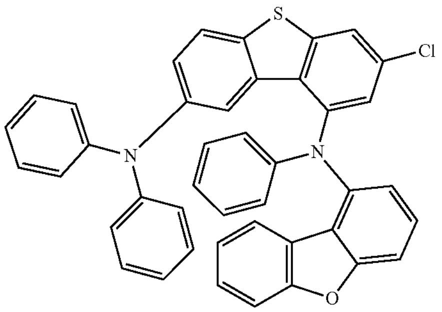
Sub1-61
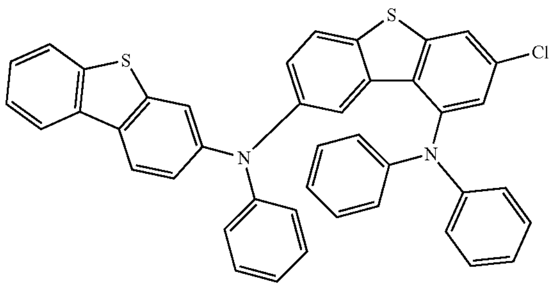

-continued
Sub1-62
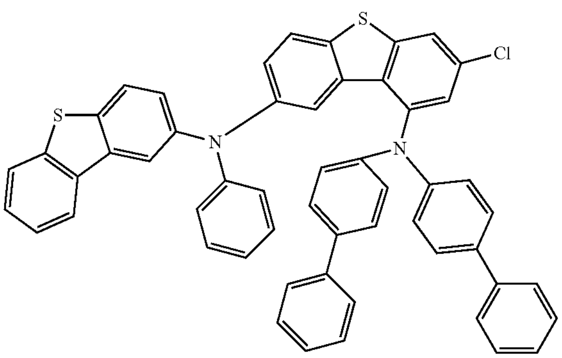
Sub1-63
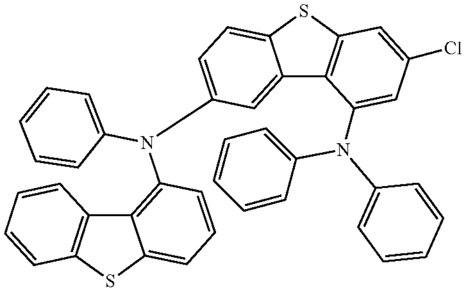
Sub1-64
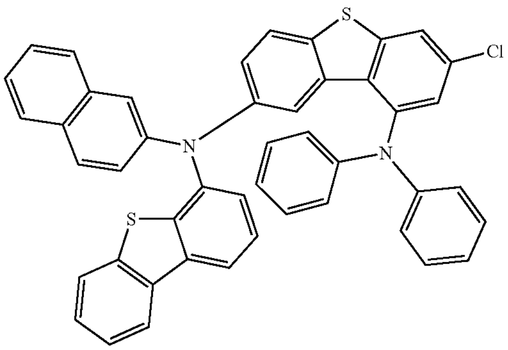
Sub1-65
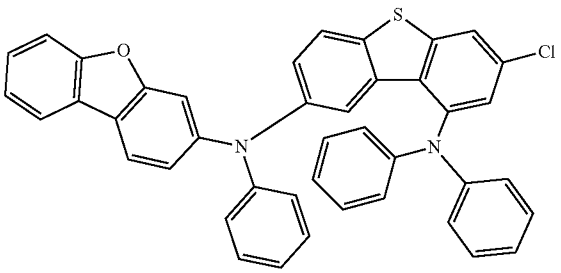
Sub1-66
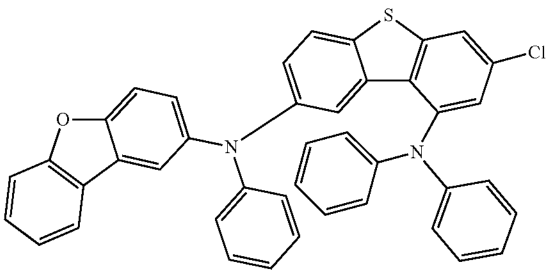
-continued
Sub1-67
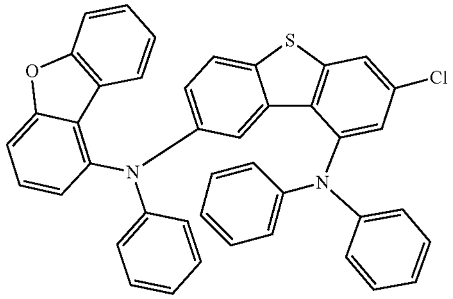
Sub1-68
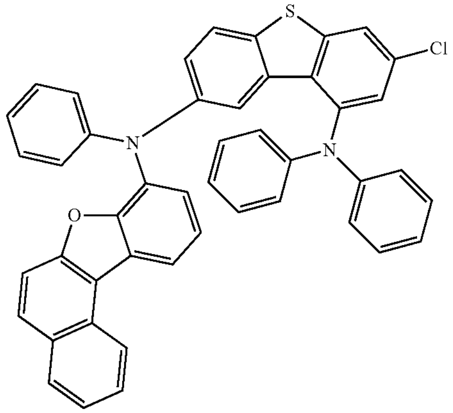
Sub1-69
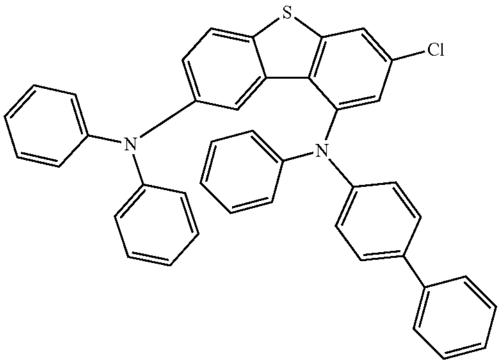
Sub1-70
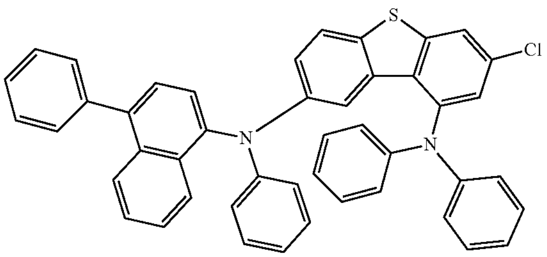

-continued
Sub1-71
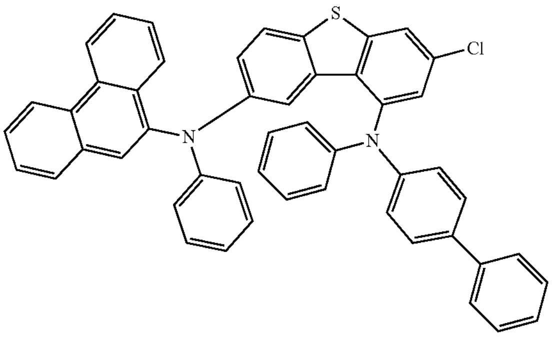
Sub1-72
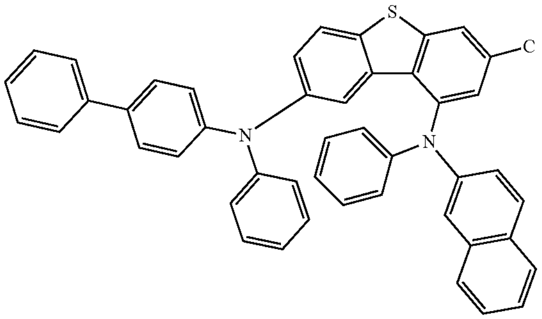
Sub1-73
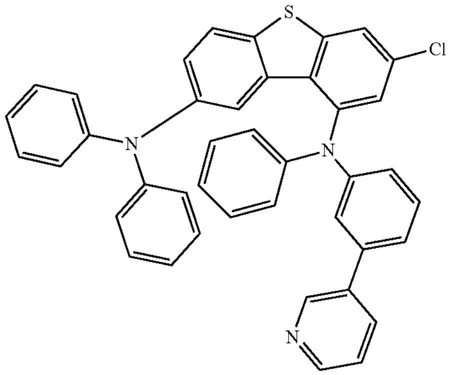
Sub1-74
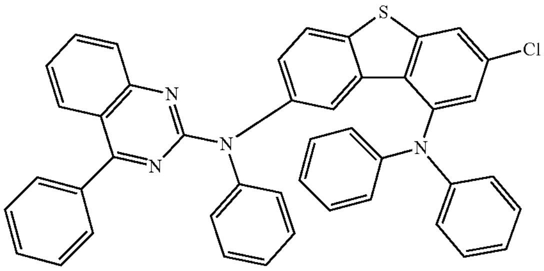
-continued
Sub1-75
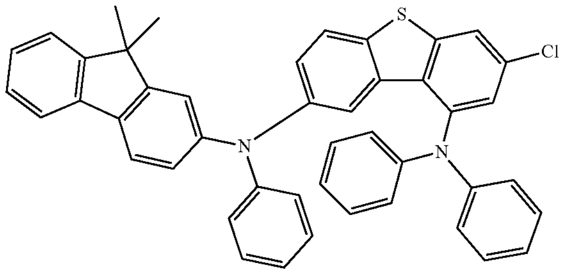
Sub1-76
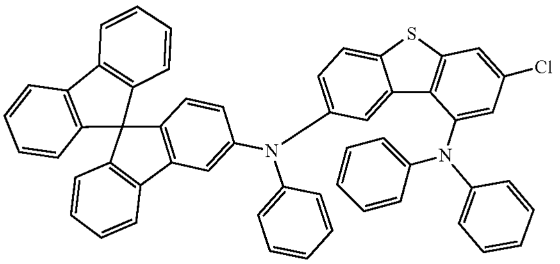
Sub1-77
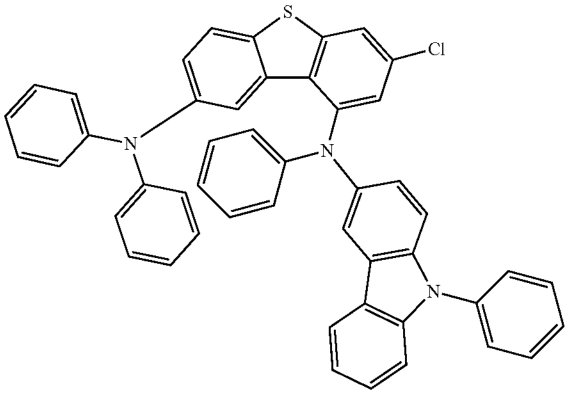
Sub1-78
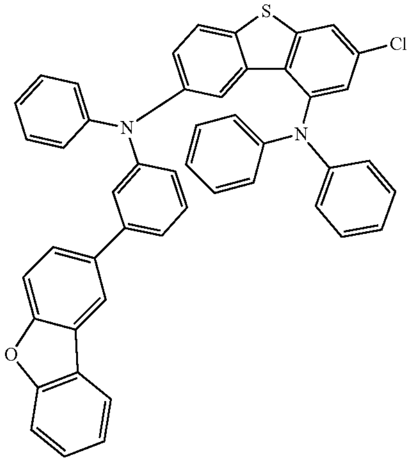

-continued
Sub1-79
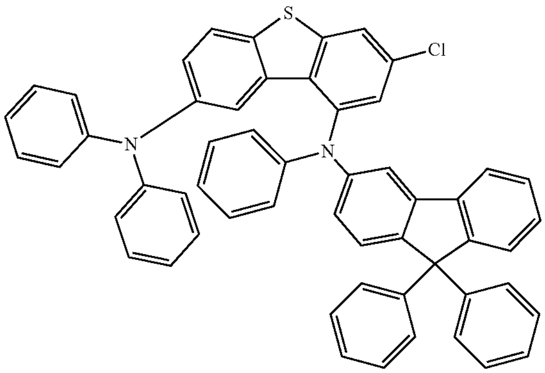
Sub1-80
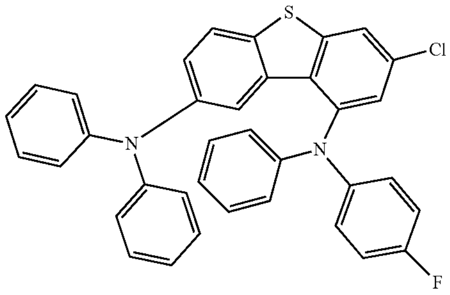
Sub1-81
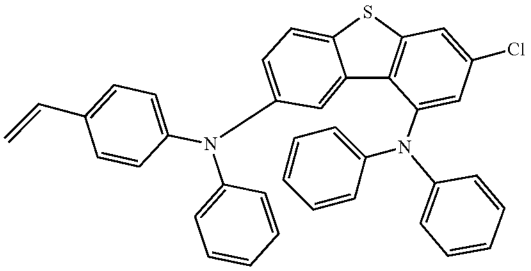
Sub1-82
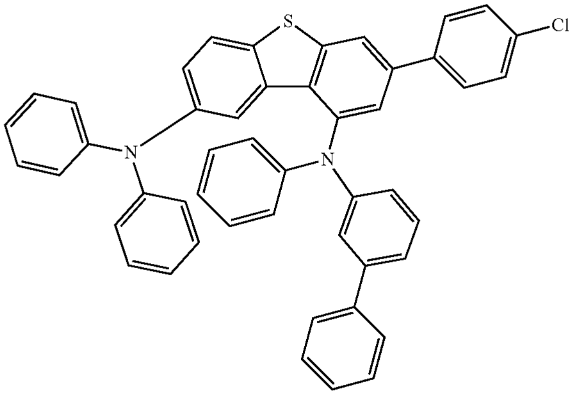
-continued
Sub1-83
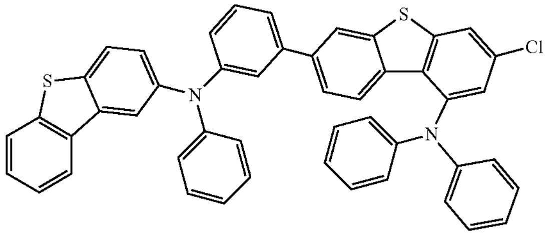
Sub1-84
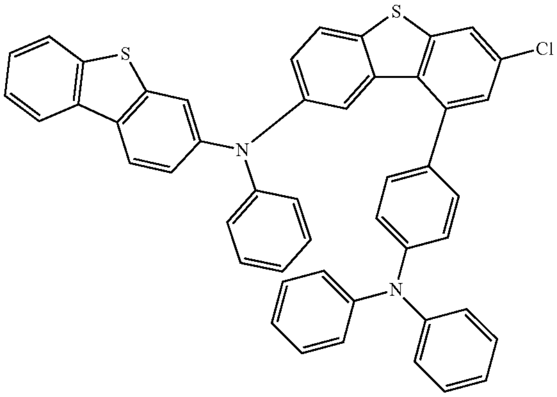
Sub1-85
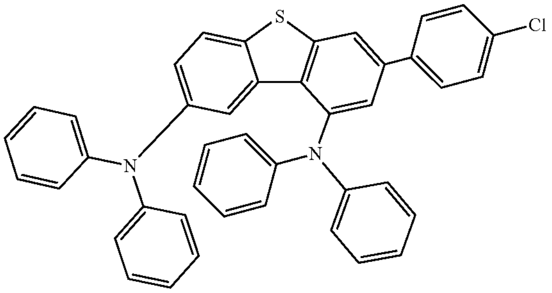
Sub1-86
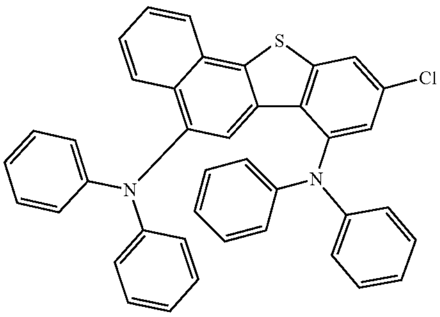
Sub1-87
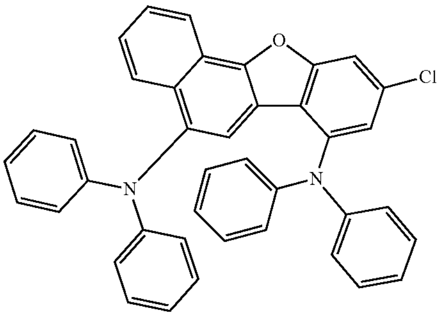

-continued
Sub1-88
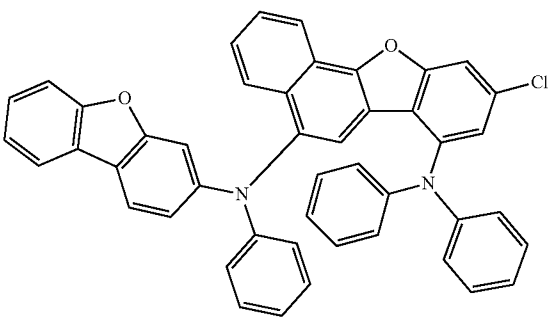
Sub1-89
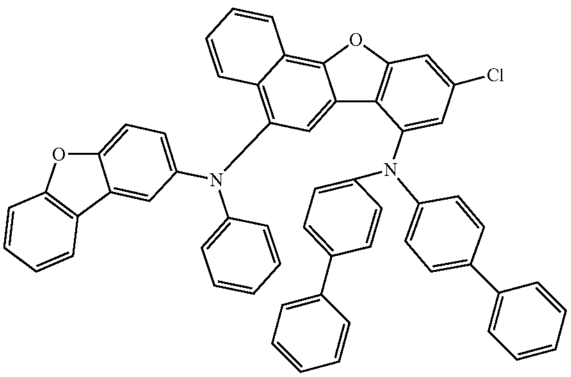
Sub1-90
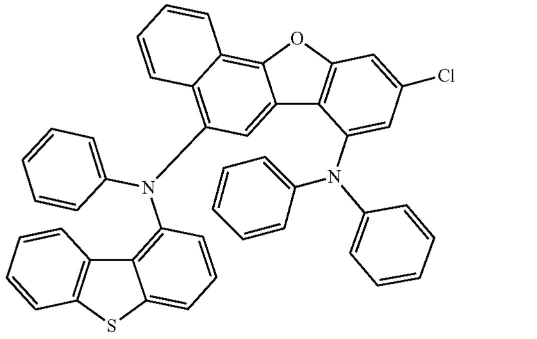
Sub1-91
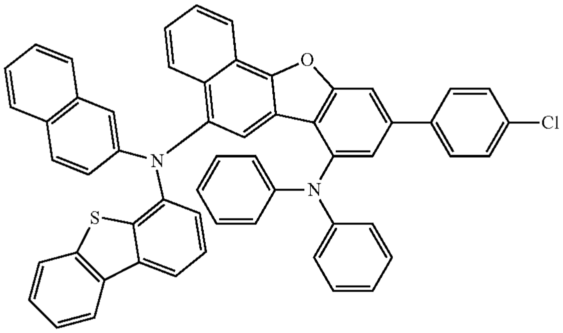
-continued
Sub1-92
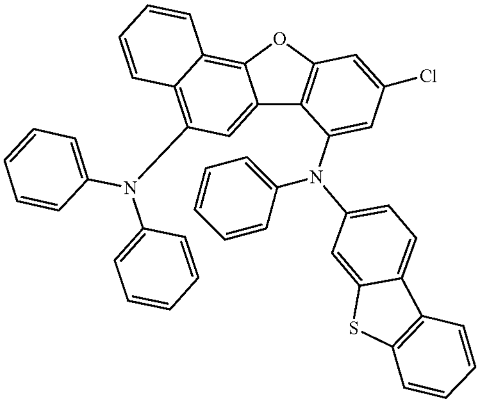
Sub1-93
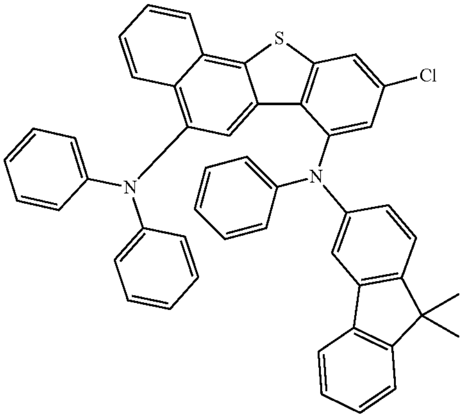
Sub1-94
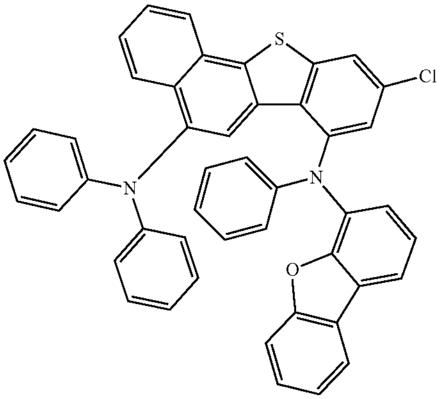
Sub1-95
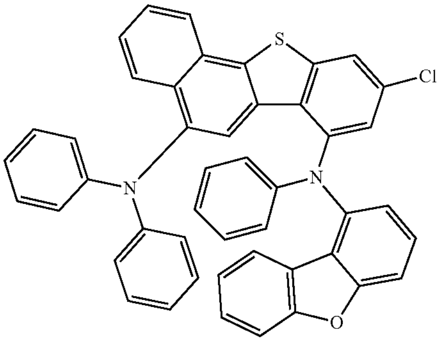

-continued
Sub1-96
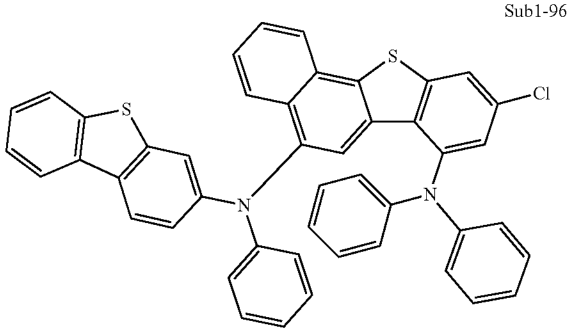
Sub1-97
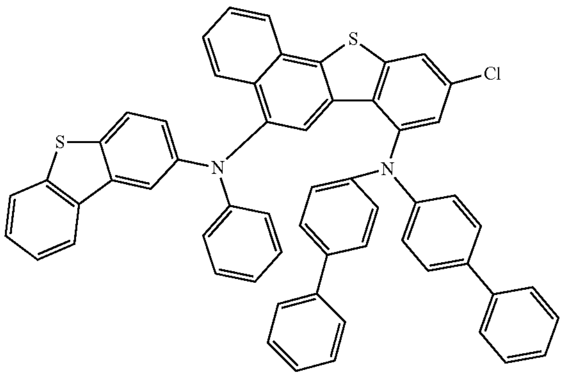
Sub1-98
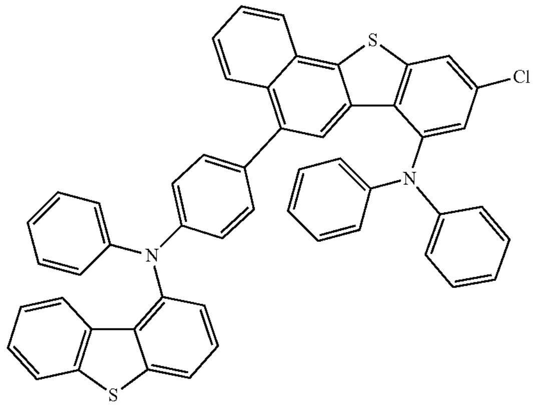
Sub1-99
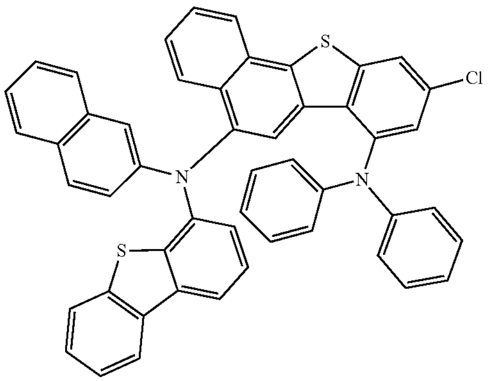
-continued
Sub1-100
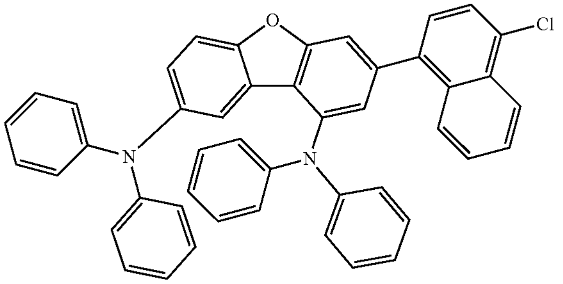
Sub1-101
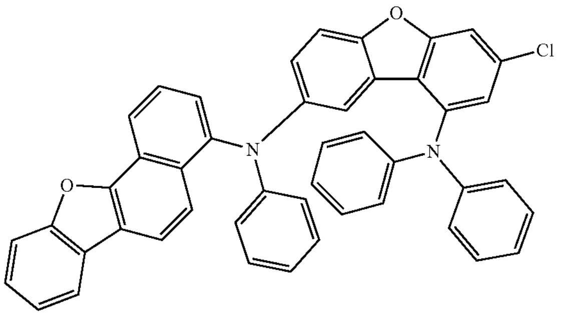
Sub1-102
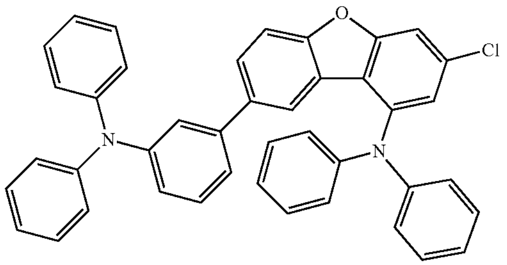
Sub1-103
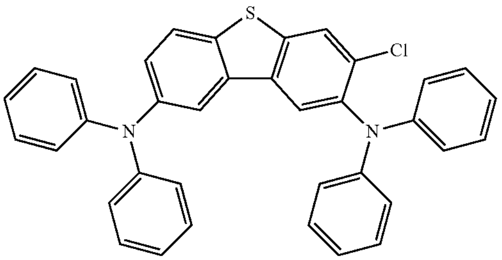
Sub1-104
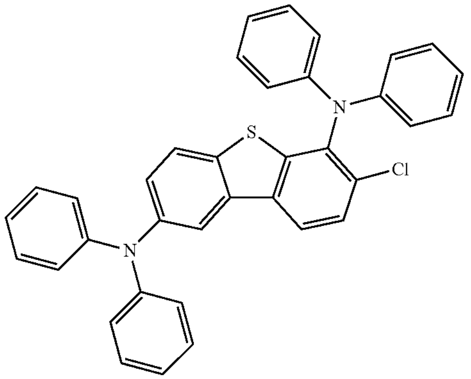

-continued

Sub1-105

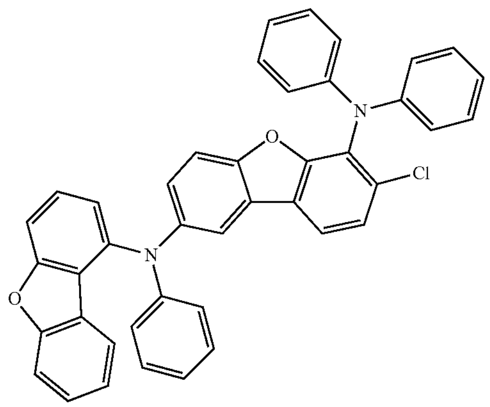

-continued

Sub1-106

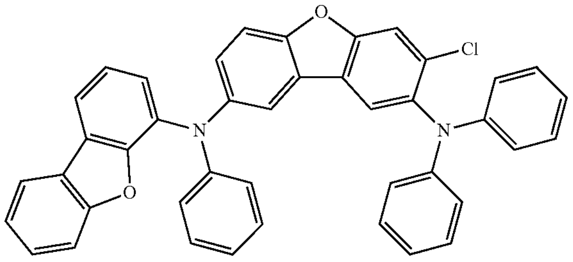

The FD-MS values of the compounds belonging to Sub 1 are shown in Table 2 below.

TABLE 2

| Compound | FD-MS | Compound | FD-MS |
|---|---|---|---|
| Sub 1-1 | m/z = 369.09 ($C_{24}H_{13}ClNO$ = 369.85) | Sub 1-2 | m/z = 445.12 ($C_{30}H_{20}ClNO$ = 445.95) |
| Sub 1-3 | m/z = 450.15 ($C_{30}H_{15}D_5ClNO$ = 450.98) | Sub 1-4 | m/z = 445.12 ($C_{30}H_{20}ClNO$ = 445.95) |
| Sub 1-5 | m/z = 521.15 ($C_{36}H_{24}ClNO$ = 522.04) | Sub 1-6 | m/z = 521.15 ($C_{36}H_{24}ClNO$ = 522.04) |
| Sub 1-7 | m/z = 445.12 ($C_{30}H_{20}ClNO$ = 445.95) | Sub 1-8 | m/z = 383.11 ($C_{25}H_{18}ClNO$ = 383.88) |
| Sub 1-9 | m/z = 445.12 ($C_{30}H_{20}ClNO$ = 445.95) | Sub 1-10 | m/z = 521.15 ($C_{36}H_{24}ClNO$ = 522.04) |
| Sub 1-11 | m/z = 521.15 ($C_{36}H_{24}ClNO$ = 522.04) | Sub 1-12 | m/z = 521.15 ($C_{36}H_{24}ClNO$ = 522.04) |
| Sub 1-13 | m/z = 445.12 ($C_{30}H_{20}ClNO$ = 445.95) | Sub 1-14 | m/z = 445.12 ($C_{30}H_{20}ClNO$ = 445.95) |
| Sub 1-15 | m/z = 445.12 ($C_{30}H_{20}ClNO$ = 445.95) | Sub 1-16 | m/z = 419.11 ($C_{28}H_{18}ClNO$ = 419.91) |
| Sub 1-17 | m/z = 545.15 ($C_{38}H_{24}ClNO$ = 546.07) | Sub 1-18 | m/z = 419.11 ($C_{28}H_{18}ClNO$ = 419.91) |
| Sub 1-19 | m/z = 521.15 ($C_{36}H_{24}ClNO$ = 522.04) | Sub 1-20 | m/z = 383.11 ($C_{25}H_{18}ClNO$ = 383.88) |
| Sub 1-21 | m/z = 387.08 ($C_{24}H_{15}ClFNO$ = 387.84) | Sub 1-22 | m/z = 387.08 ($C_{24}H_{15}ClFNO$ = 387.84) |
| Sub 1-23 | m/z = 383.11 ($C_{25}H_{18}ClNO$ = 383.88) | Sub 1-24 | m/z = 397.12 ($C_{26}H_{20}ClNO$ = 397.90) |
| Sub 1-25 | m/z = 397.12 ($C_{26}H_{20}ClNO$ = 397.90) | Sub 1-26 | m/z = 445.12 ($C_{30}H_{20}ClNO$ = 445.95) |
| Sub 1-27 | m/z = 495.14 ($C_{34}H_{22}ClNO$ = 496.01) | Sub 1-28 | m/z = 495.14 ($C_{34}H_{22}ClNO$ = 496.01) |
| Sub 1-29 | m/z = 500.17 ($C_{34}H_{17}D_5ClNO$ = 501.04) | Sub 1-30 | m/z = 445.12 ($C_{30}H_{20}ClNO$ = 445.95) |
| Sub 1-31 | m/z = 597.19 ($C_{42}H_{28}ClNO$ = 598.14) | Sub 1-32 | m/z = 495.14 ($C_{34}H_{22}ClNO$ = 496.01) |
| Sub 1-33 | m/z = 521.15 ($C_{36}H_{24}ClNO$ = 522.04) | Sub 1-34 | m/z = 536.17 ($C_{38}H_{25}ClN_2O$ = 537.06) |
| Sub 1-35 | m/z = 612.20 ($C_{42}H_{29}ClN_2O$ = 613.16) | Sub 1-36 | m/z = 612.20 ($C_{42}H_{29}ClN_2O$ = 613.16) |
| Sub 1-37 | m/z = 612.20 ($C_{42}H_{29}ClN_2O$ = 613.16) | Sub 1-38 | m/z = 688.23 ($C_{48}H_{33}ClN_2O$ = 689.26) |
| Sub 1-39 | m/z = 612.20 ($C_{42}H_{29}ClN_2O$ = 613.16) | Sub 1-40 | m/z = 445.12 ($C_{30}H_{20}ClNO$ = 445.95) |
| Sub 1-41 | m/z = 383.11 ($C_{25}H_{18}ClNO$ = 383.88) | Sub 1-42 | m/z = 495.14 ($C_{34}H_{22}ClNO$ = 496.01) |
| Sub 1-43 | m/z = 509.15 ($C_{35}H_{24}ClNO$ = 510.03) | Sub 1-44 | m/z = 571.17 ($C_{40}H_{26}ClNO$ = 572.10) |
| Sub 1-45 | m/z = 521.15 ($C_{36}H_{24}ClNO$ = 522.04) | Sub 1-46 | m/z = 571.17 ($C_{40}H_{26}ClNO$ = 572.10) |
| Sub 1-47 | m/z = 535.17 ($C_{37}H_{26}ClNO$ = 536.07) | Sub 1-48 | m/z = 383.11 ($C_{25}H_{18}ClNO$ = 383.88) |
| Sub 1-49 | m/z = 445.12 ($C_{30}H_{20}ClNO$ = 445.95) | Sub 1-50 | m/z = 445.12 ($C_{30}H_{20}ClNO$ = 445.95) |
| Sub 1-51 | m/z = 551.11 ($C_{36}H_{22}ClNOS$ = 552.09) | Sub 1-52 | m/z = 475.08 ($C_{30}H_{18}ClNOS$ = 475.99) |
| Sub 1-53 | m/z = 469.12 ($C_{32}H_{20}ClNO$ = 469.97) | Sub 1-54 | m/z = 419.11 ($C_{28}H_{18}ClNO$ = 419.91) |
| Sub 1-55 | m/z = 585.15 ($C_{40}H_{24}ClNO_2$ = 586.09) | Sub 1-56 | m/z = 552.14 ($C_{36}H_{25}ClN_2S$ = 553.12) |
| Sub 1-57 | m/z = 658.13 ($C_{42}H_{27}ClN_2S_2$ = 659.26) | Sub 1-58 | m/z = 658.13 ($C_{42}H_{27}ClN_2S_2$ = 659.26) |
| Sub 1-59 | m/z = 642.15 ($C_{42}H_{27}ClN_2OS$ = 643.20) | Sub 1-60 | m/z = 642.15 ($C_{42}H_{27}ClN_2OS$ = 643.20) |
| Sub 1-61 | m/z = 658.13 ($C_{42}H_{27}ClN_2S_2$ = 659.26) | Sub 1-62 | m/z = 810.19 ($C_{54}H_{35}ClN_2S_2$ = 811.46) |
| Sub 1-63 | m/z = 658.13 ($C_{42}H_{27}ClN_2S_2$ = 659.26) | Sub 1-64 | m/z = 708.15 ($C_{46}H_{29}ClN_2S_2$ = 709.32) |
| Sub 1-65 | m/z = 642.15 ($C_{42}H_{27}ClN_2OS$ = 643.20) | Sub 1-66 | m/z = 642.15 ($C_{42}H_{27}ClN_2OS$ = 643.20) |
| Sub 1-67 | m/z = 642.15 ($C_{42}H_{27}ClN_2OS$ = 643.20) | Sub 1-68 | m/z = 692.17 ($C_{46}H_{29}ClN_2OS$ = 693.26) |
| Sub 1-69 | m/z = 628.17 ($C_{42}H_{29}ClN_2S$ = 629.22) | Sub 1-70 | m/z = 678.19 ($C_{46}H_{31}ClN_2S$ = 679.28) |
| Sub 1-71 | m/z = 728.21 ($C_{50}H_{33}ClN_2S$ = 729.34) | Sub 1-72 | m/z = 678.19 ($C_{46}H_{31}ClN_2S$ = 679.28) |
| Sub 1-73 | m/z = 629.17 ($C_{41}H_{28}ClN_3S$ = 630.21) | Sub 1-74 | m/z = 680.18 ($C_{44}H_{29}ClN_4S$ = 681.25) |
| Sub 1-75 | m/z = 668.21 ($C_{45}H_{33}ClN_2S$ = 669.28) | Sub 1-76 | m/z = 790.22 ($C_{55}H_{35}ClN_2S$ = 791.41) |
| Sub 1-77 | m/z = 717.20 ($C_{48}H_{32}ClN_3S$ = 718.32) | Sub 1-78 | m/z = 718.18 ($C_{48}H_{31}ClN_2OS$ = 719.30) |
| Sub 1-79 | m/z = 792.24 ($C_{55}H_{37}ClN_2S$ = 793.43) | Sub 1-80 | m/z = 570.13 ($C_{36}H_{24}ClFN_2S$ = 571.11) |
| Sub 1-81 | m/z = 578.16 ($C_{38}H_{27}ClN_2S$ = 579.16) | Sub 1-82 | m/z = 704.21 ($C_{48}H_{33}ClN_2S$ = 705.32) |
| Sub 1-83 | m/z = 734.16 ($C_{48}H_{31}ClN_2S_2$ = 735.36) | Sub 1-84 | m/z = 734.16 ($C_{48}H_{31}ClN_2S_2$ = 735.36) |
| Sub 1-85 | m/z = 628.17 ($C_{42}H_{29}ClN_2S$ = 629.22) | Sub 1-86 | m/z = 602.16 ($C_{49}H_{27}ClN_2S$ = 603.18) |
| Sub 1-87 | m/z = 586.18 ($C_{40}H_{27}ClN_2O$ = 587.12) | Sub 1-88 | m/z = 676.19 ($C_{46}H_{29}ClN_2O_2$ = 677.20) |
| Sub 1-89 | m/z = 828.25 ($C_{58}H_{37}ClN_2O_2$ = 829.40) | Sub 1-90 | m/z = 692.17 ($C_{46}H_{29}ClN_2OS$ = 693.26) |
| Sub 1-91 | m/z = 818.22 ($C_{56}H_{35}ClN_2OS$ = 819.42) | Sub 1-92 | m/z = 708.15 ($C_{46}H_{29}ClN_2S_2$ = 709.32) |
| Sub 1-93 | m/z = 718.22 ($C_{49}H_{35}ClN_2S$ = 719.34) | Sub 1-94 | m/z = 692.17 ($C_{46}H_{29}ClN_2OS$ = 693.26) |
| Sub 1-95 | m/z = 692.17 ($C_{46}H_{29}ClN_2OS$ = 693.26) | Sub 1-96 | m/z = 708.15 ($C_{46}H_{29}ClN_2S_2$ = 709.32) |
| Sub 1-97 | m/z = 860.21 ($C_{58}H_{37}ClN_2S_2$ = 861.52) | Sub 1-98 | m/z = 784.18 ($C_{52}H_{33}ClN_2S_2$ = 785.42) |
| Sub 1-99 | m/z = 758.16 ($C_{50}H_{31}ClN_2S_2$ = 759.38) | Sub 1-100 | m/z = 662.21 ($C_{46}H_{31}ClN_2O$ = 663.22) |
| Sub 1-101 | m/z = 676.19 ($C_{46}H_{29}ClN_2O_2$ = 677.20) | Sub 1-102 | m/z = 612.20 ($C_{42}H_{29}ClN_2O$ = 613.16) |
| Sub 1-103 | m/z = 552.14 ($C_{36}H_{25}ClN_2S$ = 553.12) | Sub 1-104 | m/z = 552.14 ($C_{36}H_{25}ClN_2S$ = S53.12) |
| Sub 1-105 | m/z = 626.18 ($C_{42}H_{27}ClN_2O_2$ = 627.14) | Sub 1-106 | m/z = 626.18 ($C_{42}H_{27}ClN_2O_2$ = 627.14) |

Synthesis Example of Sub 1

Sub 1 may be synthesized by the reaction route of Reaction Scheme 2 below, but there is no limitation thereto.

<Reaction Scheme 2>

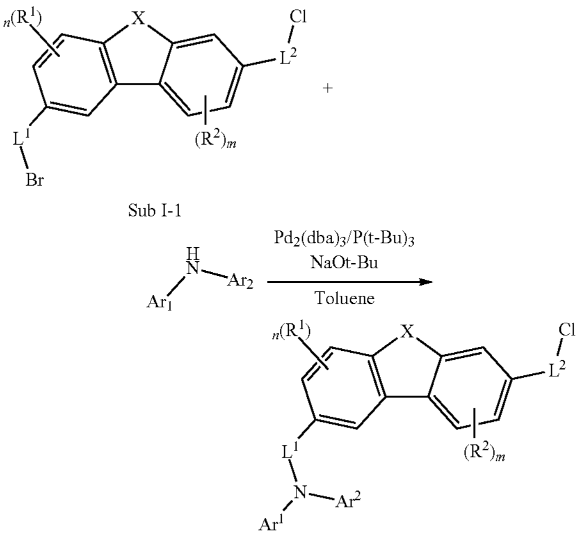

Sub I-1

Sub 1

1. Synthesis Example of Sub 1-1

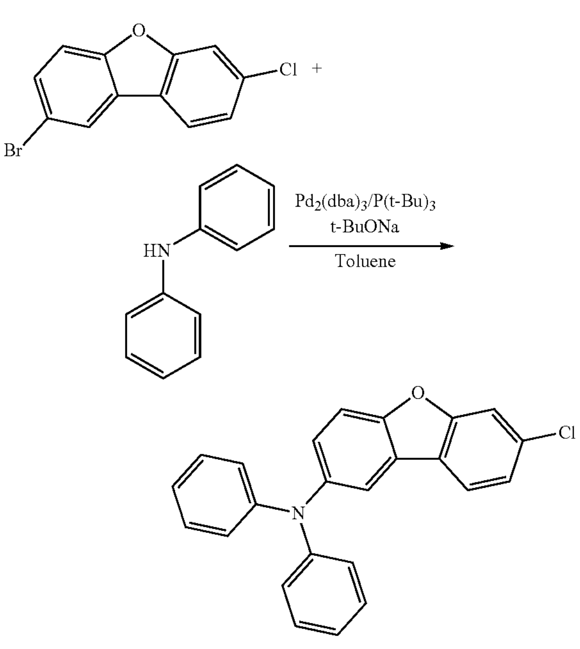

Sub 1-1

After putting 2-bromo-7-chlorodibenzo[b,d]furan (20.0 g, 71.1 mmol), diphenylamine (10.0 g, 59.2 mmol), $Pd_2(dba)_3$ (1.63 g, 1.78 mmol), $P(t\text{-}Bu)_3$ (50 wt % Sol.) (1.44 mL, 3.55 mmol) and t-BuONa (11.4 g, 118 mmol) in a round bottom flask, anhydrous toluene (200 mL) was added thereto and the reaction was carried out for 2 hours. When the reaction was completed, the reaction product was separated by column chromatography to obtain 15.3 g of Compound Sub 1-1. (yield: 70%)

2. Synthesis Example of Sub 1-16

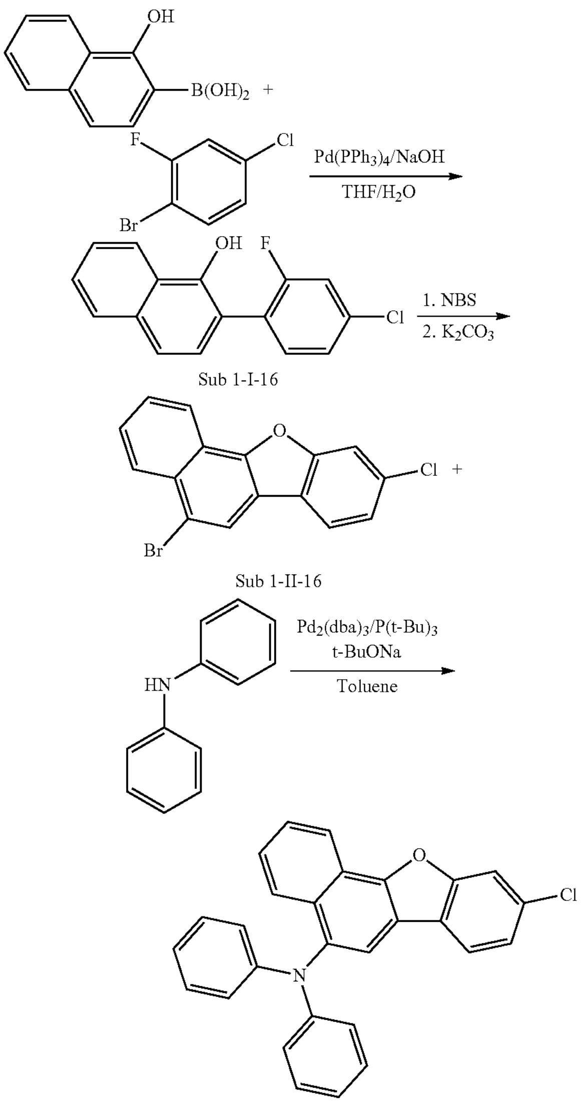

Sub 1-I-16

Sub 1-II-16

Sub 1-16

(1) Synthesis of Sub1-I-16

After putting (1-hydroxynaphthalen-2-yl)boronic acid (50 g, 266 mmol), 1-bromo-4-chloro-2-fluorobenzene (58.5 g, 279 mmol), $Pd(PPh_3)_4$ (9.22 g, 7.98 mmol) and NaOH (31.9 g, 798 mmol) in a round bottom flask, THF (880 mL) and $H_2O$ (220 mL) were added thereto and the reaction was carried overnight. When the reaction was completed, the reaction product was separated by column chromatography to obtain 51.5 g of Compound Sub 1-I-16. (yield: 71%)

(2) Synthesis of Sub1-II-16

After putting DMF (630 ml), Sub1-I-16 (51.5 g, 189 mmol) and NBS (35.3 g, 198 mmol) in a round bottom flask, the mixture was stirred for 8 hours. The reaction-terminated solution was washed with water, extracted with methylene chloride and concentrated. After the concentrate was dissolved in NMP (600 ml), $K_2CO_3$ (49.6 g, 360 mmol) was added and the mixture was stirred for 3 hours under reflux. When the reaction was completed, the reaction product was washed with water, extracted with methylene chloride and concentrated. Thereafter, the concentrate was recrystallized using toluene to obtain 44 g of Compound Sub 1-II-16. (yield: 70%)

(3) Synthesis of Sub1-16

After putting Sub1-II-16 (44 g, 133 mmol), diphenylamine (18.7 g, 111 mmol), $Pd_2(dba)_3$ (3.0 g, 3.32 mmol), $P(t-Bu)_3$ (50 wt % Sol.) (2.68 mL, 6.63 mmol) and t-BuONa (21.3 g, 221 mmol) in a round bottom flask, anhydrous toluene (370 mL) was added thereto and the reaction was carried out for 2 hours. When the reaction was completed, the reaction product was separated by column chromatography to obtain 40 g of Compound Sub 1-16. (yield: 72%)

3. Synthesis Example of Sub 1-19

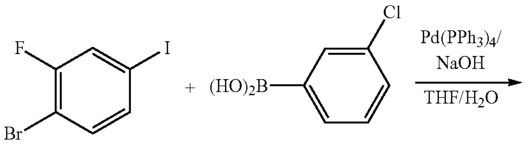

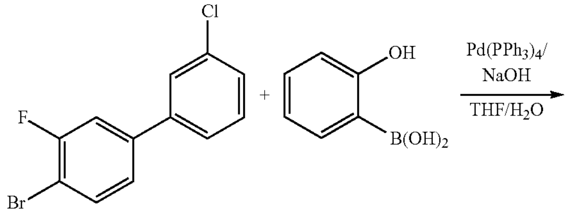

Sub 1-I-19

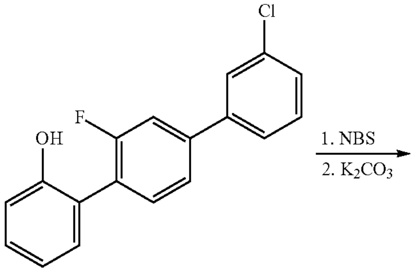

Sub 1-II-19

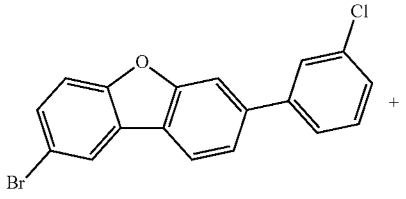

Sub 1-III-19

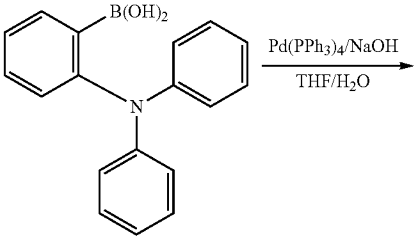

-continued

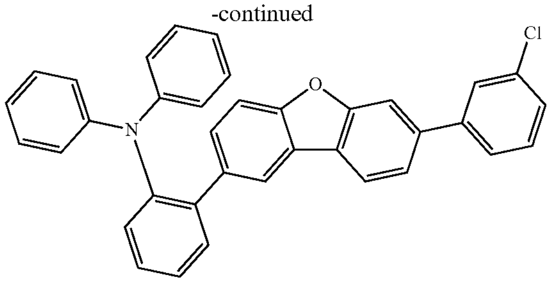

Sub 1-19

(1) Synthesis of Sub1-I-19

After putting 1-bromo-2-fluoro-4-iodobenzene (10 g, 33.2 mmol), (3-chlorophenyl)boronic acid (5.2 g, 33.2 mmol), $Pd(PPh_3)_4$ (1.15 g, 1.00 mmol) and NaOH (4 g, 99.7 mmol) in a round bottom flask, THF (110 mL) and $H_2O$ (30 mL) were added thereto and the reaction was carried overnight. When the reaction was completed, the reaction product was separated by column chromatography to obtain 8 g of Compound Sub 1-I-19. (yield: 85%)

(2) Synthesis of Sub1-II-19

After putting Sub 1-I-19 (8 g, 28 mmol), (2-hydroxyphenyl)boronic acid (3.86 g, 28 mmol), $Pd(PPh_3)_4$ (0.97 g, 0.84 mmol) and NaOH (3.36 g, 84.1 mmol) in a round bottom flask, THF (90 mL) and $H_2O$ (23 mL) were added thereto and the reaction was carried overnight. When the reaction was completed, the reaction product was separated by column chromatography to obtain 6.9 g of Compound Sub 1-II-19. (yield: 83%)

(3) Synthesis of Sub1-III-19

After putting DMF (70 ml), Sub1-II-19 (6.9 g, 23.2 mmol) and NBS (4.33 g, 24.4 mmol) in a round bottom flask, the mixture was stirred for 8 hours. The reaction-terminated solution was washed with water, extracted with methylene chloride and concentrated. After the intermediate was dissolved in NMP (70 ml), $K_2CO_3$ (6.09 g, 44.1 mmol) was added and the mixture was stirred for 3 hours under reflux. The reaction-terminated solution was washed with water, extracted with methylene chloride and concentrated. Thereafter, the concentrate was recrystallized using toluene to obtain 6.4 g of Compound Sub 1-III-19. (yield: 77%)

(4) Synthesis of Sub1-19

After putting Sub 1-III-19 (6.4 g, 17.9 mmol), (2-(diphenylamino)phenyl)boronic acid (5.17 g, 17.9 mmol), $Pd(PPh_3)_4$ (0.62 g, 0.54 mmol) and NaOH (2.15 g, 53.7 mmol) in a round bottom flask, THF (60 mL) and $H_2O$ (15 mL) were added thereto and the reaction was carried overnight. When the reaction was completed, the reaction product was separated by column chromatography to obtain 7.9 g of Compound Sub 1-19. (yield: 85%)

4. Synthesis Example of Sub 1-34

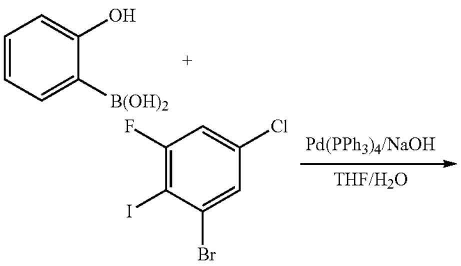

-continued

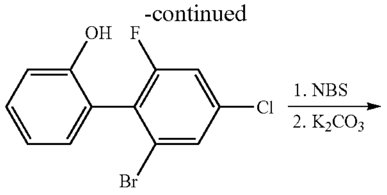

Sub 1-I-34

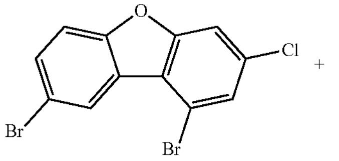

Sub 1-II-34

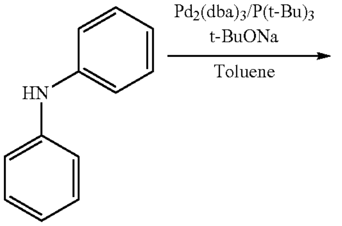

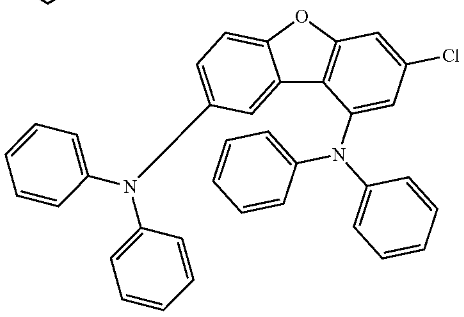

Sub 1-34

(1) Synthesis of Sub1-I-34

After putting (2-hydroxyphenyl)boronic acid (20 g, 145 mmol), 1-bromo-5-chloro-3-fluoro-2-iodobenzene (48.6 g, 145 mmol), $Pd(PPh_3)_4$ (5.03 g, 4.35 mmol), NaOH (17.4 g, 435 mmol) in a round bottom flask, THF (480 mL) and $H_2O$ (120 mL) were added thereto and the reaction was carried overnight. When the reaction was completed, the reaction product was separated by column chromatography to obtain 32.4 g of Compound Sub 1-1-34. (yield: 74%)

(2) Synthesis of Sub1-II-34

After putting DMF (350 ml), Sub1-I-34 (32.4 g, 107 mmol) and NBS (20.0 g, 112 mmol) in a round bottom flask, the mixture was stirred for 8 hours. The reaction-terminated solution was washed with water, extracted with methylene chloride and concentrated. After the intermediate was dissolved in NMP (350 ml), $K_2CO_3$ (28.1 g, 203 mmol) was added and the mixture was stirred for 3 hours under reflux. The reaction-terminated solution was washed with water, extracted with methylene chloride and concentrated. Thereafter, the concentrate was recrystallized using toluene to obtain 27 g of Compound Sub 1-II-34. (yield: 70%)

(3) Synthesis of Sub1-34

After putting Sub1-II-34 (27 g, 74.9 mmol), diphenylamine (25.4 g, 150 mmol), $Pd_2(dba)_3$ (2.06 g, 2.25 mmol), $P(t-Bu)_3$ (50 wt % Sol.) (1.82 mL, 4.49 mmol) and t-BuONa (14.4 g, 150 mmol) in a round bottom flask, anhydrous toluene (250 mL) was added thereto and the reaction was carried out for 2 hours. When the reaction was completed, the reaction product was separated by column chromatography to obtain 20.5 g of Compound Sub 1-34. (yield: 51%)

5. Synthesis Example of Sub 1-56

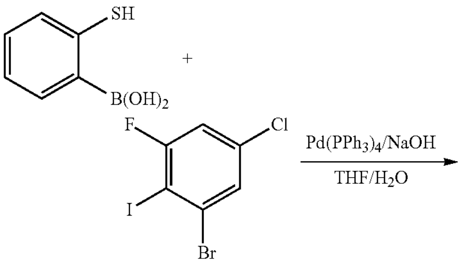

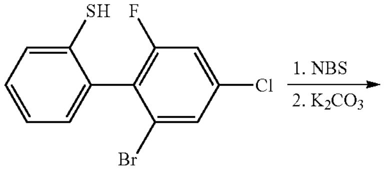

Sub 1-I-56

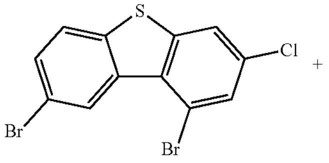

Sub 1-II-56

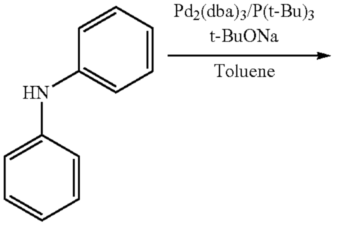

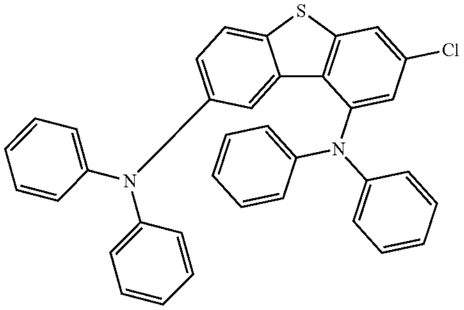

Sub 1-56

(1) Synthesis of Sub1-I-56

After putting (2-mercaptophenyl)boronic acid (15 g, 97.4 mmol), 1-bromo-5-chloro-3-fluoro-2-iodobenzene (32.67 g, 97.4 mmol), $Pd(PPh_3)_4$ (3.38 g, 2.92 mmol) and NaOH (11.69 g, 292.23 mmol) in a round bottom flask, THF (400 mL) and $H_2O$ (100 mL) were added thereto and the reaction was carried overnight. When the reaction was completed, the reaction product was separated by column chromatography to obtain 22.27 g of Compound Sub 1-I-56. (yield: 72%)

(2) Synthesis of Sub1-II-56

After putting DMF (250 ml), Sub1-I-56 (22 g, 69.27 mmol) and NBS (12.95 g, 72.73 mmol) in a round bottom flask, the mixture was stirred for 8 hours. The reaction-terminated solution was washed with water, extracted with methylene chloride and concentrated. After the intermediate was dissolved in NMP (250 ml), $K_2CO_3$ (19.15 g, 138.54 mmol) was added and the mixture was stirred for 3 hours under reflux. The reaction-terminated solution was washed with water, extracted with methylene chloride and concentrated. Thereafter, the concentrate was recrystallized using toluene to obtain 13.4 g of Compound Sub 1-II-56. (yield: 65%)

(3) Synthesis of Sub1-56

After putting Sub1-II-56 (13 g, 34.53 mmol), diphenylamine (11.69 g, 69.06 mmol), $Pd_2(dba)_3$ (0.95 g, 1.04 mmol), $P(t\text{-}Bu)_3$ (50 wt % Sol.) (1.67 mL, 4.14 mmol) and t-BuONa (6.64 g, 69.06 mmol) in a round bottom flask, anhydrous toluene (150 mL) was added thereto and the reaction was carried out for 2 hours. When the reaction was completed, the reaction product was separated by column chromatography to obtain 11.27 g of Compound Sub 1-56. (yield: 59%)

6. Synthesis Example of Sub 1-61

<Reaction Scheme 8>

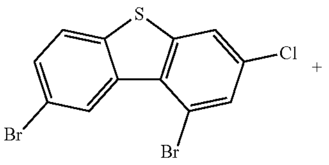

Sub 1-II-56

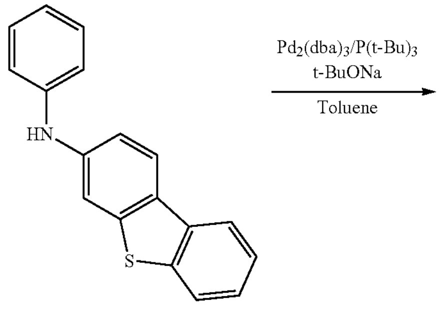

Sub 2-3

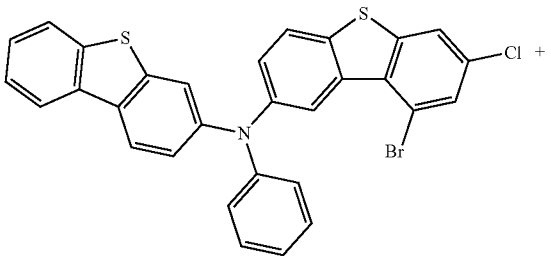

Sub 1-I-61

-continued

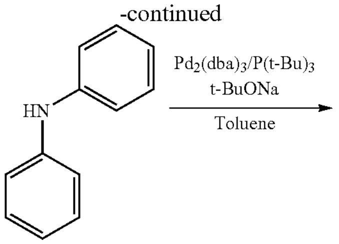

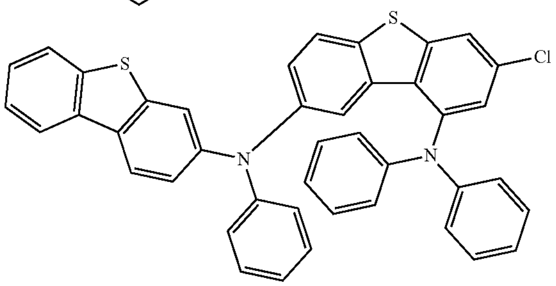

Sub 1-61

(1) Synthesis of Sub1-I-61

After putting Sub1-II-56 (10 g, 26.56 mmol), Sub2-3 (7.31 g, 26.56 mmol), $Pd_2(dba)_3$ (0.73 g, 0.80 mmol), $P(t\text{-}Bu)_3$ (50 wt % Sol.) (0.64 mL, 1.59 mmol) and t-BuONa (5.11 g, 53.12 mmol) in a round bottom flask, anhydrous toluene (100 mL) was added thereto and the reaction was carried out for 3 hours. When the reaction was completed, the reaction product was separated by column chromatography to obtain 8.04 g of Compound Sub 1-1-61. (yield: 53%)

(2) Synthesis of Sub1-61

After putting Sub1-I-61 (8.04 g, 14.08 mmol), diphenylamine (2.38 g, 14.08 mmol), $Pd_2(dba)_3$ (0.39 g, 0.42 mmol), $P(t\text{-}Bu)_3$ (50 wt % Sol.) (0.34 mL, 0.84 mmol) and t-BuONa (2.71 g, 28.16 mmol) in a round bottom flask, anhydrous toluene (100 mL) was added thereto and the reaction was carried out for 2 hours. When the reaction was completed, the reaction product was separated by column chromatography to obtain 5.85 g of Compound Sub 1-61. (yield: 63%)

7. Synthesis Example of Sub 1-86

<Reaction Scheme 9>

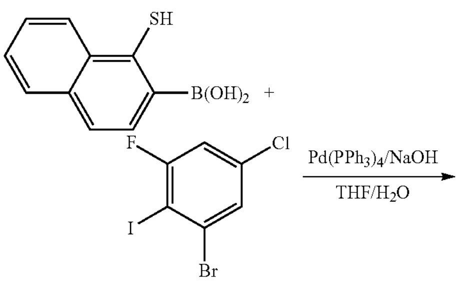

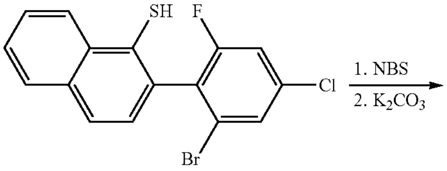

Sub 1-I-86

-continued

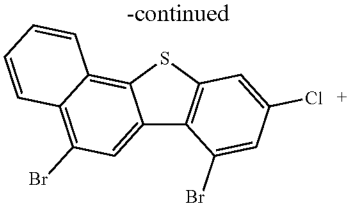

Sub 1-II-86

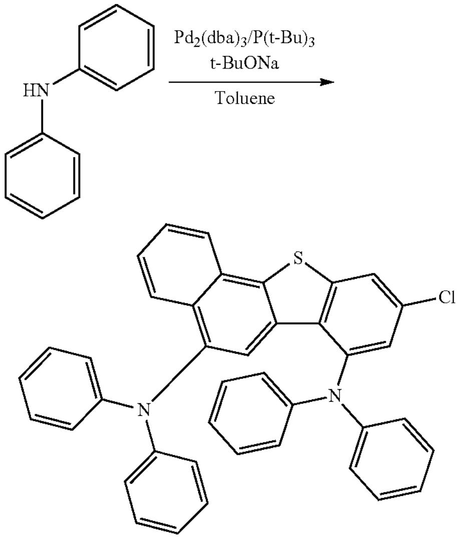

Sub 1-86

(1) Synthesis of Sub1-I-86

After putting (1-mercaptonaphthalen-2-yl)boronic acid (30 g, 147.02 mmol), 1-bromo-4-chloro-2-fluorobenzene (49.3 g, 147.02 mmol), $Pd(PPh_3)_4$ (5.1 g, 4.41 mmol) and NaOH (17.64 g, 441.07 mmol) in a round bottom flask, THF (520 mL) and $H_2O$ (130 mL) were added thereto and the reaction was carried overnight. When the reaction was completed, the reaction product was separated by column chromatography to obtain 34.59 g of Compound Sub 1-I-86. (yield: 64%)

(2) Synthesis of Sub1-II-86

After putting DMF (400 ml), Sub1-I-86 (34.5 g, 93.84 mmol) and NBS (17.54 g, 98.53 mmol) in a round bottom flask, the mixture was stirred for 8 hours. The reaction-terminated solution was washed with water, extracted with methylene chloride and concentrated. Thereafter, the concentrate was dissolved in NMP (400 ml), $K_2CO_3$ (25.94 g, 187.67 mmol) was added and the mixture was stirred for 3 hours under reflux. Thereafter, the reaction-terminated solution was washed with water, extracted with methylene chloride and concentrated. Thereafter, the concentrate was recrystallized using toluene to obtain 28.02 g of Compound Sub 1-II-86. (yield: 70%)

(3) Synthesis of Sub1-86

After putting Sub1-II-86 (28 g, 65.64 mmol), diphenylamine (22.22 g, 131.29 mmol), $Pd_2(dba)_3$ (1.8 g, 1.97 mmol), $P(t\text{-}Bu)_3$ (50 wt % Sol.) (3.19 mL, 7.88 mmol) and t-BuONa (12.62 g, 131.29 mmol) in a round bottom flask, anhydrous toluene (250 mL) was added thereto and the reaction was carried out for 2 hours. When the reaction was completed, the reaction product was separated by column chromatography to obtain 24.15 g of Compound Sub 1-86. (yield: 61%)

Example of Sub 2

The compounds belonging to Sub 2 of Reaction Scheme 1 may be the following compounds, but there is no limitation thereto.

Sub 2-1

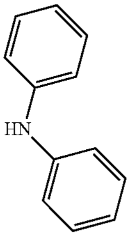

Sub 2-2

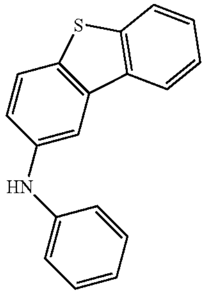

Sub 2-3

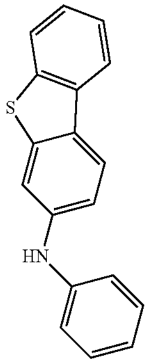

Sub 2-4

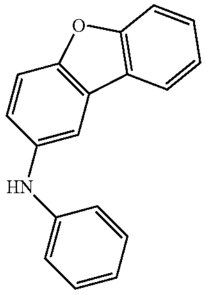

-continued
Sub 2-5
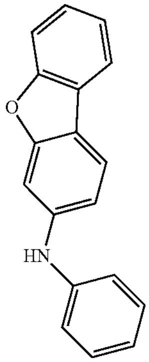
Sub 2-6
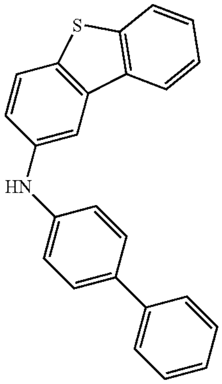
Sub 2-7
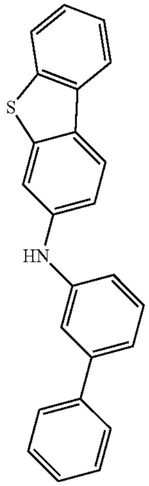
Sub 2-8
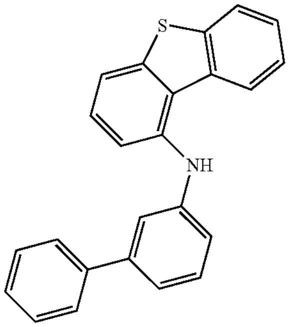
-continued
Sub 2-9
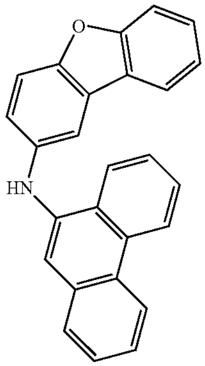
Sub 2-10
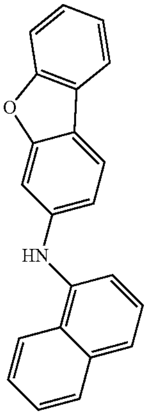
Sub 2-11
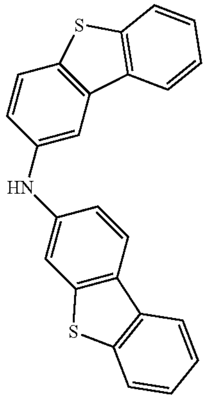

Sub 2-12
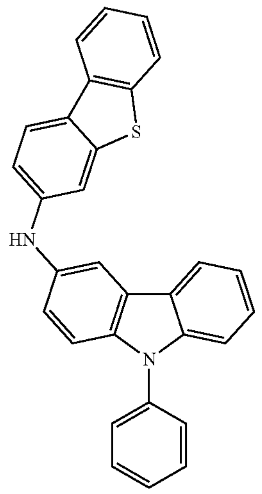
Sub 2-13
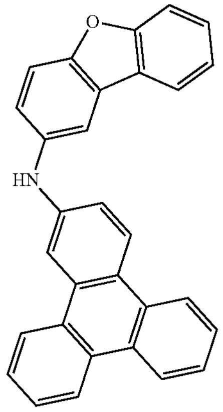
Sub 2-14
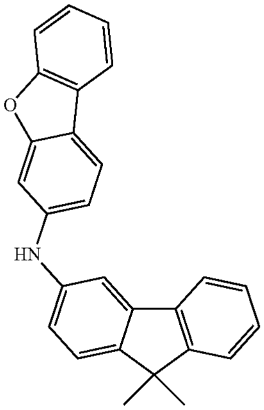
Sub 2-15
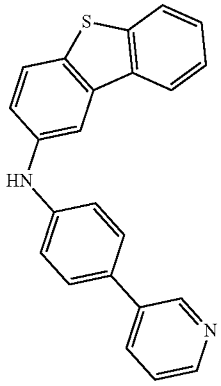
Sub 2-16
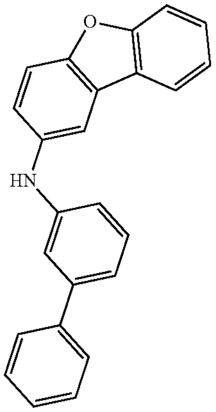
Sub 2-17
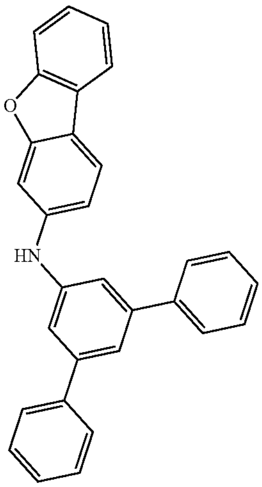
Sub 2-18
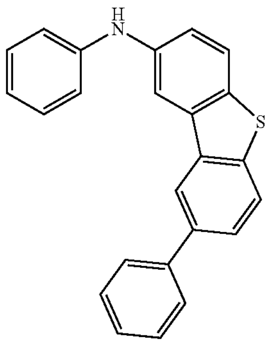

-continued
Sub 2-19
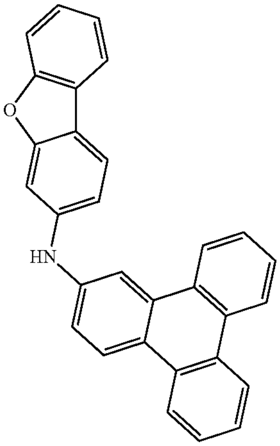
Sub 2-20
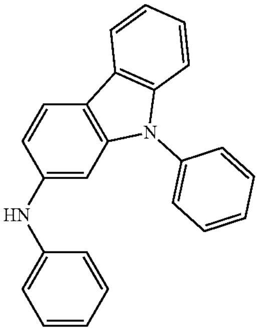
Sub 2-21
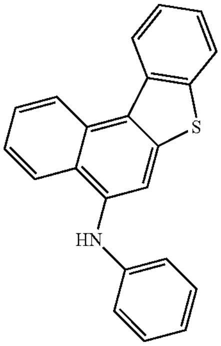
Sub 2-22
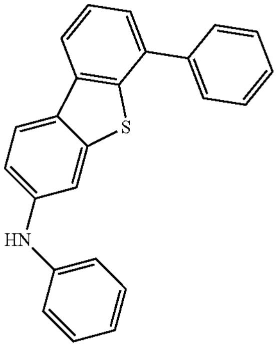
-continued
Sub 2-23
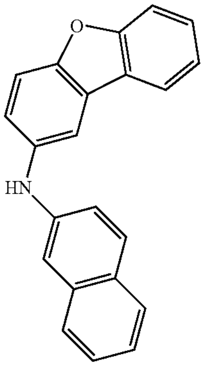
Sub 2-24
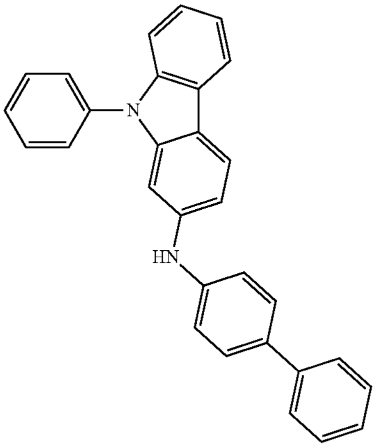
Sub 2-25
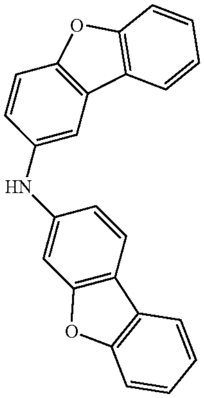

-continued
Sub 2-26
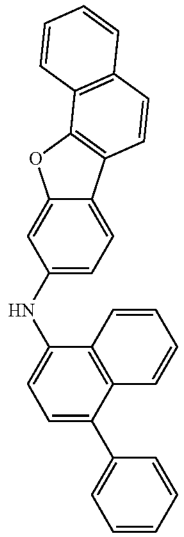
Sub 2-27
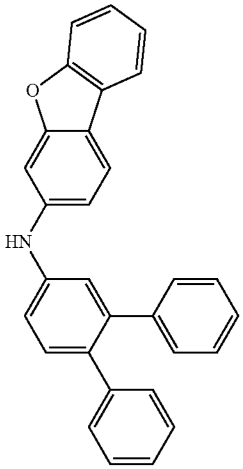
Sub 2-28
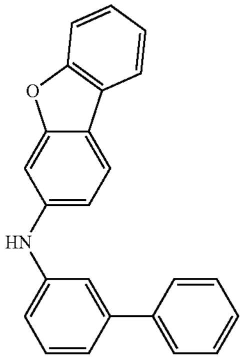
-continued
Sub 2-29
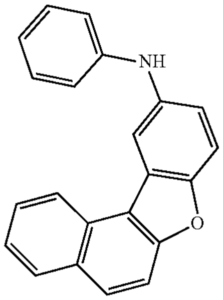
Sub 2-30
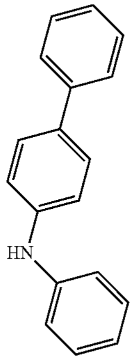
Sub 2-31
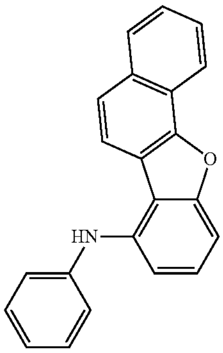
Sub 2-32
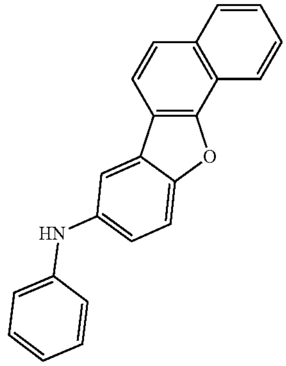
Sub 2-23
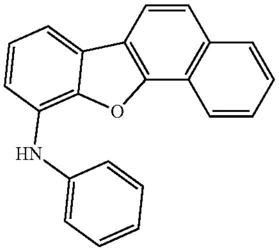

-continued
Sub 2-34
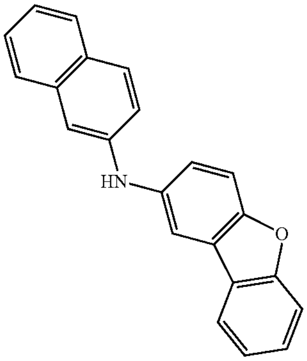
Sub 2-35
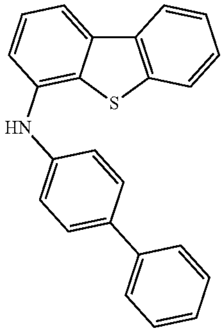
Sub 2-36
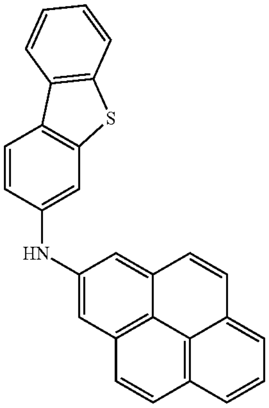
Sub 2-37
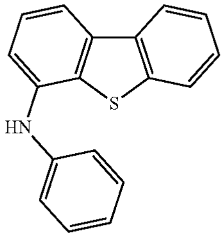
Sub 2-38
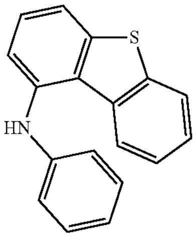
-continued
Sub 2-39
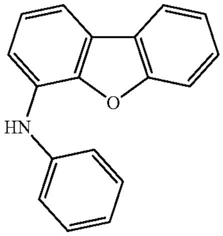
Sub 2-40
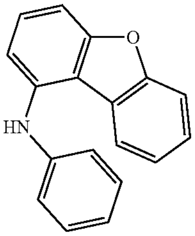
Sub 2-41
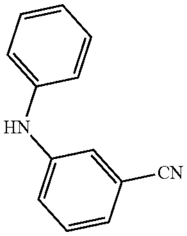
Sub 2-42
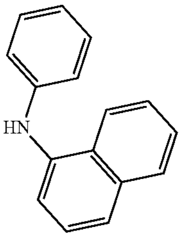
Sub 2-43
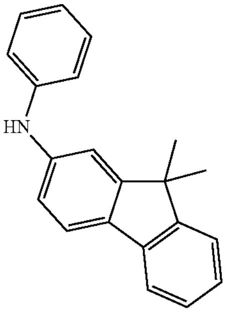
Sub 2-44
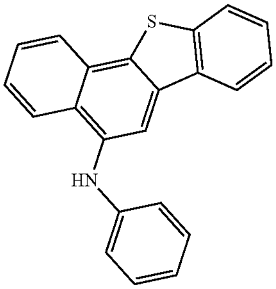

-continued
Sub 2-45
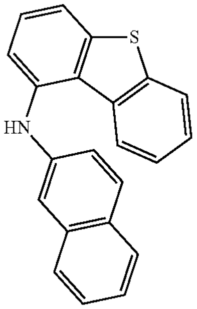
Sub 2-46
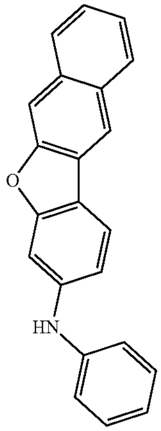
Sub 2-47
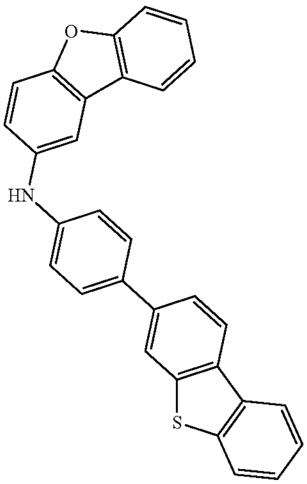
-continued
Sub 2-48
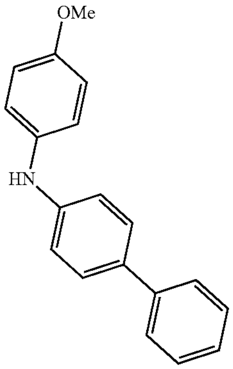
Sub 2-49
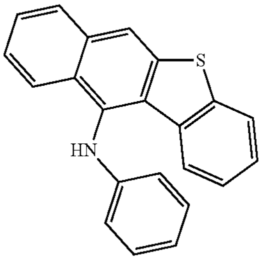
Sub 2-50
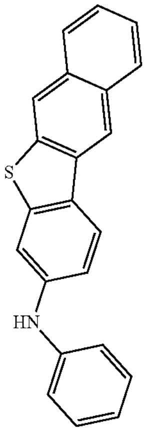
The FD-MS values of the compounds belonging to Sub 2 are shown in Table 3 below.

TABLE 3

| Compound | FD-MS | Compound | FD-MS |
|---|---|---|---|
| Sub 2-1 | m/z = 169.09 ($C_{12}H_{11}N$ = 169.22) | Sub 2-2 | m/z = 275.08($C_{18}H_{13}NS$ = 275.37) |
| Sub 2-3 | m/z = 275.08 ($C_{18}H_{13}NS$ = 275.37) | Sub 2-4 | m/z = 259.10 ($C_{18}H_{13}NO$ = 259.31) |
| Sub 2-5 | m/z = 259.10 ($C_{18}H_{13}NO$ = 259.31) | Sub 2-6 | m/z = 351.11 ($C_{24}H_{17}NS$ = 351.47) |
| Sub 2-7 | m/z = 351.11 ($C_{24}H_{17}NS$ = 351.47) | Sub 2-8 | m/z = 351.11 ($C_{24}H_{17}NS$ = 351.47) |
| Sub 2-9 | m/z = 359.13 ($C_{26}H_{17}NO$ = 359.43) | Sub 2-10 | m/z = 309.12 ($C_{22}H_{15}NO$ = 309.37) |
| Sub 2-11 | m/z = 309.12 ($C_{22}H_{15}NO$ = 309.37) | Sub 2-12 | m/z = 440.13 ($C_{30}H_{20}N_2S$ = 440.56) |
| Sub 2-13 | m/z = 409.15 ($C_{30}H_{19}NO$ = 409.49) | Sub 2-14 | m/z = 375.16 ($C_{27}H_{21}NO$ = 375.47) |
| Sub 2-15 | m/z = 352.10 ($C_{23}H_{16}N_2S$ = 352.46) | Sub 2-16 | m/z = 335.13 ($C_{24}H_{27}NO$ = 335.41) |
| Sub 2-17 | m/z = 411.16 ($C_{30}H_{21}NO$ = 411.50) | Sub 2-18 | m/z = 351.11 ($C_{24}H_{17}NS$ = 351.47) |
| Sub 2-19 | m/z = 409.15 ($C_{30}H_{19}NO$ = 409.49) | Sub 2-20 | m/z = 334.15($C_{24}H_{18}N_2$ = 334.41) |
| Sub 2-21 | m/z = 325.09 ($C_{22}H_{15}NS$ = 325.43) | Sub 2-22 | m/z = 351.11 ($C_{24}H_{17}NS$ = 351.47) |
| Sub 2-23 | m/z = 309.12 ($C_{22}H_{15}NO$ = 309.37) | Sub 2-24 | m/z = 410.18 ($C_{30}H_{22}N_2$ = 410.52) |
| Sub 2-25 | m/z = 349.11 ($C_{24}H_{15}NO_2$ = 349.39) | Sub 2-26 | m/z = 435.16 ($C_{32}H_{21}NO$ = 435.53) |
| Sub 2-27 | m/z = 411.16 ($C_{30}H_{21}NO$ = 411.50) | Sub 2-28 | m/z = 335.13 ($C_{24}H_{27}NO$ = 335.41) |
| Sub 2-29 | m/z = 309.12 ($C_{22}H_{15}NO$ = 309.37) | Sub 2-30 | m/z = 245.12 ($C_{18}H_{15}N$ = 245.32) |
| Sub 2-31 | m/z = 309.12 ($C_{22}H_{15}NO$ = 309.37) | Sub 2-32 | m/z = 309.12 ($C_{22}H_{15}NO$ = 309.37) |
| Sub 2-33 | m/z = 309.12 ($C_{22}H_{15}NO$ = 309.37) | Sub 2-34 | m/z = 309.12 ($C_{22}H_{15}NO$ = 309.37) |
| Sub 2-35 | m/z = 351.11 ($C_{24}H_{17}NS$ = 351.47) | Sub 2-36 | m/z = 399.11 ($C_{28}H_{17}NS$ = 399.51) |
| Sub 2-37 | m/z = 275.08 ($C_{18}H_{13}NS$ = 275.37) | Sub 2-38 | m/z = 275.08 ($C_{18}H_{13}NS$ = 275.37) |
| Sub 2-39 | m/z = 259.10 ($C_{18}H_{13}NO$ = 259.31) | Sub 2-40 | m/z = 259.10 ($C_{18}H_{13}NO$ = 259.31) |
| Sub 2-41 | m/z = 194.08 ($C_{13}H_{10}N_2$ = 194.24) | Sub 2-42 | m/z = 219.10 ($C_{18}H_{13}N$ = 219.29) |
| Sub 2-43 | m/z = 285.15 ($C_{21}H_{19}N$ = 285.39) | Sub 2-44 | m/z = 325.09 ($C_{22}H_{15}NS$ = 325.43) |
| Sub 2-45 | m/z = 325.09 ($C_{22}H_{15}NS$ = 325.43) | Sub 2-46 | m/z = 309.12 ($C_{22}H_{15}NO$ = 309.37) |
| Sub 2-47 | m/z = 441.12 ($C_{30}H_{19}NOS$ = 441.55) | Sub 2-48 | m/z = 275.13 ($C_{19}H_{17}NO$ = 275.35) |
| Sub 2-49 | m/z = 325.09 ($C_{22}H_{15}NS$ = 325.43) | Sub 2-50 | m/z = 325.09 ($C_{22}H_{15}NS$ = 325.43) |

Synthesis Example of Sub 2

1. Synthesis Example of Sub 2-1

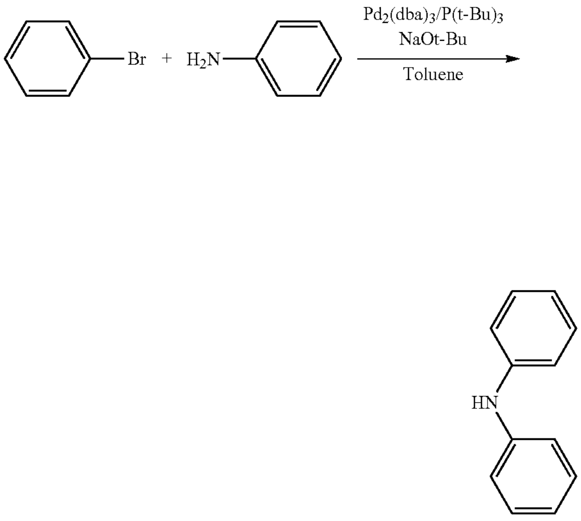

Sub 2-1

After bromobenzene (40.68 g, 259.09 mmol) was dissolved in toluene (1360 ml) in a round bottom flask, aniline (26.54 g, 285.00 mmol), $Pd_2(dba)_3$ (7.12 g, 7.77 mmol), 50% $P(t\text{-}Bu)_3$ (10.1 ml, 20.73 mmol) and NaOt-Bu (74.70 g, 777.28 mmol) were added the solution and the mixture was stirred at 80° C. When the reaction was completed, the reaction product was extracted with $CH_2Cl_2$ and water. The organic layer was dried with $MgSO_4$ and concentrated. The concentrate was passed through a silica gel column and recrystallized to obtain 32.88 g (yield: 75%) of Sub 2-1.

2. Synthesis Example of Sub 2-2

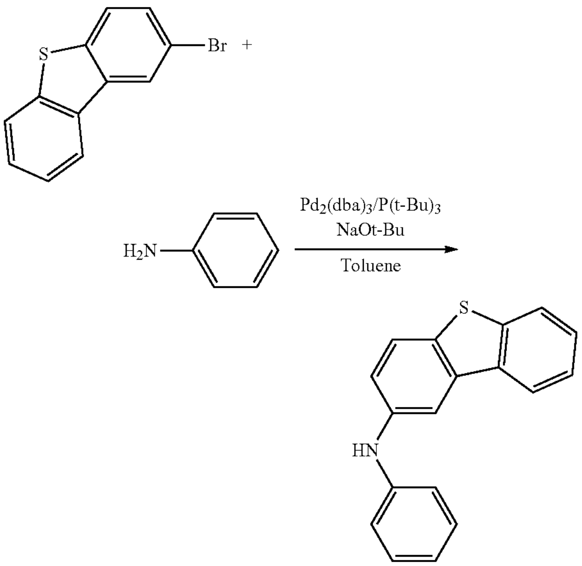

Sub 2-2

After 2-bromodibenzo[b,d]thiophene (38.11 g, 144.82 mmol) was dissolved in toluene (760 ml) in a round bottom flask, aniline (14.84 g, 159.30 mmol), $Pd_2(dba)_3$ (3.98 g, 4.34 mmol), 50% $P(t\text{-}Bu)_3$ (5.6 ml, 11.59 mmol) and NaOt-Bu (41.76 g, 434.47 mmol) were added the solution and the mixture was stirred at 80° C. When the reaction was completed, the reaction product was extracted with $CH_2Cl_2$ and water. The organic layer was dried with $MgSO_4$ and concentrated. The concentrate was passed through a silica gel column and recrystallized to obtain 30.7 g (yield: 77%) of Sub 2-2.

3. Synthesis Example of Sub 2-15

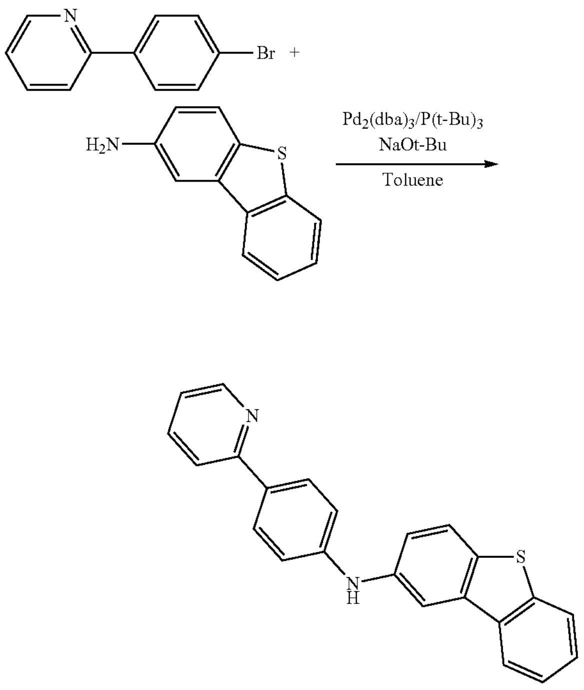

Sub 2-15

After 2-(4-bromophenyl)pyridine (10.53 g, 44.98 mmol) was dissolved in toluene (315 ml) in a round bottom flask, dibenzo[b,d]thiophen-2-amine (9.9 g, 49.48 mmol), $Pd_2(dba)_3$ (1.24 g, 1.35 mmol), 50% $P(t\text{-}Bu)_3$ (1.8 ml, 3.60 mmol) and NaOt-Bu (12.97 g, 134.95 mmol) were added the solution and the mixture was stirred at 80° C. When the reaction was completed, the reaction product was extracted with $CH_2Cl_2$ and water. The organic layer was dried with $MgSO_4$ and concentrated. The concentrate was passed through a silica gel column and recrystallized to obtain 8.32 g (yield: 53%) of Sub 2-15.

4. Synthesis Example of Sub 2-20

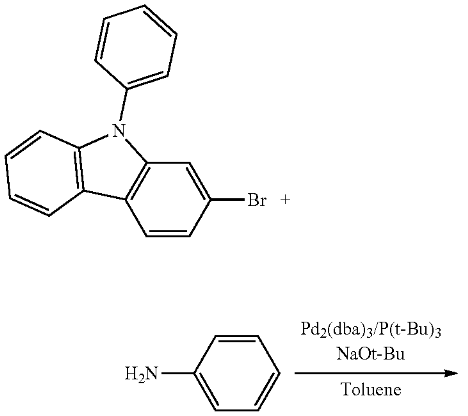

-continued

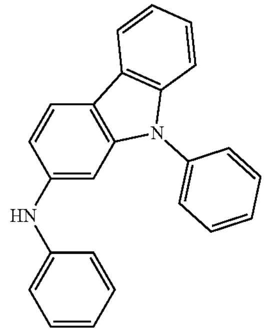

Sub 2-20

After 2-bromo-9-phenyl-9H-carbazole (14.71 g, 45.65 mmol) was dissolved in toluene (320 ml) in a round bottom flask, aniline (4.68 g, 50.22 mmol), $Pd_2(dba)_3$ (1.25 g, 1.37 mmol), 50% $P(t\text{-}Bu)_3$ (1.8 ml, 3.65 mmol) and NaOt-Bu (13.16 g, 136.96 mmol) were added the solution and the mixture was stirred at 80° C. When the reaction was completed, the reaction product was extracted with $CH_2Cl_2$ and water. The organic layer was dried with $MgSO_4$ and concentrated. The concentrate was passed through a silica gel column and recrystallized to obtain 10.99 g (yield: 72%) of Sub 2-20.

5. Synthesis Example of Sub 2-30

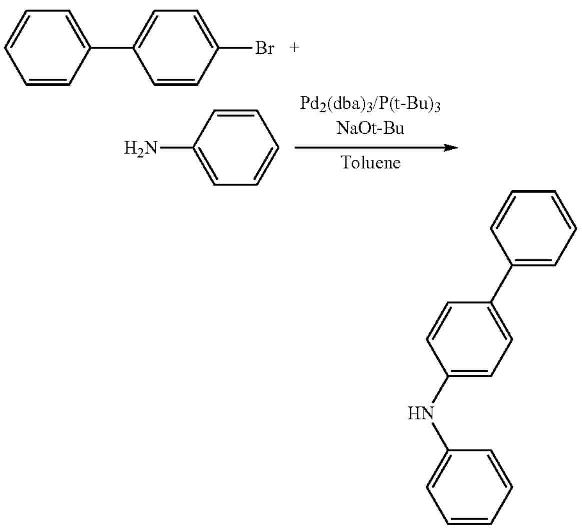

Sub 2-30

After 4-bromo-1,1'-biphenyl (23.65 g, 101.46 mmol) was dissolved in toluene (710 ml) in a round bottom flask, aniline (10.39 g, 111.60 mmol), $Pd_2(dba)_3$ (2.79 g, 3.04 mmol), 50% $P(t\text{-}Bu)_3$ (4.0 ml, 8.12 mmol) and NaOt-Bu (29.25 g, 304.38 mmol) were added the solution and the mixture was stirred at 80° C. When the reaction was completed, the reaction product was extracted with $CH_2Cl_2$ and water. The organic layer was dried with $MgSO_4$ and concentrated. The concentrate was passed through a silica gel column and recrystallized to obtain 20.66 g (yield: 83%) of Sub 2-30.

Synthesis Example of Final Product

1. Synthesis Example of P-1

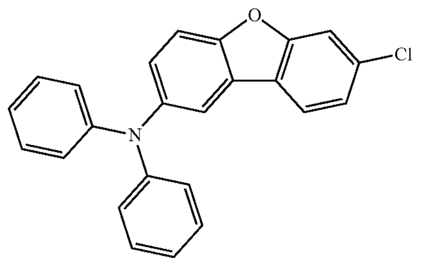

Sub 1-1

+

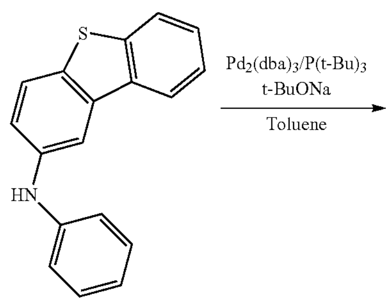

Sub 2-2

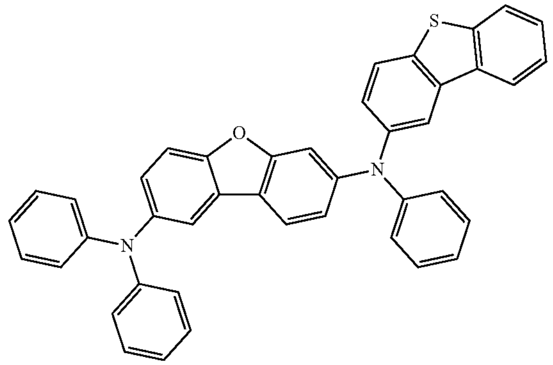

P-1

After Sub 1-1 (7.0 g, 18.9 mmol) was dissolved in toluene (65 ml) in a round bottom flask, Sub 2-2 (5.2 g, 18.9 mmol), $Pd_2(dba)_3$ (0.52 g, 0.57 mmol), $P(t-Bu)_3$ (50 wt % Sol.) (0.46 ml, 1.14 mmol) and t-BuONa (3.64 g, 37.9 mmol) were added the solution and the mixture was stirred at 120° C. When the reaction was completed, the reaction product was washed with water and extracted with methylene chloride. The organic layer was dried with $MgSO_4$ and concentrated. Thereafter, the concentrate was passed through a silica gel column and recrystallized to obtain 9.2 g (yield: 80%) of the product P-1.

2. Synthesis Example of P-25

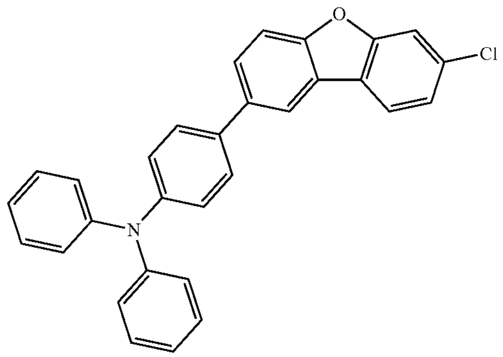

Sub 1-13

+

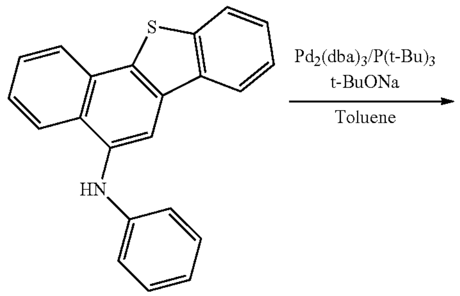

Sub 2-37

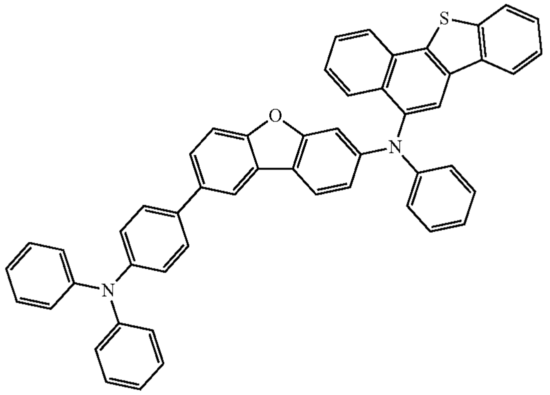

P-25

After Sub 1-13 (10 g, 22.4 mmol) was dissolved in anhydrous toluene (75 ml) in a round bottom flask, Sub 2-37 (7.3 g, 22.4 mmol), $Pd_2(dba)_3$ (0.62 g, 0.67 mmol), $P(t-Bu)_3$ (50 wt % Sol.) (0.54 mL, 1.35 mmol) and t-BuONa (4.31 g, 44.9 mmol) were added the solution and the mixture was stirred at 120° C. When the reaction was completed, the reaction product was washed with water and extracted with methylene chloride. The organic layer was dried with $MgSO_4$ and concentrated. Thereafter, the concentrate was passed through a silica gel column and recrystallized to obtain 13.7 g (yield: 83%) of the product P-25.

3. Synthesis Example of P-59

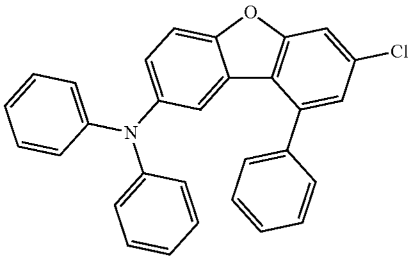

Sub 1-26

+

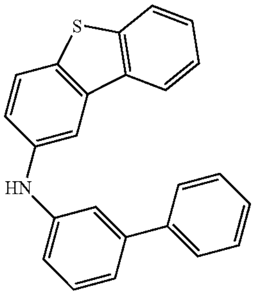

Sub 2-38

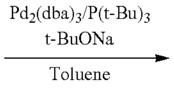

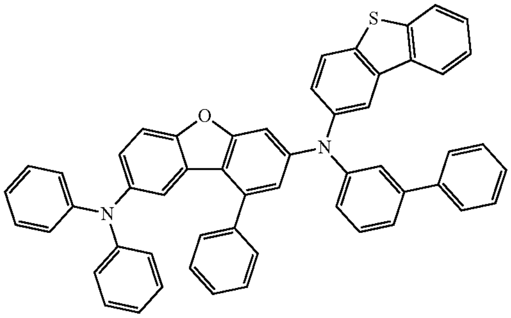

P-59

After Sub 1-26 (5.4 g, 12.1 mmol) was dissolved in anhydrous toluene (40 ml) in a round bottom flask, Sub 2-38 (4.26 g, 12.1 mmol), $Pd_2(dba)_3$ (0.33 g, 0.36 mmol) and $P(t-Bu)_3$ (50 wt % Sol.) (0.29 mL, 0.73 mmol) were added the solution and the mixture was stirred at 120° C. When the reaction was completed, the reaction product was washed with water and extracted with methylene chloride. The organic layer was dried with $MgSO_4$ and concentrated. Thereafter, the concentrate was passed through a silica gel column and recrystallized to obtain 5.98 g (yield: 65%) of the product P-59.

4. Synthesis Example of P-109

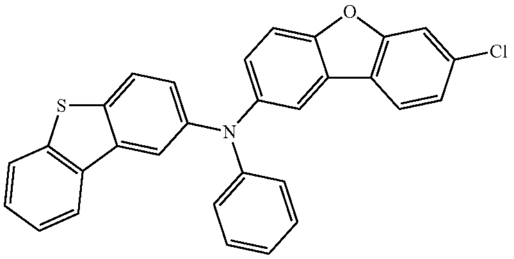

Sub 1-52

+

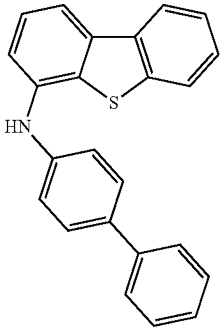

Sub 2-35

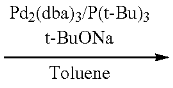

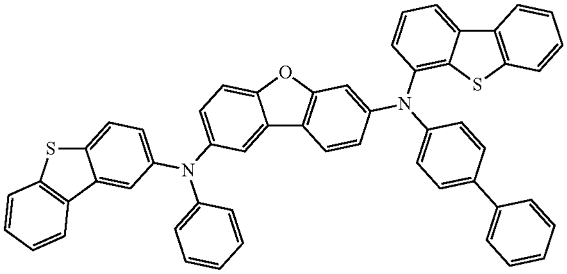

P-109

After Sub 1-52 (8.3 g, 17.4 mmol) was dissolved in anhydrous toluene (60 ml) in a round bottom flask, Sub 2-35 (6.13 g, 17.4 mmol), $Pd_2(dba)_3$ (0.48 g, 0.52 mmol), $P(t-Bu)_3$ (50 wt % Sol.) (0.42 mL, 1.05 mmol) and t-BuONa (3.35 g, 34.9 mmol) were added the solution and the mixture was stirred at 120° C. When the reaction was completed, the reaction product was washed with water and extracted with methylene chloride. The organic layer was dried with $MgSO_4$ and concentrated. Thereafter, the concentrate was passed through a silica gel column and recrystallized to obtain 11.7 g (yield: 85%) of the product P-109.

5. Synthesis Example of P-113

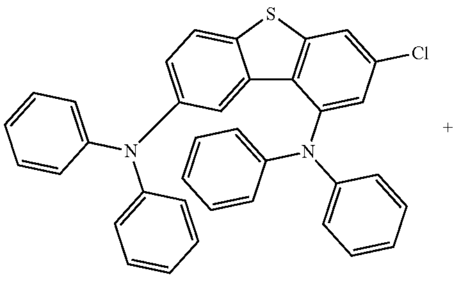

Sub 1-56

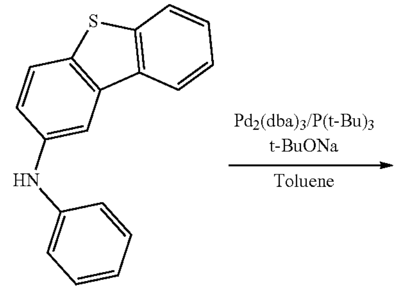

Sub 2-2

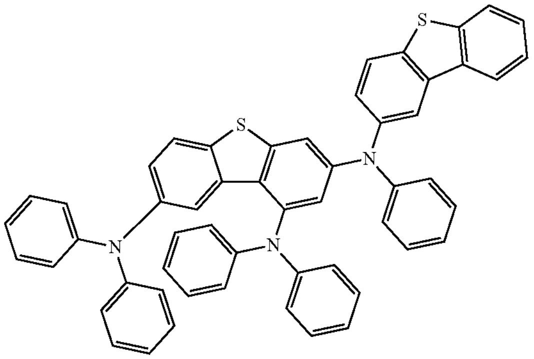

P-113

After Sub 1-56 (13 g, 23.50 mmol) was dissolved in anhydrous toluene (80 ml) in a round bottom flask, Sub 2-2 (6.47 g, 23.50 mmol), $Pd_2(dba)_3$ (0.65 g, 0.71 mmol), $P(t\text{-}Bu)_3$ (50 wt % Sol.) (0.57 mL, 1.41 mmol) and t-BuONa (4.52 g, 47.01 mmol) were added the solution and the mixture was stirred at 120° C. When the reaction was completed, the reaction product was washed with water and extracted with methylene chloride. The organic layer was dried with $MgSO_4$ and concentrated. Thereafter, the concentrate was passed through a silica gel column and recrystallized to obtain 14.52 g (yield: 78%) of the product P-113.

5. Synthesis Example of P-131

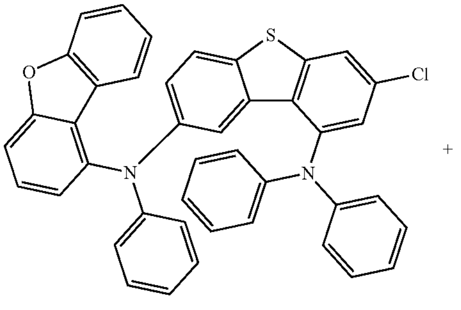

Sub 1-67

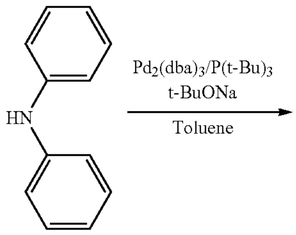

Sub 2-1

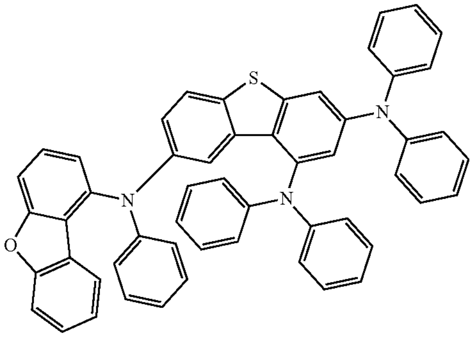

P-131

After Sub 1-67 (9 g, 13.99 mmol) was dissolved in anhydrous toluene (80 ml) in a round bottom flask, Sub 2-1 (2.37 g, 13.99 mmol), $Pd_2(dba)_3$ (0.38 g, 0.42 mmol), $P(t\text{-}Bu)_3$ (50 wt % Sol.) (0.34 mL, 0.84 mmol) and t-BuONa (2.69 g, 27.99 mmol) were added the solution and the mixture was stirred at 120° C. When the reaction was completed, the reaction product was washed with water and extracted with methylene chloride. The organic layer was dried with $MgSO_4$ and concentrated. Thereafter, the concentrate was passed through a silica gel column and recrystallized to obtain 7.93 g (yield: 73%) of the product P-131.

6. Synthesis Example of P-139

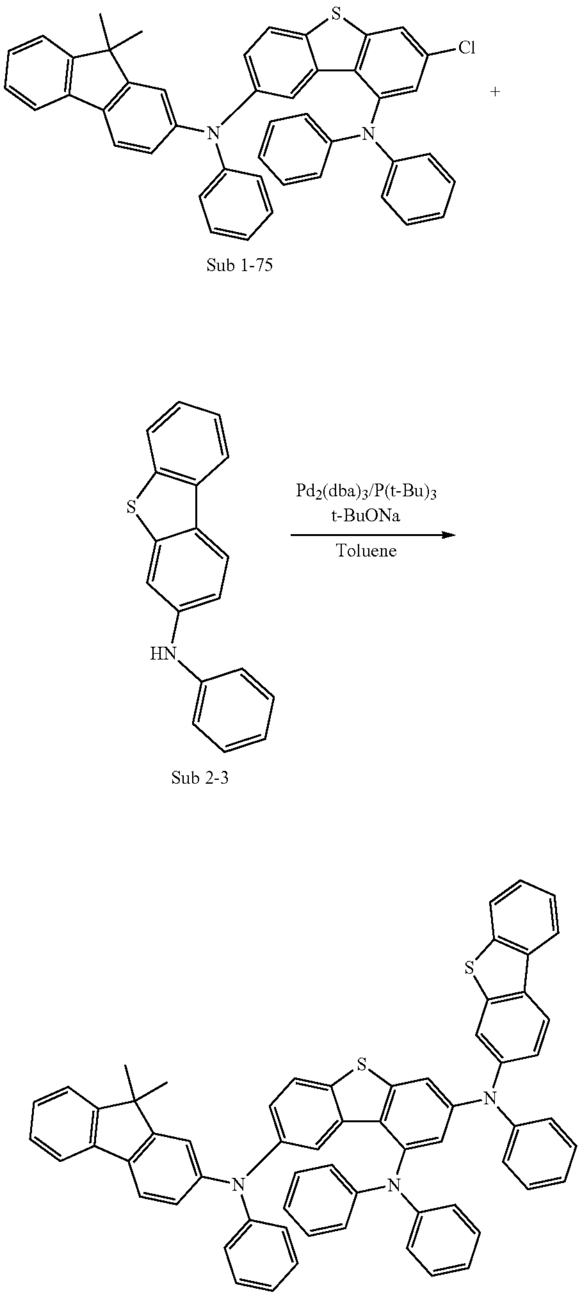

Sub 1-75

Sub 2-3

P-139

After Sub 1-75 (8.5 g, 12.7 mmol) was dissolved in anhydrous toluene (60 ml) in a round bottom flask, Sub 2-3 (3.5 g, 12.7 mmol), $Pd_2(dba)_3$ (0.35 g, 0.38 mmol), $P(t\text{-}Bu)_3$ (50 wt % Sol.) (0.31 mL, 0.76 mmol) and t-BuONa (2.44 g, 25.4 mmol) were added the solution and the mixture was stirred at 120° C. When the reaction was completed, the reaction product was washed with water and extracted with methylene chloride. The organic layer was dried with $MgSO_4$ and concentrated. Thereafter, the concentrate was passed through a silica gel column and recrystallized to obtain 8.54 g (yield: 74%) of the product P-139.

7. Synthesis Example of P-172

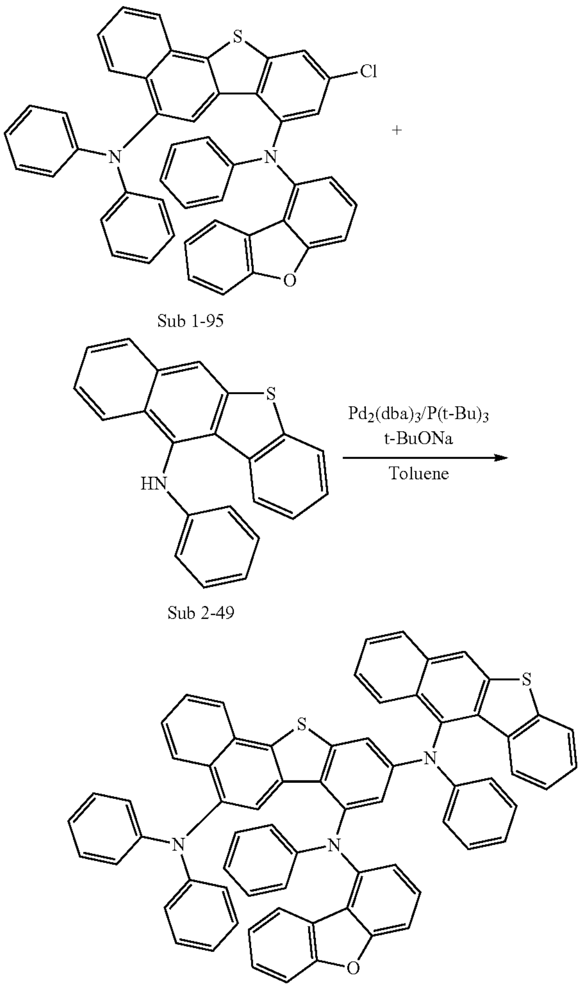

Sub 1-95

Sub 2-49

P-172

After Sub 1-95 (9.8 g, 14.14 mmol) was dissolved in anhydrous toluene (80 ml) in a round bottom flask, Sub 2-49 (4.6 g, 14.14 mmol), $Pd_2(dba)_3$ (0.39 g, 0.42 mmol) and $P(t\text{-}Bu)_3$ (50 wt % Sol.) (0.34 mL, 0.85 mmol) were added the solution and the mixture was stirred at 120° C. When the reaction was completed, the reaction product was washed with water and extracted with methylene chloride. The organic layer was dried with $MgSO_4$ and concentrated. Thereafter, the concentrate was passed through a silica gel column and recrystallized to obtain 9.86 g (yield: 71%) of the product P-172.

Fabrication and Evaluation of Organic Electric Element

[Example 1] Red Organic Electroluminescent Element (an Emission-Auxiliary Layer)

After vacuum-depositing $N^1$-(naphthalen-2-yl)-$N^4$,$N^4$-bis(4-(naphthalen-2-yl(phenyl)amino)phenyl)-$N^1$-phenylbenzene-1,4-diamine (hereinafter, "2-TNATA") on an ITO layer (anode) formed on a glass substrate to form a hole injection layer with a thickness of 60 nm, a hole transport layer with a thickness of 60 nm was formed by vacuum-depositing N,N'-bis(1-naphthalenyl)-N,N'-bis-phenyl-(1,1'-biphenyl)-4,4'-diamine (hereinafter, "NPB") on the hole injection layer.

Next, an emission-auxiliary layer with a thickness of 20 nm was formed by vacuum-depositing the compound P-1 of the present invention on the hole transport layer.

Next, the compound 4,4'-N,N'-dicarbazole-biphenyl (hereinafter, "CBP") as a host material and bis-(1-phenylisoquinolyl)iridium(III)acetylacetonate (hereinafter, "$(piq)_2Ir$ (acac)") as a dopant material in a weight ratio of 95:5 were deposited on the emission-auxiliary layer to form a light emitting layer with a thickness of 30 nm.

Subsequently, (1,1'-bisphenyl-4-olato)bis(2-methyl-8-quinolinolato)aluminum (hereinafter, "BAlq") was vacuum-deposited to a thickness of 10 nm on the light emitting layer to form a hole blocking layer, and bis(10-hydroxybenzo[h]quinolinato)beryllium (hereinafter, "$BeBq_2$") was vacuum-deposited to a thickness of 50 nm on the hole blocking layer to form a an electron transport layer. Thereafter, LiF was deposited to a thickness of 0.2 nm to form an electron injection layer, and then Al was deposited to a thickness of 150 nm to form a cathode.

[Example 2] to [Example 22]

The organic electroluminescent elements were fabricated in the same manner as described in Example 1 except that the compounds of the present invention described in the following Table 4, instead of the compound P-1 of the present invention, were used as material of an emission-auxiliary layer.

[Comparative Example 1] to [Comparative Example 5]

The organic electroluminescent elements were fabricated in the same manner as described in Example 1 except that one of the following Comparative compounds A to E, instead of the compound P-1 of the present invention, were used as material of an emission-auxiliary layer.

<Comp. compd A>

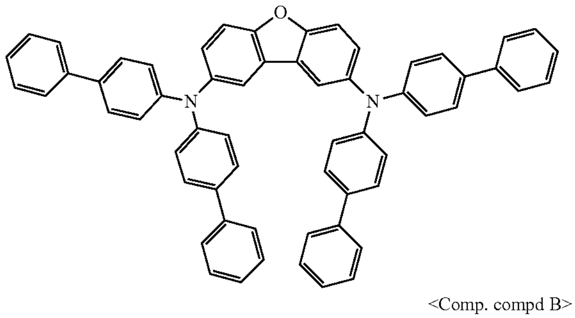

<Comp. compd B>

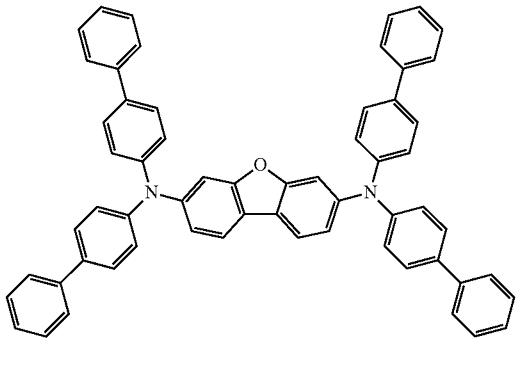

-continued

<Comp. compd C>

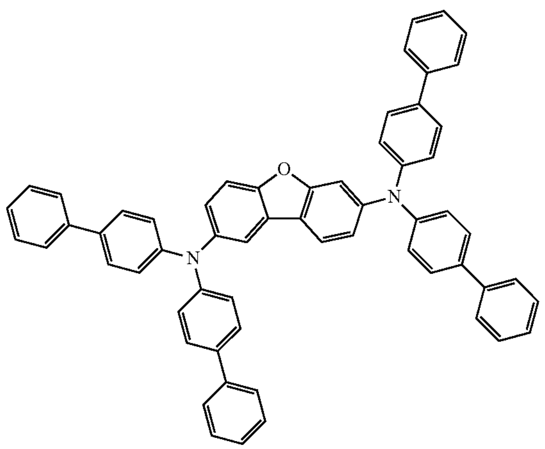

<Comp. compd D>

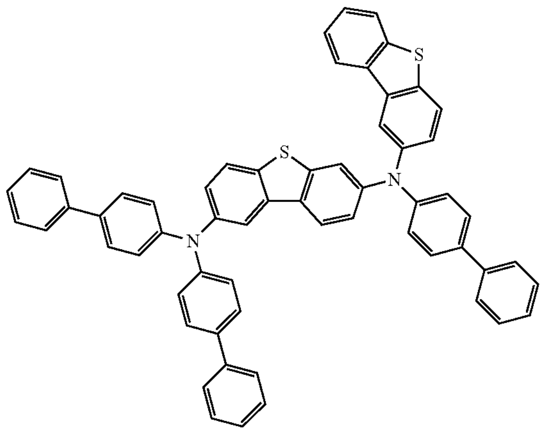

<Comp. compd E>

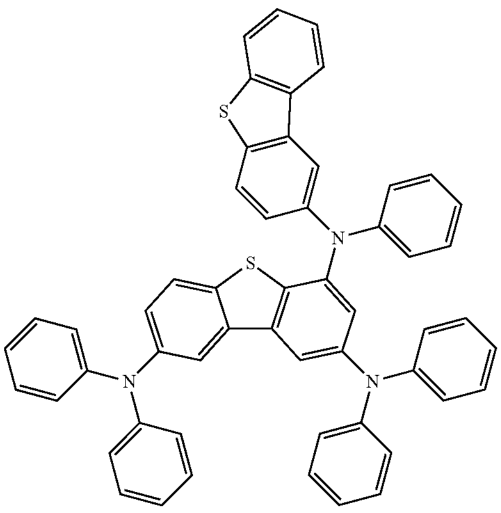

Electroluminescence (EL) characteristics were measured with a PR-650 (Photoresearch) by applying a forward bias DC voltage to the organic electroluminescent elements prepared in Examples 1 to 22 of the present invention and Comparative Examples 1 to 5. And, the T95 life time was measured using a life time measuring apparatus manufactured by ms science Inc. at reference brightness of 2500 cd/$m^2$. The measurement results are shown in Tables 4 below.

TABLE 4

| | Compound | Voltage (V) | Current Density ($mA/cm^2$) | Brightness ($cd/m^2$) | Efficiency (cd/A) | Lifetime T(95) | CIE x | CIE y |
|---|---|---|---|---|---|---|---|---|
| comp.Ex(1) | comp.Com A | 5.9 | 22.9 | 2500.0 | 10.9 | 114.1 | 0.64 | 0.32 |
| comp.Ex(2) | comp.Com B | 5.7 | 24.8 | 2500.0 | 10.1 | 119.8 | 0.61 | 0.34 |
| comp.Ex(3) | comp.Com C | 5.5 | 18.1 | 2500.0 | 13.8 | 123.2 | 0.63 | 0.30 |
| comp.Ex(4) | comp.Com D | 5.1 | 10.8 | 2500.0 | 23.1 | 115.1 | 0.64 | 0.32 |
| comp.Ex(5) | comp.Com E | 5.1 | 10.3 | 2500.0 | 23.6 | 115.7 | 0.63 | 0.33 |
| Ex.(1) | P-1 | 5.0 | 10.6 | 2500.0 | 23.7 | 139.3 | 0.61 | 0.31 |
| Ex.(2) | P-6 | 5.0 | 10.1 | 2500.0 | 24.8 | 136.5 | 0.61 | 0.31 |
| Ex.(3) | P-11 | 5.0 | 10.3 | 2500.0 | 24.2 | 138.8 | 0.61 | 0.35 |
| Ex.(4) | P-16 | 4.9 | 10.5 | 2500.0 | 23.9 | 138.4 | 0.62 | 0.33 |
| Ex.(5) | P-19 | 5.0 | 10.1 | 2500.0 | 24.8 | 138.7 | 0.64 | 0.34 |
| Ex.(6) | P-26 | 5.0 | 10.6 | 2500.0 | 23.6 | 135.8 | 0.63 | 0.33 |
| Ex.(7) | P-29 | 5.0 | 10.3 | 2500.0 | 24.2 | 136.7 | 0.62 | 0.31 |
| Ex.(8) | P-38 | 5.1 | 10.9 | 2500.0 | 23.0 | 132.8 | 0.64 | 0.33 |
| Ex.(9) | P-47 | 5.1 | 10.7 | 2500.0 | 23.4 | 131.3 | 0.63 | 0.32 |
| Ex.(10) | P-49 | 5.0 | 10.6 | 2500.0 | 23.5 | 135.2 | 0.61 | 0.31 |
| Ex.(11) | P-69 | 5.1 | 10.7 | 2500.0 | 23.3 | 133.0 | 0.62 | 0.35 |
| Ex.(12) | P-109 | 5.1 | 10.6 | 2500.0 | 23.5 | 131.2 | 0.63 | 0.34 |
| Ex.(13) | P-113 | 4.9 | 9.3 | 2500.0 | 26.9 | 134.8 | 0.65 | 0.30 |
| Ex.(14) | P-118 | 5.0 | 9.6 | 2500.0 | 26.0 | 135.0 | 0.63 | 0.32 |
| Ex.(15) | P-120 | 5.1 | 9.5 | 2500.0 | 26.2 | 134.6 | 0.63 | 0.31 |
| Ex.(16) | P-128 | 4.9 | 9.5 | 2500.0 | 26.3 | 133.7 | 0.64 | 0.32 |
| Ex.(17) | P-130 | 5.0 | 9.7 | 2500.0 | 25.8 | 134.6 | 0.60 | 0.31 |
| Ex.(18) | P-134 | 5.1 | 9.8 | 2500.0 | 25.5 | 133.4 | 0.62 | 0.30 |
| Ex.(19) | P-149 | 5.1 | 10.1 | 2500.0 | 24.7 | 133.2 | 0.61 | 0.33 |
| Ex.(20) | P-155 | 4.9 | 9.8 | 2500.0 | 25.4 | 134.1 | 0.65 | 0.30 |
| Ex.(21) | P-165 | 5.1 | 9.9 | 2500.0 | 25.2 | 136.1 | 0.62 | 0.32 |
| Ex.(22) | P-179 | 5.1 | 10.0 | 2500.0 | 24.9 | 135.9 | 0.62 | 0.32 |

As can be seen from the results of Table 4, not only can the driving voltage be lowered, but efficiency and lifespan are significantly improved where the compound of the present invention is used as material for an emission-auxiliary layer, compared to the cases of using Comparative Compounds A to E.

In Comparative Examples 1 to 3, Comparative Compounds A to C were used as material for an emission-auxiliary layer, respectively. Comparative compounds A to C are the same in that two identical amine groups are bonded to the benzene ring of the dibenzofuran core, but the bonding positions of the amine groups are different from each other. It was confirmed that efficiency and lifespan as well as driving voltage were improved where the Comparative compound C in which the amine group was bonded to 2-position and 7-position of the dibenzofuran, respectively. That is, it can be seen that the performance of the device is improved where the comparative compound C in which the amine group is asymmetrically bonded to the dibenzofuran (bonded at positions 2 and 7) is used as an emission-auxiliary layer material, compared to where Comparative Compound A (bonded at positions 2 and 8 of dibenzofuran) or Comparative Compound B (bonded at positions 3 and 7 of dibenzofuran) in which amine groups are symmetrically bonded to dibenzofuran.

In the specification, the numbering for dibenzofuran or dibenzothiophene is as follows.

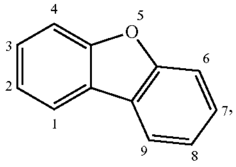

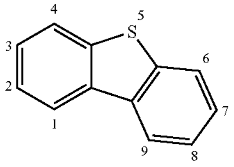

From these results, it can be seen that even if the cores are the same, device characteristics vary depending on the bonding position of the amine group. It seems that this is because the value of energy level (especially HOMO level) and physical properties are changed depending on the bonding position of the amine group, and this change acts as a major factor in improving the performance of the device when material is deposited during manufacturing of device.

On the other hand, the compound of the present invention used in Examples is similar to Comparative Compound C in that the amine group is bonded to the both benzene ring of the core in an asymmetric position, but is different in that at least one of $Ar^1$ to $Ar^4$ bonded to the amine group is dibenzothiophene or dibenzofuran. That is, biphenyl is bound to all of the nitrogen of the amine group in Comparative Compound C, but the compound of the present invention is different in that at least one of these biphenyl is replaced with dibenzothiophene or dibenzofuran.

Due to these differences, the driving voltage, efficiency and lifetime of the organic electroluminescent element of Examples 1 to 22 employing the compound of the present invention were significantly improved than Comparative Example 3 using Comparative Compound C as material for an emission-auxiliary layer.

From these results, it can be seen that the characteristics of the element are significantly changed as the type of the substituent is changed even if the amine group is bonded to the same position of the core. It appears that efficiency and thermal stability are improved because the refractive index is significantly higher and Tg also rises where dibenzothiophene or dibenzofuran is introduced as a substituent, compared to the case where a general aryl group is introduced.

On the other hand, it can be seen that the comparative compound E, in which three amine groups are bonded, is improved in efficiency and lifespan, compared to the comparative compound D, in which two amine groups are bonded to a dibenzothiophene core. This is because by introducing the amine group within an appropriate range, without excessively increasing the number of amine groups introduced, the HOMO energy level of an emission-auxiliary layer is adjusted, and an emission-auxiliary layer has a most suitable HOMO energy level difference from the light-emitting layer, as a result, the charge balance is increased and thus the light emission is better performed in the light-emitting layer.

In addition, the device results of Examples 13 to 22 employing the compound of the present invention are better than Comparative Example 5 employing Comparative Compound E. When comparing these compounds, it is the same that the three amine groups are substituted in the core, but three amine groups are bonded at (2, 6, 8)-position of the dibenzothiophene core in Comparative Compound E, whereas three amine groups are bonded at (2, 7, 9)-position of the dibenzothiophene or dibenzofuran core.

This is because the HOMO value is deeper and hole injection and hole mobility becomes faster where the amine groups are combined at 7- and 9-positions of one benzene ring like the compounds of the present invention, compared to the case where the amine groups are combined at 6- and 8-positions.

From these results, it can be seen that even if the core of compound is a similar, the characteristics such as hole characteristics, light efficiency characteristics, energy levels (LUMO, HOMO level, T1 level), hole injection, hole mobility and electron blocking ability vary depending on the bonding position of a substituent such as an amine group, and completely different device results can be derived due to differences in these characteristics.

Although the exemplary embodiments of the present invention have been described for illustrative purposes, those skilled in the art to which the present invention pertains will be capable of various modifications without departing from the essential characteristics of the present invention. Therefore, the embodiment disclosed herein is intended to illustrate the scope of the technical idea of the present invention, and the spirit and scope of the present invention are not limited by the embodiments. The scope of the present invention shall be construed on the basis of the accompanying claims, and it shall be construed that all of the technical ideas included within the scope equivalent to the claims belong to the present invention.

The invention claimed is:

1. A compound of Formula 1:

<Formula 1>

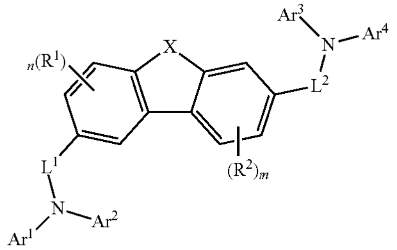

<Formula 1-1>

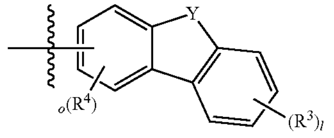

wherein:

$Ar^1$ to $Ar^4$ are each independently selected from the group consisting of halogen, a $C_6$-$C_{60}$ aryl group, a fluorenyl group, a $C_2$-$C_{60}$ heterocyclic group containing at least one heteroatom of O, N, S, Si, and P, a $C_3$-$C_{60}$ aliphatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group, and Formula 1-1, and $Ar^1$ and $Ar^2$ together or $Ar^3$ and $Ar^4$ together may be bonded to each other to form a ring, with the proviso that at least one of $Ar^1$ to $Ar^4$ is Formula 1-1, $L^1$ and $L^2$ are each independently selected from the group consisting of a single bond, a $C_6$-$C_{60}$ arylene group, a fluorenylene group, a $C_2$-$C_{60}$ heterocyclic group containing at least one heteroatom of O, N, S, Si, and P, a $C_3$-$C_{60}$ aliphatic ring and a combination thereof, X is O, Y is O or S, $R^1$, $R^2$, and $R^4$ are each independently selected from the group consisting of hydrogen, deuterium, halogen, a $C_6$-$C_{60}$ aryl group, a fluorenyl group, a $C_2$-$C_{60}$ heterocyclic group containing at least one heteroatom of O, N, S, Si, and P, a $C_3$-$C_{60}$ aliphatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N($R_a$)($R_b$), and at least one of $R^1$ and $R^2$ is -L'-N($R_a$)($R_b$), and adjacent groups together may be bonded to each other to form a ring, $R^3$ is selected from the group consisting of hydrogen, deuterium, halogen, a $C_6$-$C_{60}$ aryl group, a fluorenyl group, a $C_2$-$C_{60}$ heterocyclic group containing at least one heteroatom of O, N, S, Si, and P, a $C_3$-$C_{60}$ aliphatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, and a $C_6$-$C_{30}$ aryloxy group, and adjacent groups together may be bonded to each other to form a ring, 1 is an integer of 1 to 4, m, n and o are each an integer of 1 to 3, where they are each an integer of 2 or more, each of a plurality of $R^1$s, each of a plurality of $R^2$s, each of a plurality of $R^3$s, each of a plurality of $R^4$s are the same or different from each other, L' is selected from the group consisting of a single bond, a $C_6$-$C_{60}$ arylene group, a fluorenylene group, a $C_3$-$C_{60}$ aliphatic ring and a $C_2$-$C_{60}$ heterocyclic group containing at least one heteroatom of O, N, S, Si, and P, and $R_a$ and $R_b$ are each independently selected from the group consisting of a $C_6$-$C_{60}$ aryl group, a fluorenyl group, a fused ring group formed by a $C_3$-$C_{60}$ aliphatic ring with a $C_6$-$C_{60}$ aromatic ring, and a $C_2$-$C_{60}$ heterocyclic group containing at least one heteroatom of O, N, S, Si, and P, $Ar^1$ to $Ar^4$, $L^1$, $L^2$, L', $R^1$ to $R^4$, $R_a$, $R_b$, and the ring formed by adjacent groups are each optionally substituted with one or more substituents selected from the group consisting of deuterium, halogen, a silane group unsubstituted or substituted with a $C_1$-$C_{20}$ alkyl group or a $C_6$-$C_{20}$ aryl group, a siloxane group, a boron group, a germanium group, a cyano group, a nitro group, a phosphine oxide group unsubstituted or substituted with a $C_1$-$C_{20}$ alkyl group or a $C_6$-$C_{20}$ aryl group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom of O, N, S, Si, and P, a $C_3$-$C_{20}$ cycloalkyl group, a $C_7$-$C_{20}$ arylalkyl group, and $C_8$-$C_{20}$ arylalkenyl group.

2. The compound of claim 1, wherein Formula 1 is represented by Formula 2 or Formula 3:

<Formula 2>

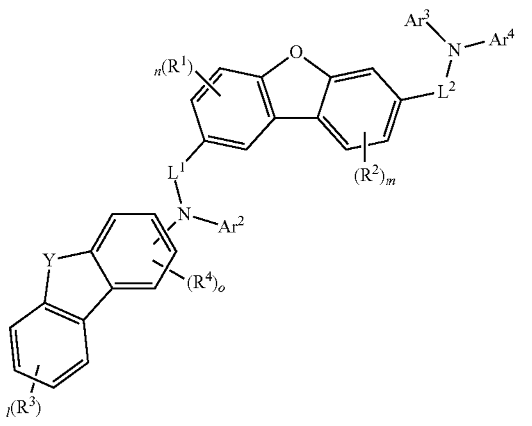

<Formula 3>

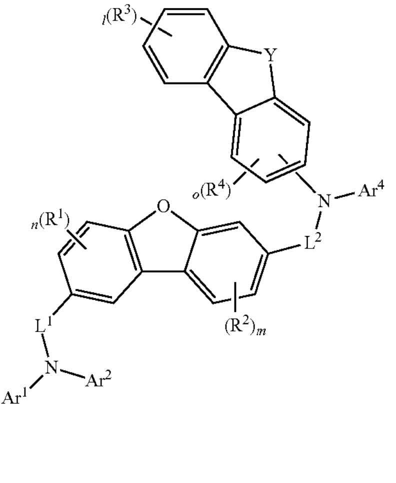

wherein $Ar^1$ to $Ar^4$, $R^1$ to $R^4$, $L^1$, $L^2$, Y, l, m, n and o are the same as defined in claim 1.

3. The compound of claim 1, wherein Formula 1 is represented by one of Formula 8 to Formula 13:

<Formula 8>

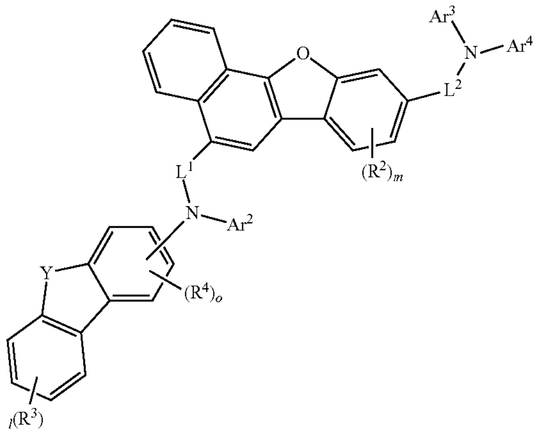

<Formula 9>

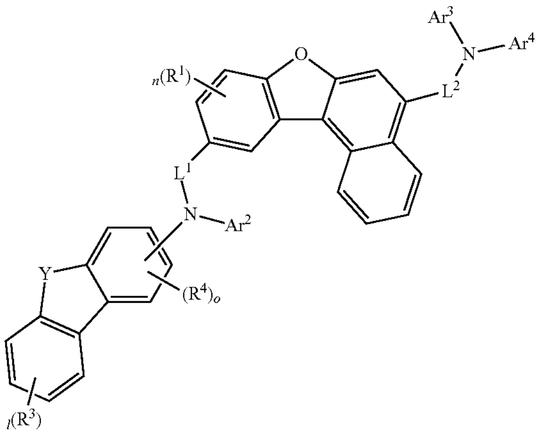

<Formula 11>

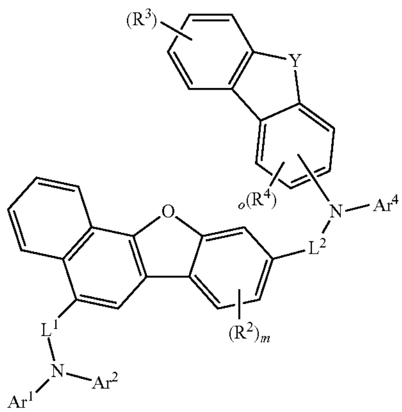

-continued

<Formula 12>

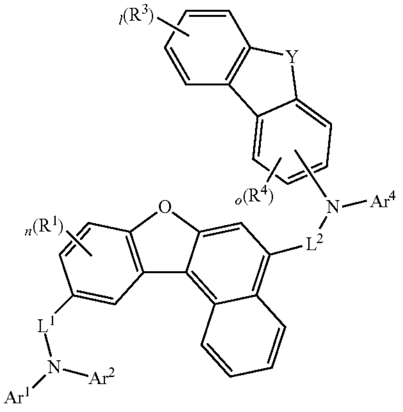

wherein $Ar^1$ to $Ar^4$, $R^1$ to $R^4$, $L^1$, $L^2$, Y, l, m, n and o are the same as defined in claim 1.

4. The compound of claim 1, wherein Formula 1 is represented by Formula 14 or Formula 15:

<Formula 14>

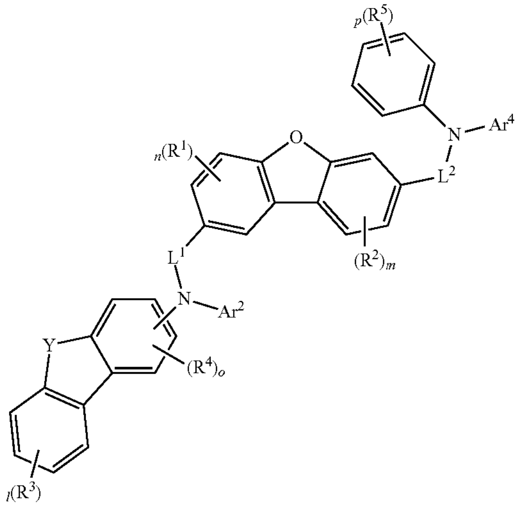

<Formula 15>

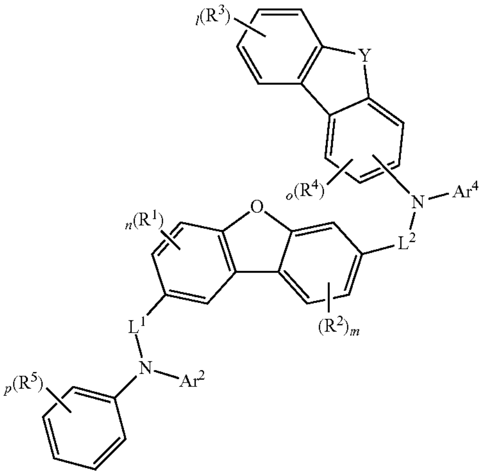

wherein $Ar^2$, $Ar^4$, $R^1$ to $R^4$, $L^1$, $L^2$, Y, l, m, n and o are the same as defined in claim 1, $R^5$ is each independently selected from the group consisting of hydrogen, deuterium, halogen, a $C_6$-$C_{20}$ aryl group, a fluorenyl group, a $C_2$-$C_{20}$ heterocyclic group containing at least one heteroatom of O, N, S, Si, and P, a $C_3$-$C_{20}$ aliphatic ring, a $C_1$-$C_{20}$ alkyl group, a $C_2$-$C_{10}$ alkenyl group, a $C_2$-$C_{10}$ alkynyl group, a $C_1$-$C_{10}$ alkoxyl group, a $C_6$-$C_{10}$ aryloxy group and -L'-N($R_a$)($R_b$), adjacent $R^5$s together may be bonded to each other to form a ring, p is an integer of 0 to 5, and when p is an integer of 2 or more, each of a plurality of $R^5$s is the same or different from each other.

5. The compound of claim 1, wherein the compound represented by Formula 1 is one of the following compounds:

P-73

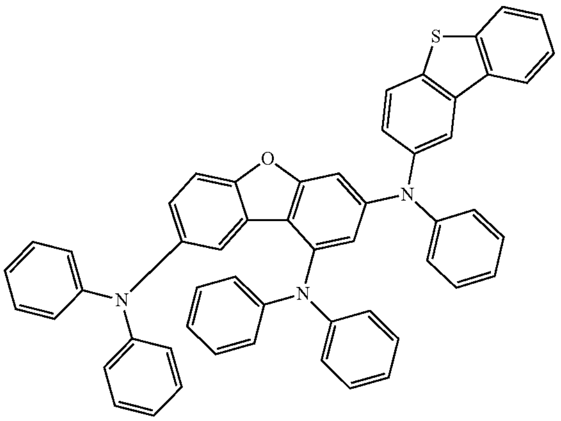

P-74

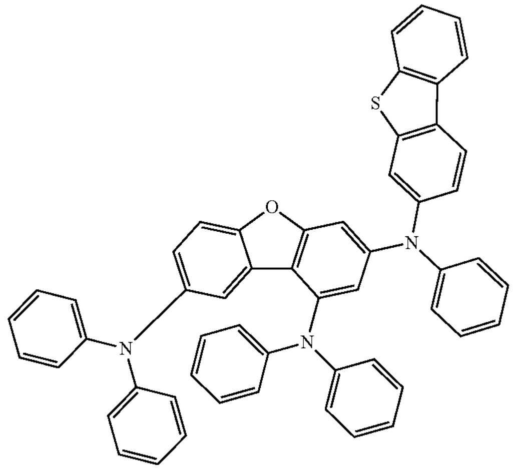

-continued
P-75
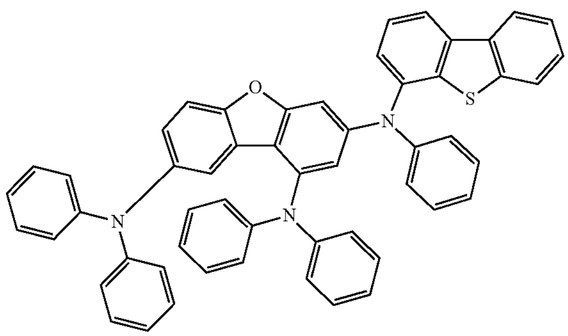
P-76
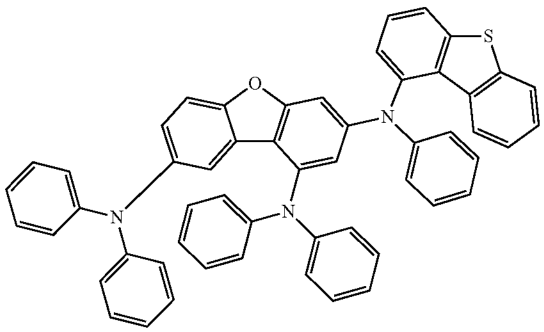
P-77
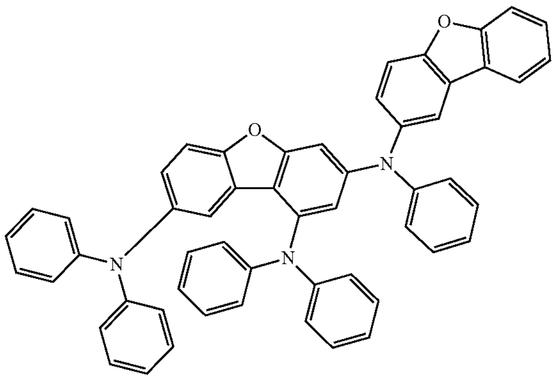
P-78
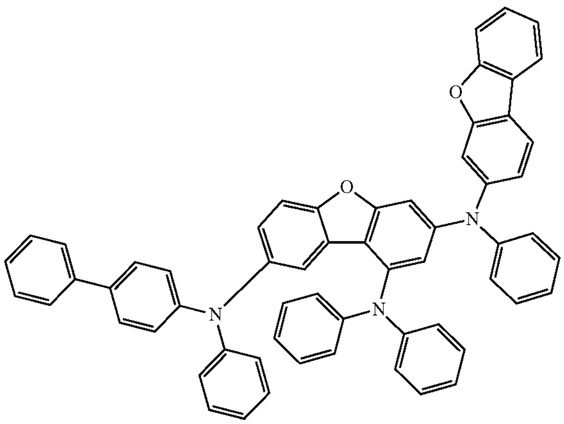
-continued
P-79
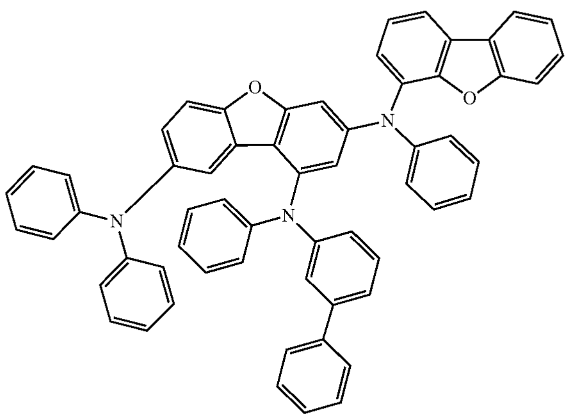
P-80
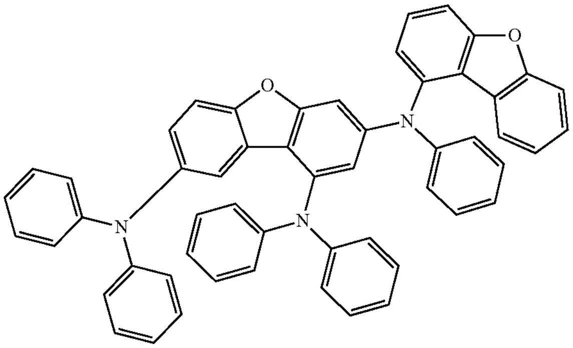
P-81
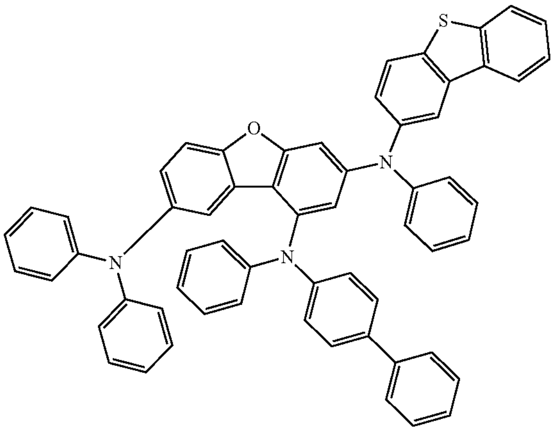

-continued
P-82
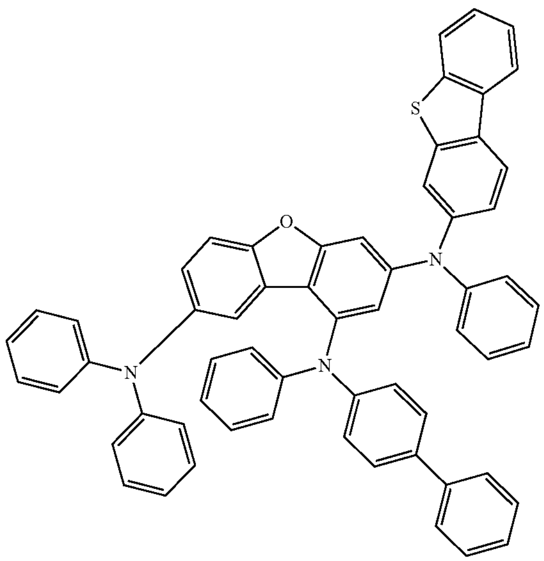
P-83
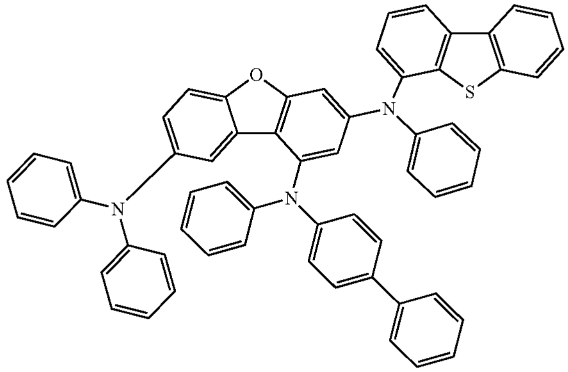
P-84
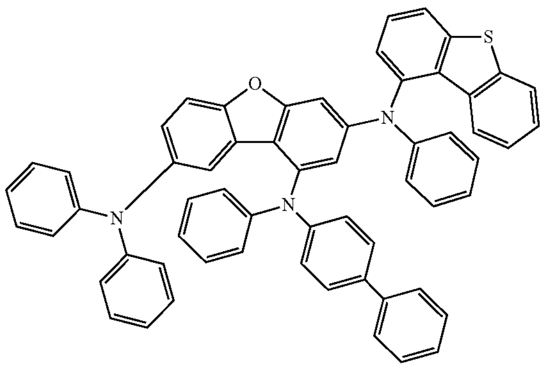
-continued
P-85
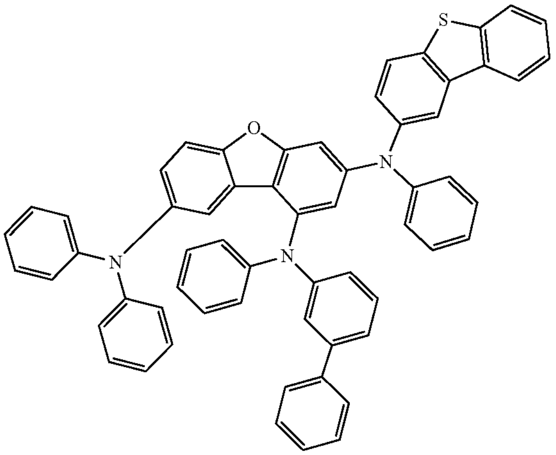
P-86
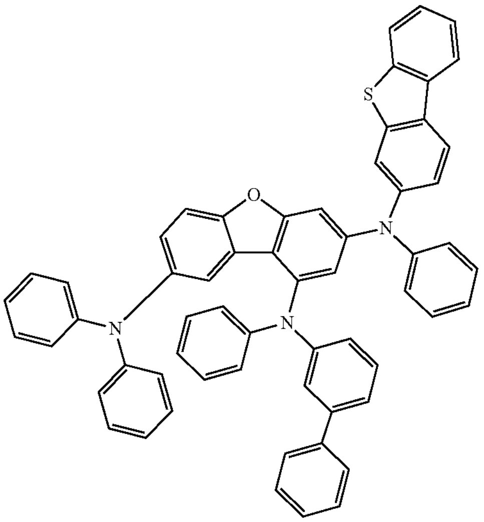
P-87
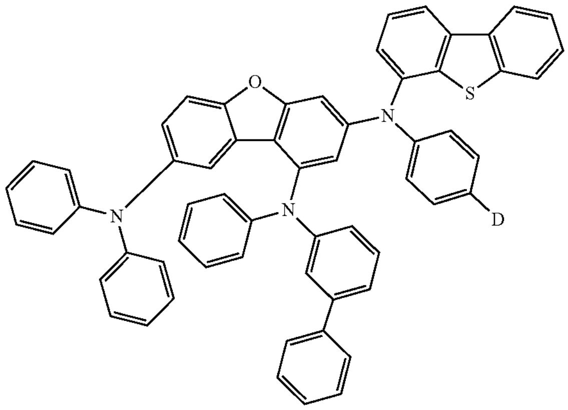

-continued
P-88
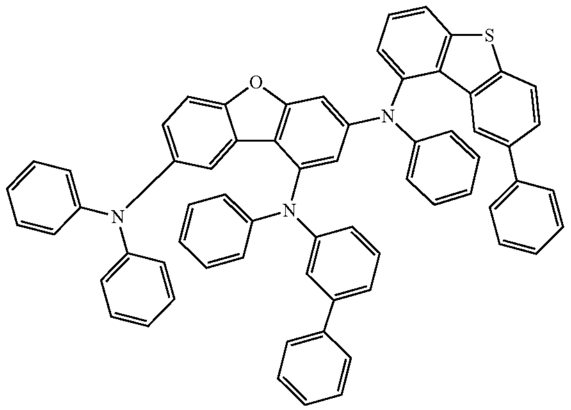
P-89
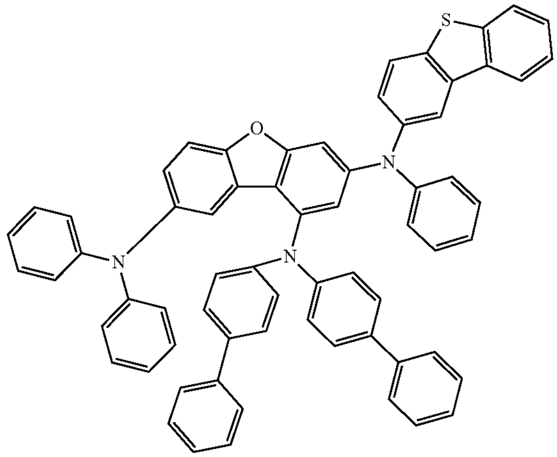
P-90
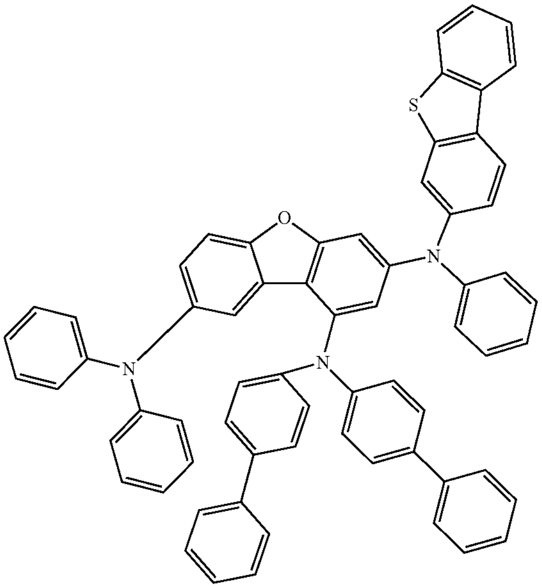
-continued
P-91
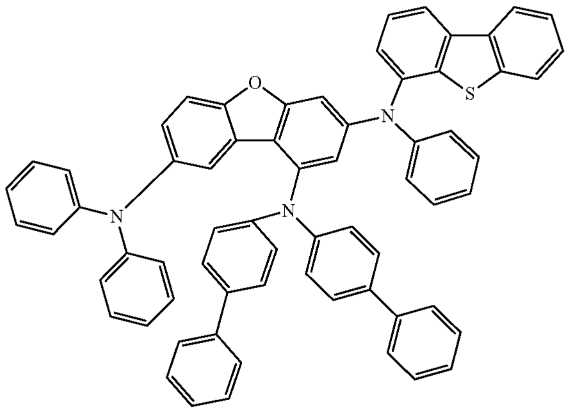
P-92
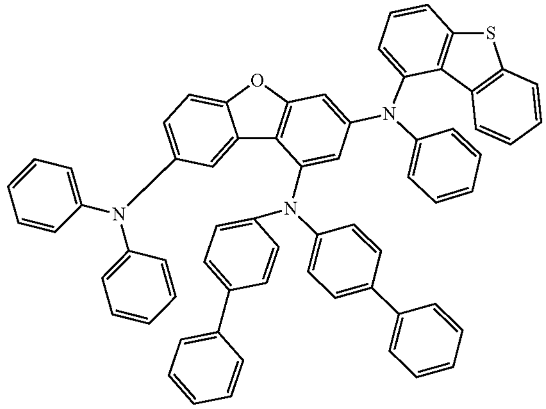
P-93
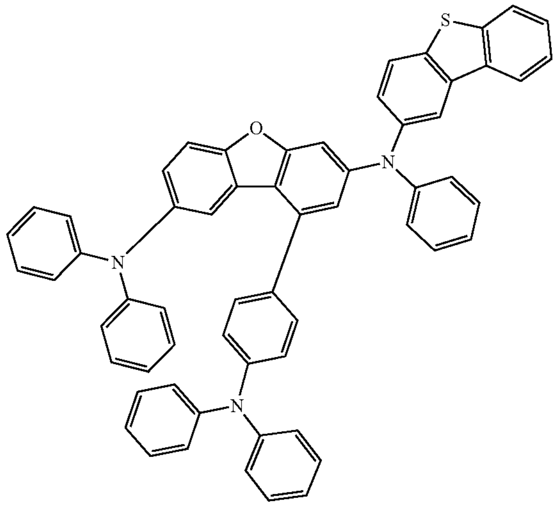

-continued
P-94
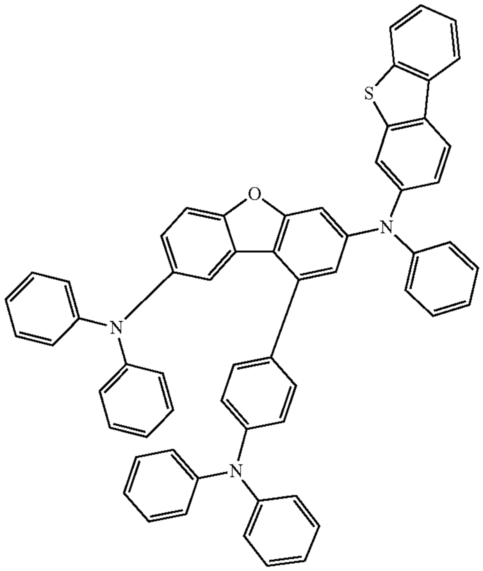
P-95
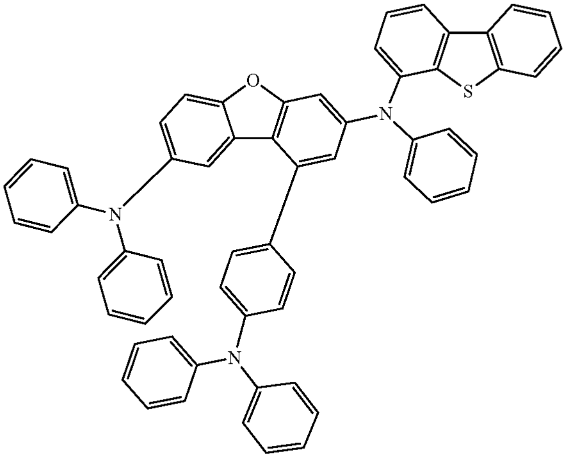
P-96
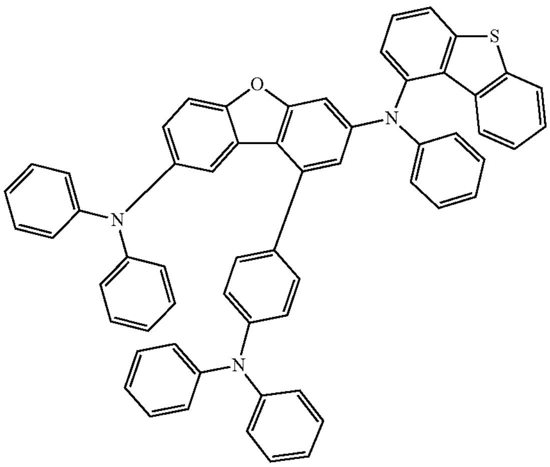
-continued
P-161
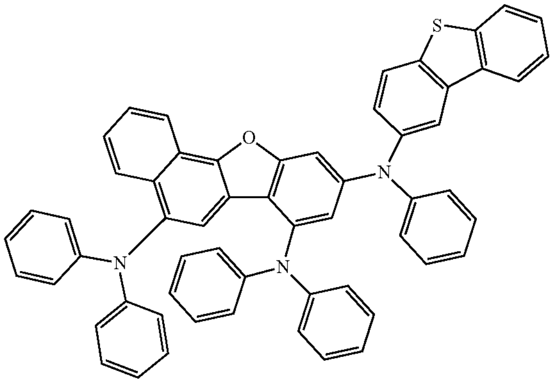
P-162
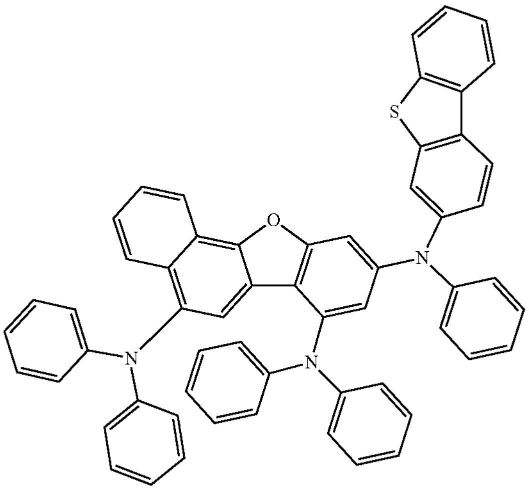
P-163
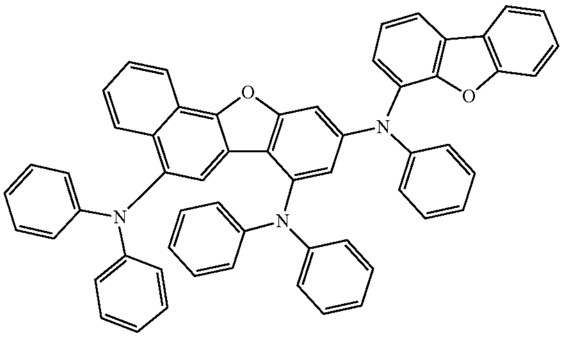
P-164
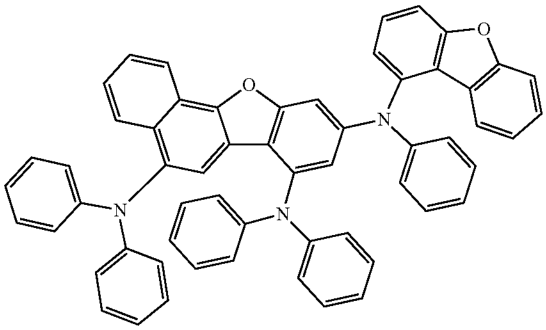

-continued
P-165
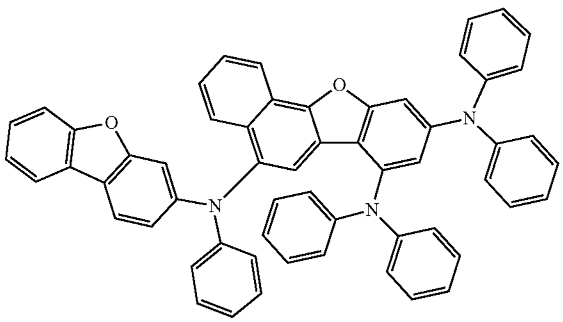
P-166
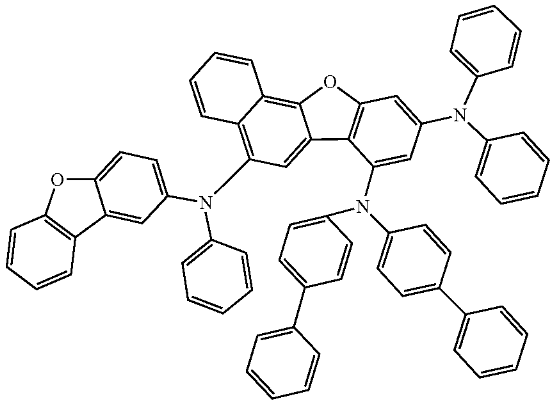
P-167
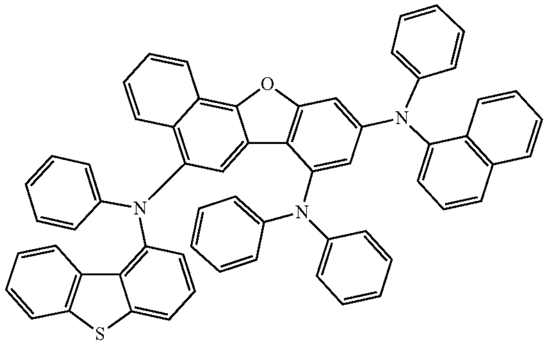
P-168
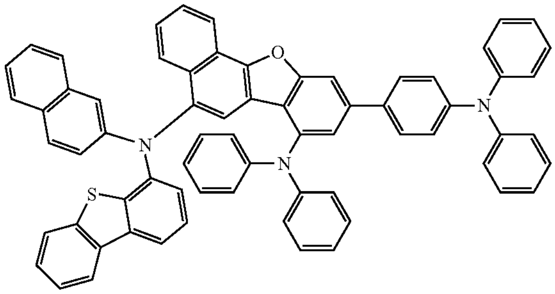
-continued
P-177
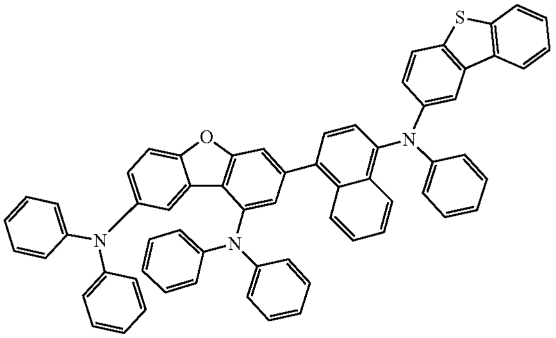
P-178
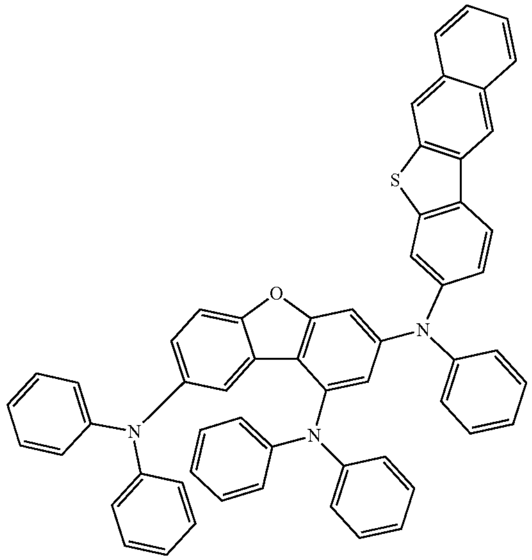
P-179
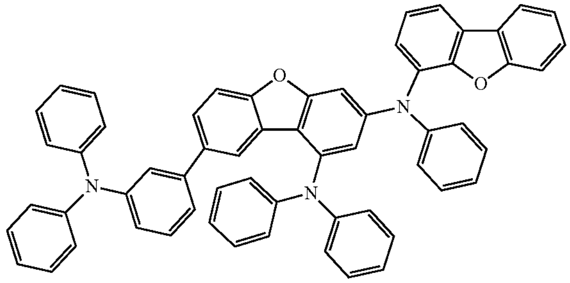
P-180
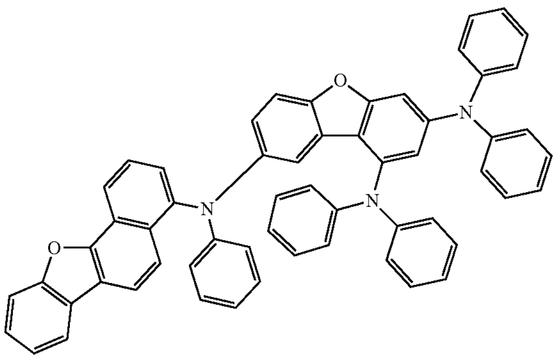

-continued

P-183

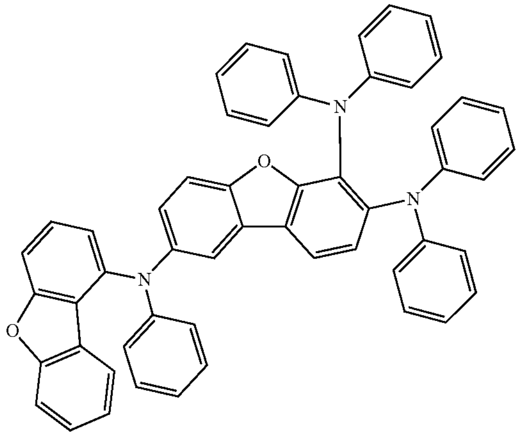

P-184

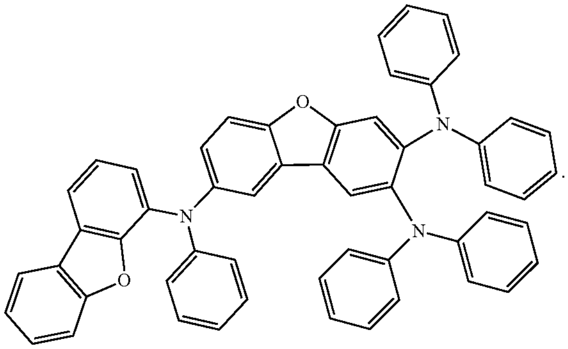

6. An organic electric element comprising a first electrode, a second electrode, and an organic material layer formed between the first electrode and the second electrode, wherein the organic material layer comprises a single compound or two or more compounds represented by Formula 1 of claim 1.

7. The organic electric element of claim 6, wherein the organic material layer comprises at least one of a hole injection layer, a hole transport layer, an emission-auxiliary layer, a light emitting layer, an electron transport-auxiliary layer, an electron transport layer and an electron injection layer.

8. The organic electric element of claim 6, wherein the compound is comprised in the emission-auxiliary layer.

9. An electronic device comprising a display device and a control unit for driving the display device, wherein the display device comprises the organic electric element of claim 6.

10. The electronic device of claim 9, wherein the organic electric element is selected from the group consisting of an organic electroluminescent element, an organic solar cell, an organic photo conductor, an organic transistor, an element for monochromatic illumination and element for quantum dot display.

* * * * *